(12) United States Patent
Daneshvar

(10) Patent No.: US 10,973,669 B2
(45) Date of Patent: *Apr. 13, 2021

(54) DANESHVAR WRAPPING MEANS II AND METHODS

(75) Inventor: Yousef Daneshvar, WestBloomfield, MI (US)

(73) Assignee: AMERICAN MEDICAL CORPORATION

( * ) Notice: Subject to any disclaimer, the term of this patent is extended or adjusted under 35 U.S.C. 154(b) by 2213 days.

This patent is subject to a terminal disclaimer.

(21) Appl. No.: 11/704,635

(22) Filed: Feb. 9, 2007

(65) Prior Publication Data

US 2007/0191747 A1 Aug. 16, 2007

Related U.S. Application Data

(60) Provisional application No. 60/771,819, filed on Feb. 10, 2006.

(51) Int. Cl.
*A61F 5/01* (2006.01)
*A61F 13/02* (2006.01)

(52) U.S. Cl.
CPC ........ *A61F 5/0111* (2013.01); *A61F 13/0273* (2013.01)

(58) Field of Classification Search
CPC .............. A61F 13/0273; A61F 13/0286; A61F 13/0289; A61F 13/06–148; A61F 5/01–03; A61F 5/37–3792
USPC .............. 602/4–5, 23, 26, 27, 75, 41, 60–79
See application file for complete search history.

(56) References Cited

U.S. PATENT DOCUMENTS

| | | | |
|---|---|---|---|
| 3,480,012 A * | 11/1969 | Smithers ................. | A61F 13/06 128/DIG. 15 |
| 4,085,872 A | 4/1978 | Foo | |
| 4,215,687 A * | 8/1980 | Shaw ............................. | 602/60 |
| 4,353,362 A * | 10/1982 | DeMarco .............. | A61F 5/0109 602/26 |
| 4,665,909 A | 5/1987 | Trainor | |

(Continued)

*Primary Examiner* — Alireza Nia
*Assistant Examiner* — Michelle J Lee

(57) ABSTRACT

This invention is related to an improved version of the wound wrapping, support means and compression units for use in a living body. Rapid wound dressing and wrapping are of significant importance and may save a lot of complications and lives. Also as important is the stability of the wrapped unit, a unit which does not stay stable on the wound will not function properly. The wound compression and prevention of bleeding are of significant importance as well as covering the whole area and preventing a site of wound to be covered. The compression also would be helpful and needed after certain surgeries to prevent complication and reach the ultimate goal. The adjustablility and being able to use one unit in more patients are of clinical and economical importance. This invention introduces a models combination of support units with straps, that can be used in various parts of the body. The new version allows the user to wrap a leg or arm easily and more securely. The use of more than one support is again stressed, different ways of use of these units are also discussed. Also new is the use of stretchable hoses for allowing the straps to be held in place more securely. So that these better unit can make the patient care a bit easier and help humanity.

23 Claims, 17 Drawing Sheets

(56) References Cited

U.S. PATENT DOCUMENTS

| | | | | |
|---|---|---|---|---|
| 4,672,722 | A | * | 6/1987 | Malamed ............ A44B 18/003 |
| | | | | 128/DIG. 15 |
| 5,113,877 | A | * | 5/1992 | Johnson et al. ............ 128/882 |
| 5,120,300 | A | * | 6/1992 | Shaw ............................ 602/61 |
| 5,243,991 | A | * | 9/1993 | Marks ............... A61B 5/02233 |
| | | | | 128/DIG. 15 |
| 5,254,122 | A | * | 10/1993 | Shaw ........................... 606/201 |
| 5,328,446 | A | | 7/1994 | Bunnell et al. |
| 5,338,290 | A | | 8/1994 | Aboud |
| 5,468,219 | A | * | 11/1995 | Crippen ........................... 602/6 |
| 5,514,155 | A | | 5/1996 | Daneshvar |
| 5,779,657 | A | | 7/1998 | Daneshvar |
| 5,918,602 | A | * | 7/1999 | Shaw et al. .................. 128/882 |
| 6,109,267 | A | * | 8/2000 | Shaw et al. .................. 128/882 |
| 7,135,007 | B2 | * | 11/2006 | Scott .................... A61F 13/085 |
| | | | | 602/75 |
| 7,297,128 | B2 | * | 11/2007 | Binder .................... A61D 9/00 |
| | | | | 602/42 |
| 7,942,838 | B2 | * | 5/2011 | Farrow ................. A61H 9/005 |
| | | | | 602/13 |
| 8,556,841 | B2 | * | 10/2013 | Daneshvar .......... A61F 13/0273 |
| | | | | 602/41 |
| 9,468,560 | B1 | * | 10/2016 | Daneshvar ............ A61F 13/066 |
| 2004/0064078 | A1 | * | 4/2004 | Winters ......................... 602/27 |
| 2005/0192524 | A1 | * | 9/2005 | Lipshaw ................ A61F 13/06 |
| | | | | 602/62 |
| 2005/0288615 | A1 | * | 12/2005 | Gaylord ............... A61F 5/0111 |
| | | | | 602/65 |
| 2006/0094999 | A1 | * | 5/2006 | Cropper ............... A61F 5/0109 |
| | | | | 602/60 |
| 2006/0282938 | A1 | * | 12/2006 | Jewell ............... A41D 13/0581 |
| | | | | 2/227 |

\* cited by examiner

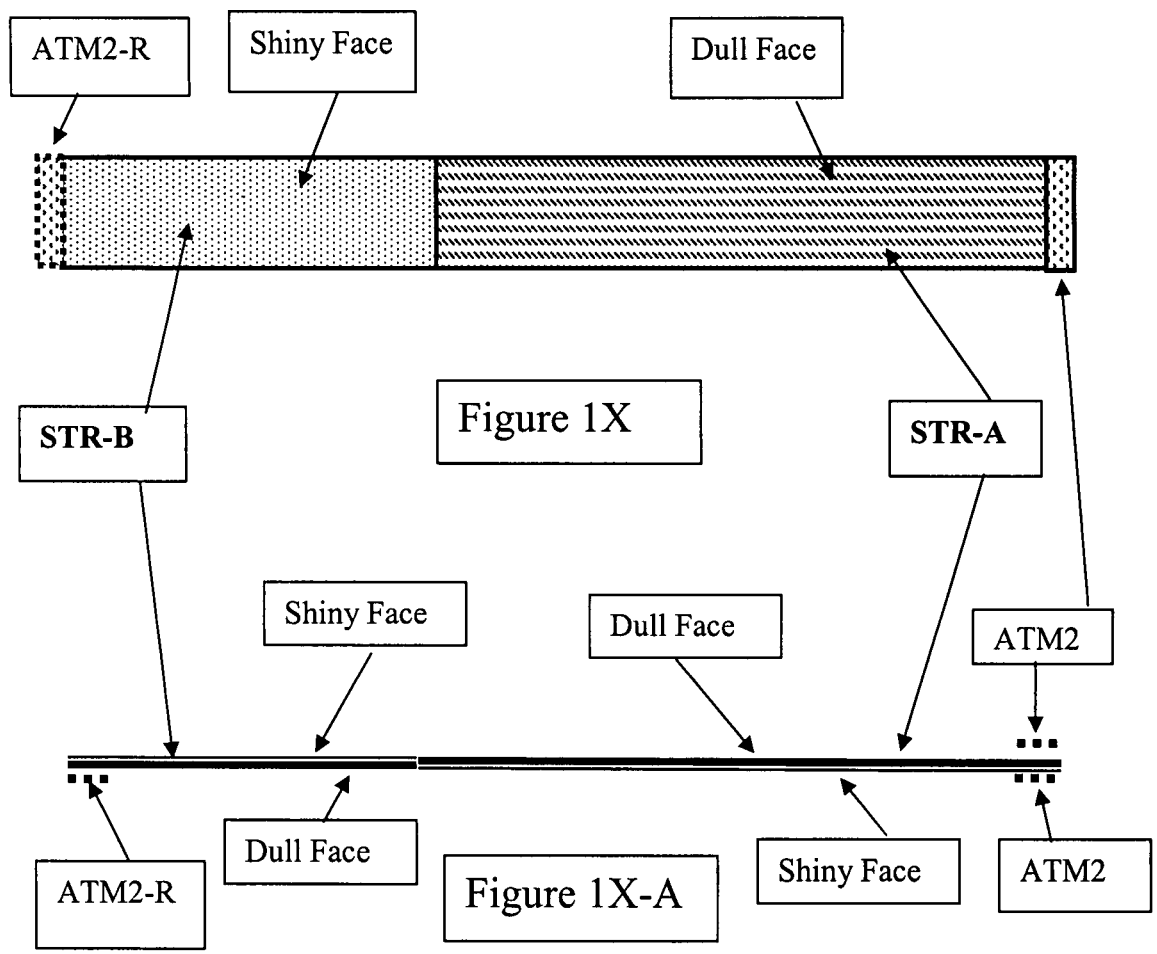
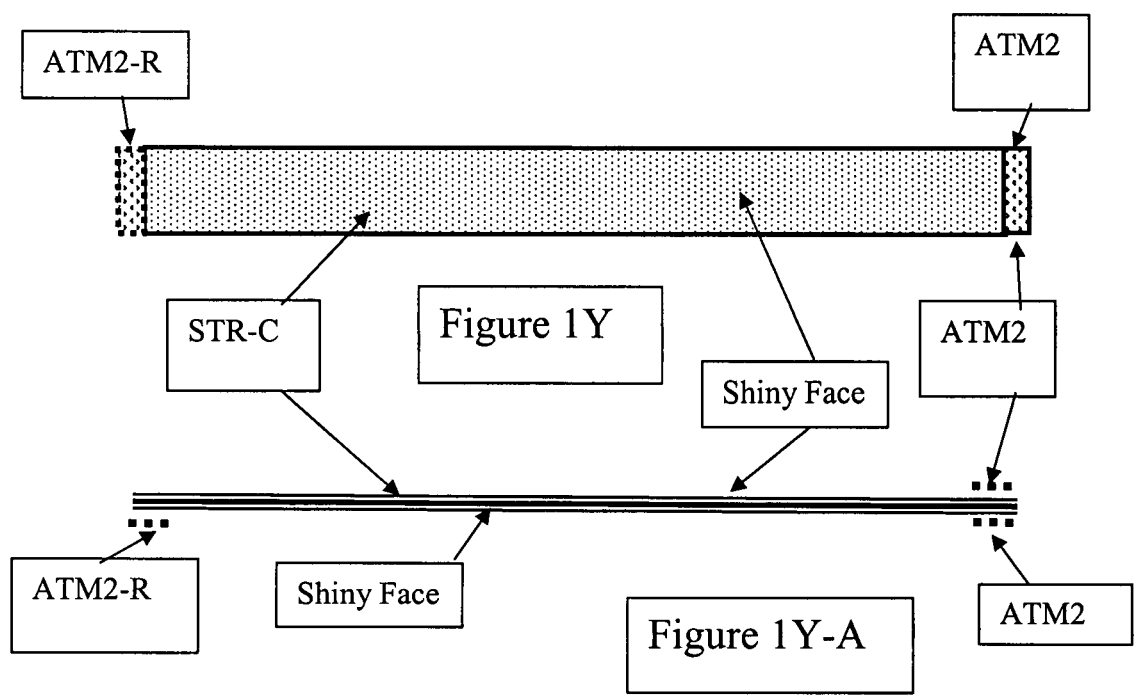

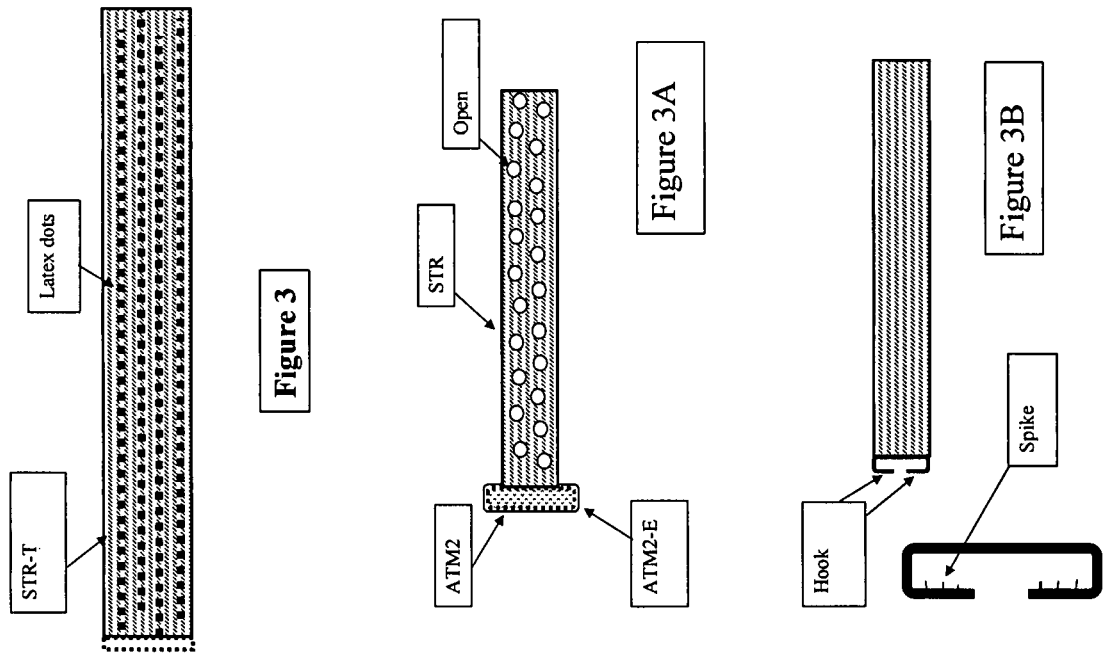
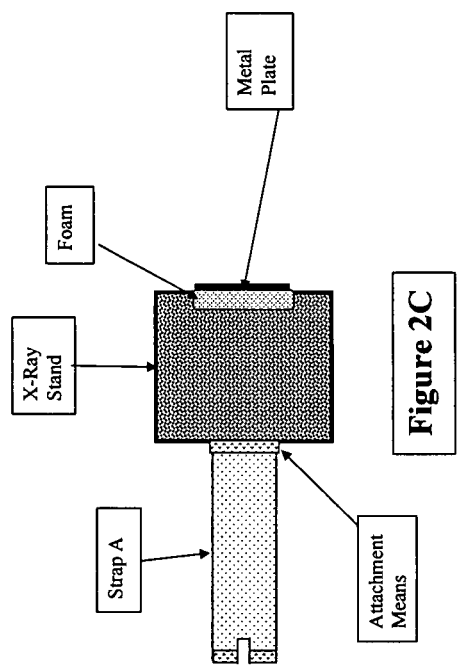

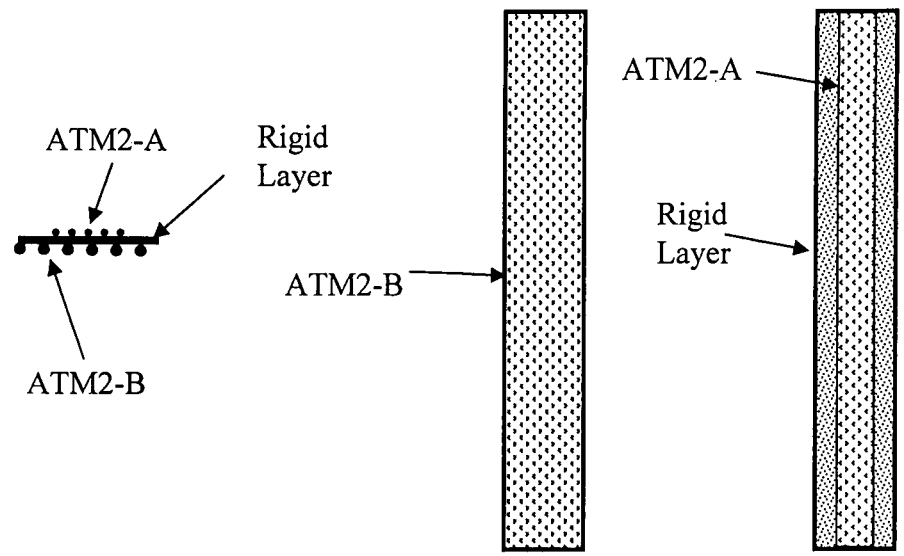
Figure 16B Figure 16A Figure 16
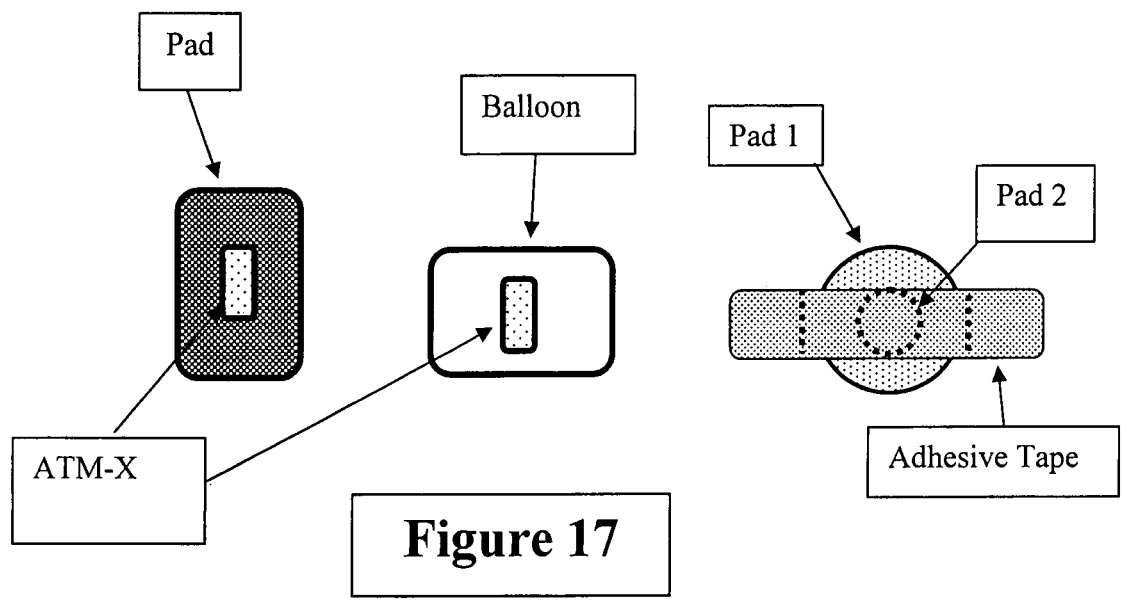
Figure 17

DANESHVAR WRAPPING MEANS II AND METHODS

This application incorporates by reference and claims the priority of the provisional application No. 60/771,819 filed on Feb. 10, 2006.

THE BACKGROUND OF THIS INVENTION

This invention is related to an improved version of the wound wrapping and support means for use in a living body. Wrapping a limb and application of compression to a limb is important in conditions such as control of varicose veins, limb swelling and post surgical status for the vessels or cosmetic surgery etc. However, to the knowledge of the applicant there is not a simple unit for providing such a help to the users. This application introduces models that are designed in solving such problems.

THE BRIEF EXPLANATION OF THE INVENTION

The new methods of support and compression of the limb, consist of an improved version of the models which this applicant has previously introduced to the USPTO. These units continue to utilize special stretchable fabric which functions as a loop fastener attachment means, thus it is capable of attaching to the hook fastener attachment means on a detachable, re-attachable basis. This strap means will be attached to a support means of various forms such as stable hook means, hose means, or a panty hose that has zones of hook fastener attachment means on or between these two units so that the strap means will wrap around the limb on oblique fashion while moving up and being pulled. So that finally the limb will be covered by the stretchable strap which is in a pulled condition. This provides tension in the strap, compression on the limb and will protect the underlying vessels and the tissue properly. Different straps or multiple straps may be used with this unit. Pad means may be also used with these units.

BRIEF EXPLANATION OF THE FIGURES

Please note that some parts of this invention are shown in different figures, for preventing a crowded figures. Please also note that many of the options shown in different figures can be combined to be used in a single model.

FIG. 1X. Shows a strap means made from two pieces Lycra™ with different faces and each having a zones, ATM2 on it.

FIG. 1XA. Shows the cross cut view of the a strap means shown at previous FIG. 1X.

FIG. 1Y. Shows a strap means made from a double sided lycra with two end pieces.

FIG. 1YA. Shows the cross cut view of the unit shown at FIG. 1YA.

FIG. 3. Shows a strap means that has dots of rubbery type material on it, to provide more powerful attachment of the straps.

FIG. 3A. Shows a strap means with holes in body and an oversized ATM2 at the end.

FIG. 3B. Shows a strap means, with special hook means at the end.

FIG. 4AB. Shows a strap similar to the STR-F from FIG. 4 in more details.

FIG. 16. Shows the front face of a double sided hook fastener attachment means, ATM2-DS.

FIG. 16A. Shows the rear face of the ATM2-DS shown at FIG. 16.

FIG. 16B. Shows the cross cut view of the ATM2-DS shown at FIG. 16.

FIG. 17. Show a pad means for use with these units.

DETAILED EXPLANATION OF THE FIGURES

FIG. 1X. Shows an elastic strap means which consists of two segments, STR-A and STR-B attached to each other, permanently or removably. The body of this strap means is made from a special fabric which the applicant found for use in this sort of strap means and has introduced it to the USPTO in his previous applications. This fabric is a stretchable, woven fabric made from Lycra™ with other materials such as Nylon or similar. The available Lycra™ fabric has a dull (non-shiny) surface opposite the shiny surface. In the course of his research the applicant noted that the shiny side of this material is capable of detachably/re-attachably, directly attaching to the support through detachable/re-attachable with the hook fastener attachment means, Velcro™, while being stretched. Thus he made supports with zones of the Velcro™ attachment means on the outer surface of the supports. Thus the attachment means on the support comprises a suitable hook-type material, such as Velcro™. Thus the straps made from this material is both stretchable and directly attachable and detachable to the hook, fastener zones of the support so that attachment can be made with different degree of stretching and different distances along the length of the strap, and without any special attachment device attached to the Lycra or the strap. Thus this strap not only is a stretchable fabric but also it functions as a loop fastener attachment means in one of its surface which has a shiny appearance. Therefore, any part of this strap means in the shiny side is capable in attaching directly to a matching hook fastener attachment means, ATM2, on a detachable/re-attachable basis.

This is a very important and useful property and makes this unit unique. It allows making the units explained in this application possible.

This strap has the property of conforming to the shape of the area, that is wrapped such as a limb and joint. It allows the air to go thorough which is important in allowing the sweat to descipate and area to be comfortable. It is a thin, non irritant fabric. Importantly, the applicant has made straps by sewing or attaching this fabric with having the shiny surface on both surfaces of the straps, shown at FIGS. 1Y and 1Y-A thus the newly made straps allow it to be attached to the hook fastener attachment means, ATM2 on a detachable, re-attachable basis, in both sides.

Figure 4:
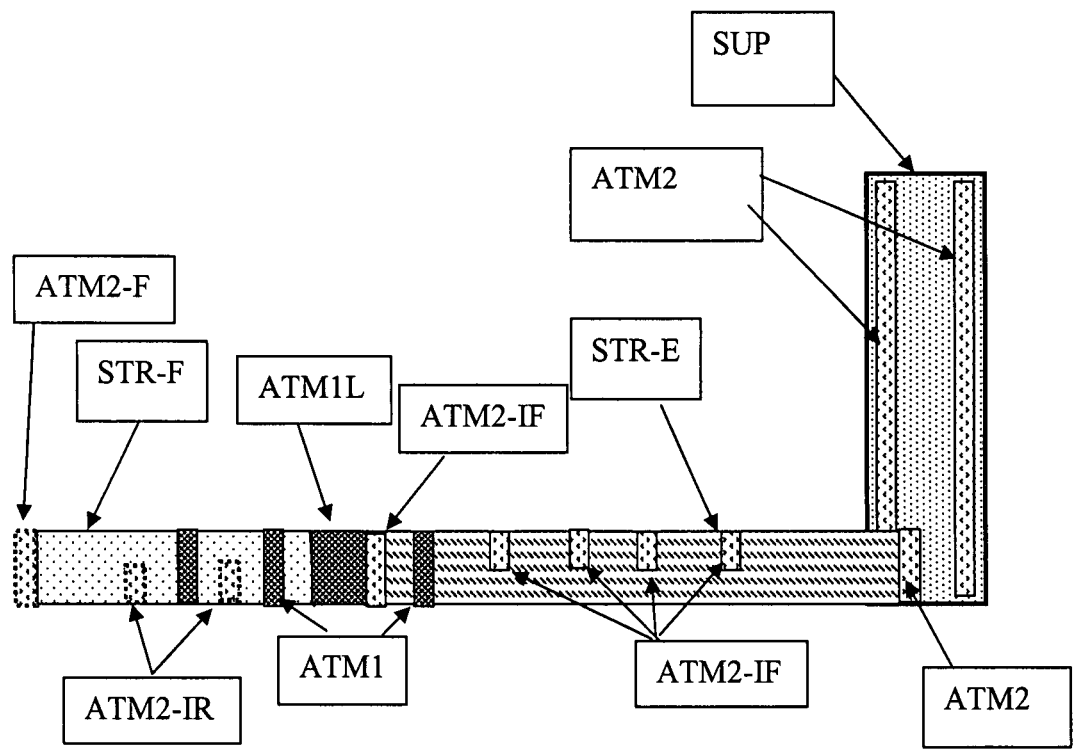
FIG. 4. Shows a strap-support means with a long strap with various zones of hook and loop attachment means on its front and back.
Figure 5:
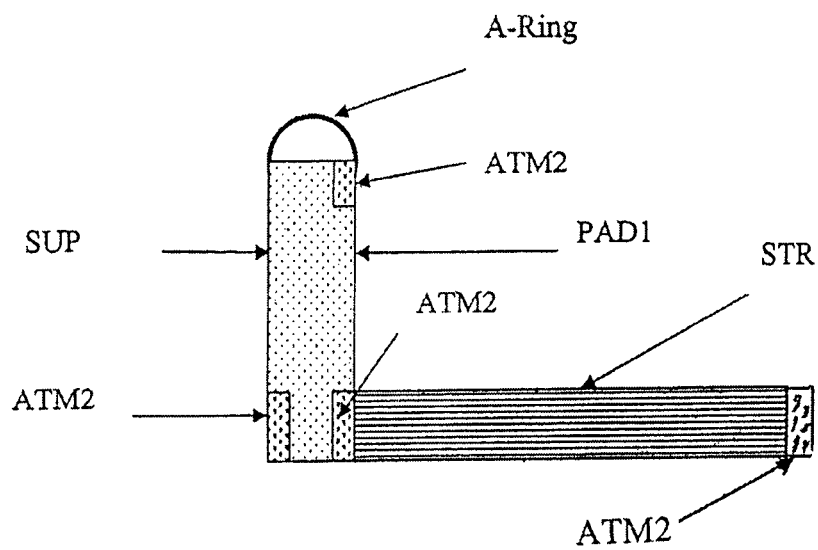
FIG. 5. Shows a strap means with a band means attached to its body for easy placement.

In the model shown in this figure the initial segment of the strap means, STR-A is chosen so that its outer surface has the dull face, Dull Face and its inner=rear surface has the shiny face. In contrast the second segment, STR-B has an outer surface which has a shiny surface, Shiny Face, thus its inner=rear surface will be dull. The outer surface of the initial end of the strap A, STR-A has a zone of hook fastener attachment means, ATM2 that allows the inner surface of the body of this segment, STR-A of this strap means to be attached to it after wrapping around the limb. The end of the strap A also has ATM2 in its lower=rear surface of the end as well which allows this unit to be attached to a support means as shown at FIGS. 4, 5 and similar.

The other end of this strap means at the end of the STR-B has a zone of hook fastener attachment means, ATM2-R on its rear surface. Thus it allows this end to attach to the outer surface of the second segment of this strap means, STR-B which has a shiny surface, on a detachable, re-attachable basis, after being wrapped on the limb. So that the end piece of this unit will be attached and on control. Importantly, a strap means may be made by attaching different segments to each other by use of the attachment means at the ends so that the final piece will have the desired length and properties.

Figure 1:
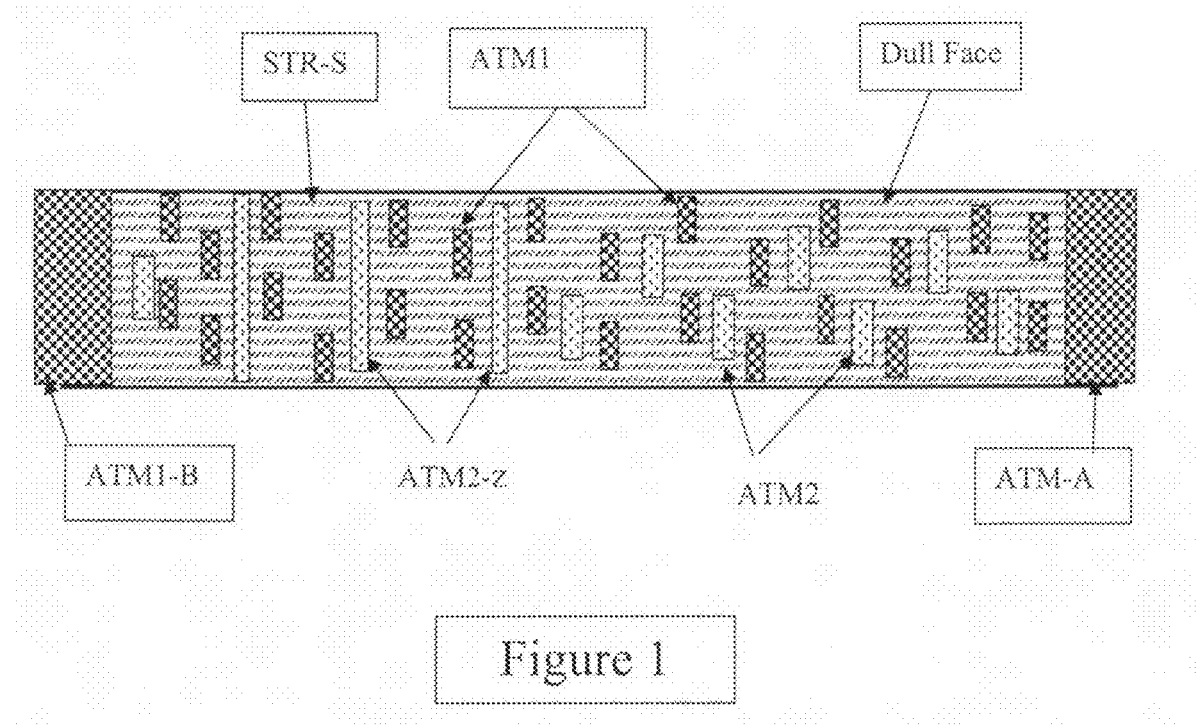
FIG. 1. Shows a strap means made from Lycra™ that has zones of attachment means, ATM1 and ATM2 on its outer surface.
Figure 1A:
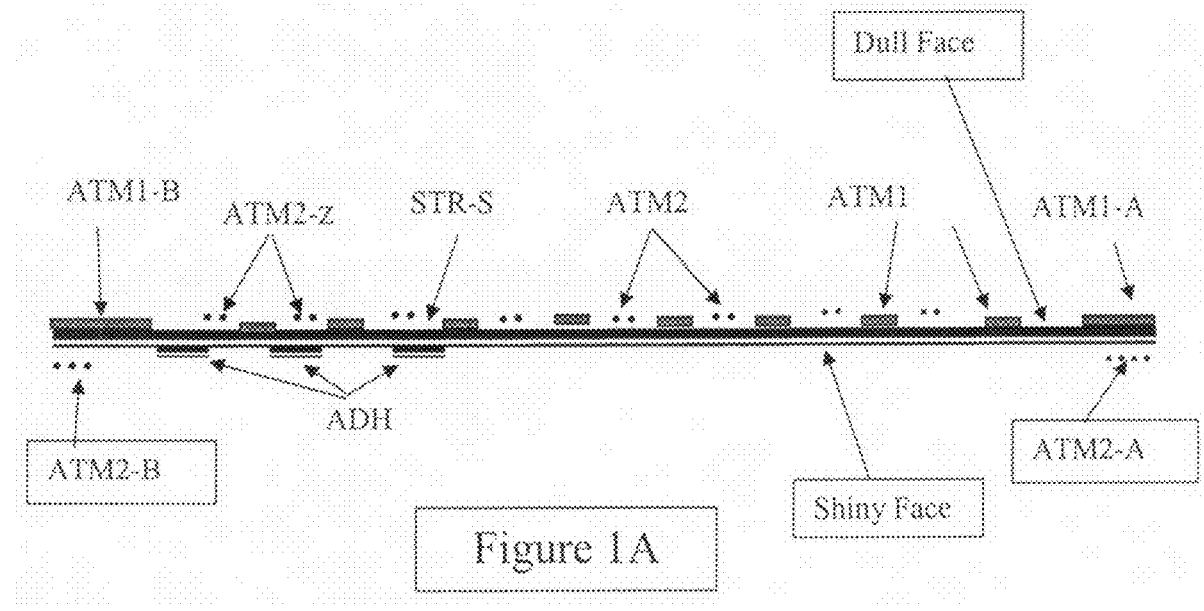
FIG. 1A. Shows the cross cut view of the a strap means shown at previous FIG. 1.

FIG. 1X-A. Shows schematically the cross cut, side view of the strap means, shown in FIG. 1X. In this figure the shiny face, Shiny Face of the strap A, STR-A is in the lower side and the dull face, Dull Face, on its upper surface. In contrast the second segment, STR-B has an upper surface which has a shiny surface, Shiny Face, and its lower face has the dull face, Dull Face. The zones of the hook fastener attachment means, ATM2, in the upper and lower as well as the zone of ATM2-R, in the lower are shown.

FIG. 1Y. Shows a strap means, STR-C which is a modified model with a shiny surface on its both front and rear surfaces. Thus it allows the attachment of a zone of hook fastener attachment means, ATM2 to its front and rear surfaces and on a detachable, re-attachable basis. Thus the end, ATM2-R of the strap means, STR-C will be capable to be attached to the outer surface of this strap in any area and on a detachable, re-attachable basis. The initial end of this strap means has a zone of hook fastener attachment means, ATM2 that allows the body of the initial segment of this strap means to be attached to it after wrapping around the limb. The inner or the lower surface of this strap has the zone of hook fastener attachment means in its rear surface shown at ATM2-R. Which allows the control of the end of this strap after being wrapped on the limb. So that the end piece of this unit will be attached and on control.

FIG. 1Y-A. Shows schematically the cross cut, side view of the strap means, STR-C, shown in FIG. 1Y. In this figure the body of the strap means has the shiny face, Shiny Face on both side, in the upper and lower sides. The zones of hook fastener attachment means, ATM2 and ATM2-R are shown with their locations.

Importantly, note that the strap means, can be used on a limb alone. While the unit can be utilized with more ease and functionality when it is used with a support means shown in the text.

FIG. 1. Shows a strap means STR-S made from a special fabric such as the Lycra™ explained in text, except in this model the strap means, STR-S, has zones of hook, ATM2 attachment means and loop, ATM1 fastener attachment means, on it's outer/dull surface shown at Dull Face. The dull surface has less power of attachment capability to the hook fastener attachment means, ATM2. This modification allows the following.

IA. The inner/rear=shiny surface of this strap means, STR-S shown more in FIG. 1A is capable of being directly attached to the zones of the ATM2 on a detachable, re-attachable basis. The presence of the zones of the ATM2 on the outer surface of this strap means provides the advantage of being more stable since the incoming strap attaches to such zones and it prevents the outer layer of the strap to slide over the underlying strap when the strap is wrapped on a limb. This prevents the strap from displacement and falling.

IB. Also outer/top=dull surface of this strap means, which is the dull face, Dull Face has zones of the loop fastener, attachment means, ATM1 on it so that allows the end of the strap means itself or the beginning of another similar strap which has zones of hook fastener attachment means, ATM2 to be attached to these zones on a detachable, re-attachable basis, in order to control the end of the strap.

Also both ends of this strap means may have a zone of loop fastener, attachment means, ATM1-A and ATM1-B on its upper/outer surfaces respectively and a zone of the hook fastener attachment means, ATM2-A and ATM2-B shown at FIG. 1A in its lower surface respectively. These zones allows the end of one strap to attach to these on a detachable, re-attachable basis.

Importantly, the strap may also have zones of adhesive means, ADH, that allows the strap to be adhered to the skin or to the underlying strap or other objects in order to add more stability and security.

FIG. 1A. Shows schematically the cross cut, side view of the strap means, STR-S shown in previous FIG. 1. In this figure the body of the strap means is shown at STR-S, the shiny face, Shiny Face of this strap means is in the lower=rear side and the dull face, Dull Face, the upper surface of this strap means has zones of both the loop fastener, attachment means, ATM1 and hook fastener attachment means, ATM2 on it. only few zone of ATM1 are marked. Importantly, this allows the end of the strap means, STR-S to attach to the loop fastener attachment means, ATM1 of the outer, surface of this strap when the strap is wrapped on a living body, also the inner/shiny surface of the strap means, STR-S to attach to the zones of the hook fastener attachment means, ATM2 located on the upper=outer surface of this strap on a detachable, re-attachable attachment basis, for making a very sturdy, stable attachment.

Both ends of this strap means have a zone of loop fastener, attachment means, ATM1-A and ATM1-B on its upper/outer surfaces respectively and also zones of hook fastener attachment means, ATM2-A and ATM2-B on its lower=inner surface of it respectively.

The zones of adhesive means shown at ADH on its lower/rear are also marked.

Figure 2:
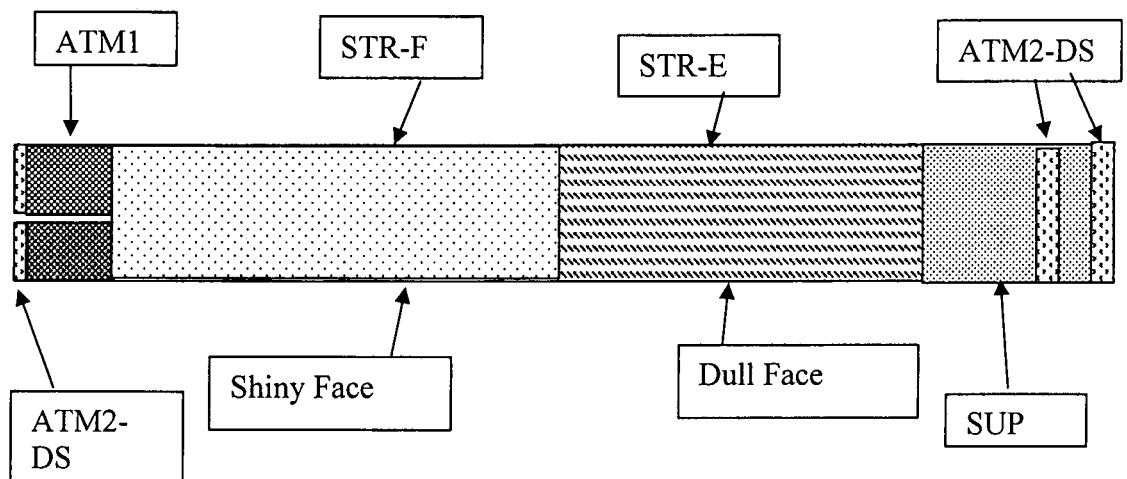
FIG. 2. Shows a strap means with two end pieces for special uses.

FIG. 2. Shows a strap means made from Lycra™, that has a support, SUP made from a laminate as explained in the text with zones of double side hook fastener attachment means, ATM2-DS attached to its front=outer surface. Imp, the strap means consist of two pieces:
a. An initial strap means, STR-E that its dull face is in front and shiny face on its rear.
b. A later strap means, STR-F that its shiny face is in front and dull face on its rear.

The end of this strap means, consists of the following.
1. It has a two pieces of end pieces attached to it which the outer surface of these end pieces have zone of loop fastener attachment means, ATM1 at its outer surface that allows the attachment of ATM2 to it if needed.
2. Each end of this strap means can be attached to the support means when needed.
3. The very end of these two end pieces has a piece of hook fastener attachment means, ATM2-DS which both the upper and the lower surfaces of this piece are ATM2. Thus it allows them to be attached to the outer surface of the support when needed. This unit can be used areas such as the females or males with large breasts that would stand on the way of procedures such as the isotope scanning of the heart and cause breast attenuation.

The method of use.
At the time of use for the isotope study
1. This unit will be wrapped around the chest of the patient in the breast area, so that the support will be approximately over the right breast of the patient.
2. The end piece of the strap means, ATM2 will be attached to the support and then will be adjusted so that it the support and strap means will compress the left breast of the patient and tighten so that the breast will move away and from the area of the procedure such as position of the left ventricle of the heart and also will flatten. So that it will keep the breast away from that area during the procedure. Alternatively, the support may be shaped and placed on the left breast in order to compress the breast as needed. The special body of this unit will allow an easy control of this unit and breast since one of the ends will keep the unit stable till the other end can be adjusted.

If the length is long it can wrap and its end pieces can be attached to the outer surface of the STR-F on a detachable re-attachable basis.

This unit also has use for holding the pendulous abdominal fat during procedures such as the cardiac catheterization and similar.

A shoulder strap may be used to pull the support or the strap upward and prevent it from falling.

Figure 2A:
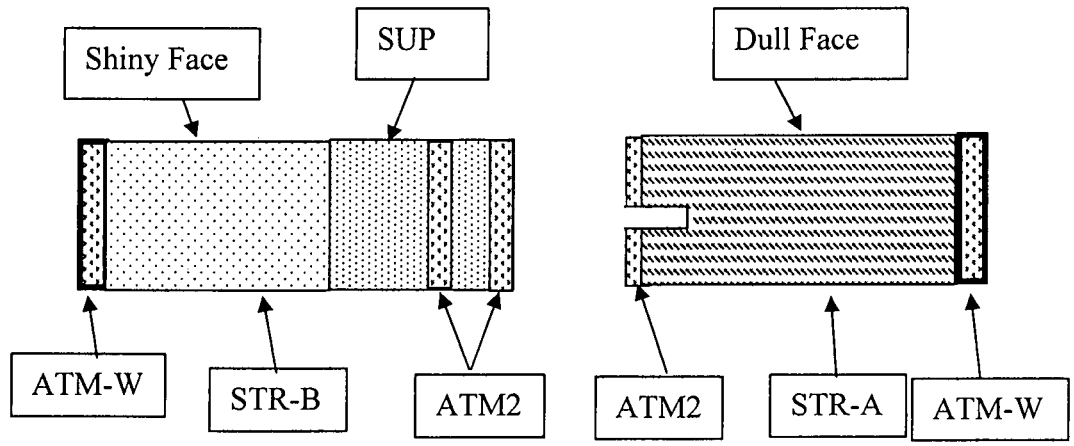
FIG. 2A. Shows a strap means consisting of two separate pieces for FIG. 2B. Shows two strap means in sides of a X-Ray stand to keep patient in position.

FIG. 2A. Shows a modified strap for holding patients for procedures such as taking X-Rays or similar which the body of the patient needs to stay in certain position for some time. In this model the strap means, STR-A and STR-B are made from two pieces of Lycra™, that has a means of attachment, ATM2-W which are designed to attach to the wall where the X-Ray film is positioned, the X-Ray table or similar on a detachable, re-attachable basis. The body of the strap, STR-B has shiny face, Shiny Face outside and also has a support means, SUP made from a laminate as explained in the text with zones of hook fastener attachment means, ATM2 on it. The strap means, STR-A has a dull face outside, Dull Face with a zone of hook fastener attachment means, ATM2 at the end of this strap means and a cut at the end.

This design allows the straps to be attached to the sides of the wall or the X-Ray table or the site which the X-Ray will be taken and to hold the patient as follows.

The method of use.
1. The patient stands on the wall or table in a proper position for taking the X-Ray or similar.
2. The technician will pull the straps and attach the strap A, STR-A to the support, SUP on detachable, re-attachable basis so that the strap means will keep the person in desired condition. If the length of the strap was long it can be pulled so that it's end pieces can be attached to the outer surface of the STR-B on a detachable re-attachable basis.
3. After the test the strap will be opened and patient can leave.

Importantly, this method allows the strap means to be washed or exchanged when needed.

Importantly, alternatively the strap means B, STR-B may be short so that the support will be the main part of this unit so that the strap A, STR-A can come from one site to attach to the attachment means of the support in the other side of the wall or table. The units can be made disposable.

Figure 2B:
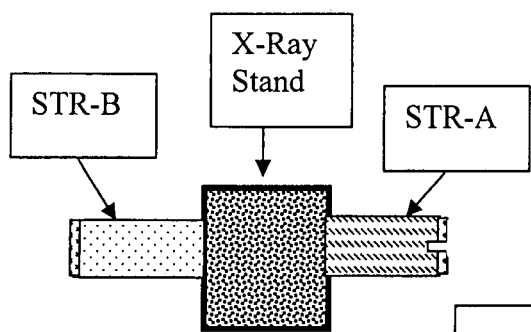
FIG. 2C. Shows a X-Ray with strap means, a metal plate and foam to keep patient in position.

FIG. 2B. Shows in miniature, the method which the two strap means, STR-A and STR-B shown in previous FIG. 2A can be used in sides of a X-Ray stand which commonly is fixed on the wall of the X-Ray room. In this method the place which the X-Ray film will be placed in referred as the X-Ray stand, X-Ray Stand and the straps are attached to it by a fixed or detachable re-attachable basis. The detachable method allows the strap to be exchanged for reasons such as being washed or exchanged.

The patient will be placed in to keep patient in position and also prevent it from falling. The unit may also use shaped foams and metal plates to be helpful in reaching these goal. A metal plate fixed on the side of the X-Ray stand can be a hinged one and this piece will prevent patient from moving out of the limit and the shaped foam will keep the body of the patient in exact position and prevent it from moving as well.

FIG. 2C. Shows a X-Ray stand which uses strap means, metal plate and foam for keeping patient in position. In this figure the place for taking X-Ray is shown at X-Ray Stand and a metal plate, Metal Plate is fixed to the proximity of this place either on its own border or on the wall by a fixed or detachable, re-attachable basis. So that the plate will function as a wall and prevent patient from moving further. A strap means, STR-A such as one shown in previous FIG. 2A is attached to the wall or the side of the X-Ray Stand, by a fixed or detachable re-attachable basis. So that the strap can be pulled over the body of the patient in order to attach to the Metal Plate or its vicinity on a detachable, re-attachable basis. A foam means, Foam or two foam will be used to keep patient further in position. This method allows the patient to be placed in the selected position and will prevent from moving and falling. FIG. 3. Shows a strap means made from Lycra™ except the body of this strap means, STR-T, has dots or zones, Latex dots of materials such as latex or rubbery, or other synthetic material that are raised or have raised parts that will function for preventing the overlaping strap to skid. These raised zones can be located on the one surface of strap and it will provide a sort of grip on the in-coming surface of the strap or fabric so that the combination will prevent them from sliding, or displacing easily. Importantly, these dots or zones can be only in one side or in both sides of this fabric.

This method is designed to provide the following advantages.

1. More stability to these units. So that one unit would not slide or skid over the other and will keep its position as it was placed initially.
2. It will not stick these straps to each other.
3. It may promote the attachment of these two straps.

In this figure this material is shown in the form of dots, Latex dots which is scattered all over, although they may be made in the form of lines of different shapes or patches. The thickness and the shape of these spots or means may wary and they may have a shape that will engage with each other when are in approximation or the contact of each other.

Importantly, instead of the latex dots the unit may have any other kind of means or materials that allows these two straps to be attached or adhered to each other on a detachable basis. These materials can be 1. A sticky material, such as gel or glue.
2. A series of microscopic pins that designed to engage with the body of the fabric but flat enough to avoid hurting the skin.
3. Any other materials.

This figure also shows that the strap has a series of openings, Open, that allow the air to go thorough for various reasons, ventilation, heat control etc.

The end of the strap also has a clip, Clip that allows it to engage with the strap and keep the end stable.

FIG. 3A shows a strap means that has an extended piece of hook fastener attachment means, ATM2-E in its end, with two ears that will be rolled back to attach to the rear surface of the strap, STR which is already on the limb and these two end pieces will attach and keep the end piece stable on the place.

FIG. 3B show a different snap at the end that will attach to the strap means already on the limb.

FIG. 4. This figure shows a very distinct wrapping system of a limb and a method of doing it which consist of a support, strap means similar to the main models discussed in the text. Except in this model the unit has.

1. A support means, SUP which is made from a long layer of either laminate or similar unit which has an outer cover=surface made from loop fastener attachment means here also mentioned as the ATM1. Also the outer surface of this support means, SUP has zones of hook fastener attachment means, ATM2 on it that allows the strap means, STR made from a material such as Lycra™ to be attached to it on a detachable, re-attachable basis. Also the end of the strap means, with ATM2 to be attached to it on a detachable, re-attachable basis means. These hook fastener attachment means, ATM2 can
1. From soft flexible material.
2. From a rather rigid material in its body in order to prevent the support from shrinking and bending.
3. From combinations of multiple small pieces of ATM2 that can be removed and attached.
4. Can be double sided hook fastener attachment means. So that one of their surface will attach to the outer surface of the support and the outer surface of them will be exposed to attach to the incoming strap means or similar.

Importantly, the body of the strap means, STR consist of two segments.

a. The initial=first segment of the strap means, STR-E which is attached to the support, SUP, is a long stretchable material made from the Lycra shown here at, STR-E. It has a shiny surface which is in the rear/lower side of this strap. So that this part will wrap around the limb and attach to the ATM2 of the support, SUP on a detachable, re-attachable basis. Importantly, the STR-E may have zones of hook fastener attachment means, on its front surface, ATM2-IF which allows the shiny surface of the strap to attach to these zones after the first wrap around the limb. Importantly, as shown in this figure such zones may be located only on the upper border of the strap, STR-E in order to prevent them from the zones of the ATM2 from being uncovered and to attach to the dress of the users. This will occur since the strap will be moving up from the ankle toward the knee.

b. A second segment, STR-F which is also made from a the special material Lycra as explained in the text, however, the shiny surface of this material is outside/in front so that the incoming end piece of this strap means which has zone of ATM2, marked at ATM2-F will attach to it on a detachable, re-attachable basis.

Importantly, the rear surface, dull surface of the segment STR-F may have zones of hook fastener attachment means, ATM2-IR in order to allow the upcoming part of this strap to be attached to these on a detachable, re-attachable basis. Importantly, as shown in this figure such zones may be located only on the lower border of the strap, STR-E in order to prevent them from being not covered and to attach to the dress of the users. Since the strap will be moving horizontally or somewhat down from the knee toward the knee.

Importantly, this strap means is long for being long enough to be wrapped around the leg, arm or another part of the body and to have its end piece to be attached to it by attachment means, ATM2 or any other means on a detachable, re-attachable basis, by one of following means.

1. Having the zones of attachment means such as loop fastener attachment means, ATM1 on the outer surface of the strap means so that the end piece of the strap which has hook fastener attachment means, ATM2-F to be attached to it on a detachable, re-attachable basis. An example of this is shown at zones of ATM1 at the outer surface of the end of the STR-E and also at the outer surface of the strap, STR-F. These zones allows the hook fastener attachment means, ATM2-F from the end of the strap STR-F to attach to one of these, which ever that matches its position on a detachable, re-attachable basis, and in a more durable basis.
2. Having a strap means made from double sided lycra, so that the hook attachment means at the end piece of the strap, ATM2-F to be attached to it on a detachable, re-attachable basis.
3. Having one segment of the strap, STR-E such as the initial part of the strap to have an outer surface of the lycra that has a shiny surface and allows the end piece of the strap, ATM2-F to be attached to it on a detachable, re-attachable basis.
4. The rest of the strap may have a segment such as STR-F which has an outer surface made from shinny surface of lycra or double sided lycra that allows the ATM2 to attach to it on a detachable, re-attachable basis.
5. Use of a complementary piece such as one shown at FIG. 4A.

6. Use of various snaps, some shown at this application at ???

The optional segment of loop fastener attachment means, ATM1 can play a very crucial role in allowing the end, ATM2-F of the strap means, STR-F to be attached to it on a detachable, re-attachable basis. Since the straps can be attached to different spots of this piece thus this allows the functional length of this segment to be decided so that the end ATM2-F will fit and attach to this segment and allow multiple detachment and re-attachment. Also it allows custom made units to be made for this purpose so that the end of the strap, ATM2-F will attach to this segment.

Also the zone of hook fastener attachment means, ATM2 on the ATM1 allows the body of the STR-F to be partially attached to it for some stability. The method of use.

In this method the user places the support means, SUP on the leg or arm in a suitable place and the strap can be in one end of the SUP or the other end. For example the support-strap means, will be placed on the lower leg close to the ankle and the user will wrap the strap around the leg obliquely to move up close to the knee while being pulled. In each wrap the inner surface of the strap will attach to the ATM2 of the SUP till the STR-F comes and the end of this segment will attach to it on a detachable, re-attachable basis.

The end of the strap shown at ATM2 made of hook fastener attachment means or similar unit has capability to attach to the outer surface of the strap on detachable, re-attachable basis.

The end piece of the strap, STR-F has an attachment means, ATM2-F which can be also as follows.
1. The rear surface of this attachment means to be, hook fastener attachment means, ATM2. And the front also to have a the same.
2. The rear surface of this attachment means to be the hook fastener attachment means, ATM2. And the front also to have a loop fastener attachment means, ATM1.
3. If the need comes the end of the complimentary piece, SUP-B shown at FIG. 4A will be attached to the end of the ATM2-F and its strap, STR-G will be wrapped to allow its end piece, ATM2-G to attach to the SUP-B. The D-ring located in this strap means, allows the length of the STR-G to be adjusted. So that the end piece ATM2-G will match the location of the SUP-B and will attach to it.

Importantly, the strap may use an adaptor that allows the strap to be delivered easily and also to be removed and re-applied easily.

Importantly, the zones of the hook fastener attachment means, ATM2 located on the support, SUP may be made by following the following methods.
1. A unit which is shown at FIGS. 16, 16A and 16 B. This unit has a rather rigid layer, Rigid Layer which has a front=outer layer with
   A. a larger zone of hook fastener attachment means, ATM2-B on its lower=rear surface that it can be attached to the outer surface of the support which has loop fastener attachment means on its surface.
   B. a narrower zone of hook fastener attachment means, ATM2-A on its front=upper surface so that the incoming strap means, STR can be attached to it on a detachable, re-attachable basis.

Importantly, the grip of these two hook fastener attachment means may vary to allow more grip for attaching to the support, SUP so that when the strap, STR is being pulled away this piece would not be dislodged.

Importantly, the body of the rigid layer will prevent the support from shrinking.

The use of hand hold applicators with these units.

Figures 18, 18A:
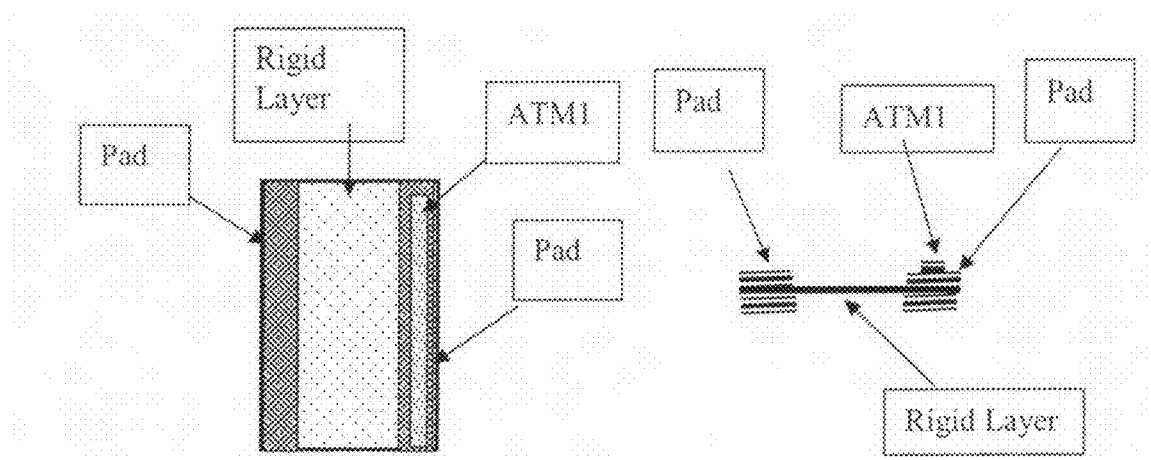
FIGS. 18 and 18A. Show a flat adaptor means for use with strap means.
Figure 19:
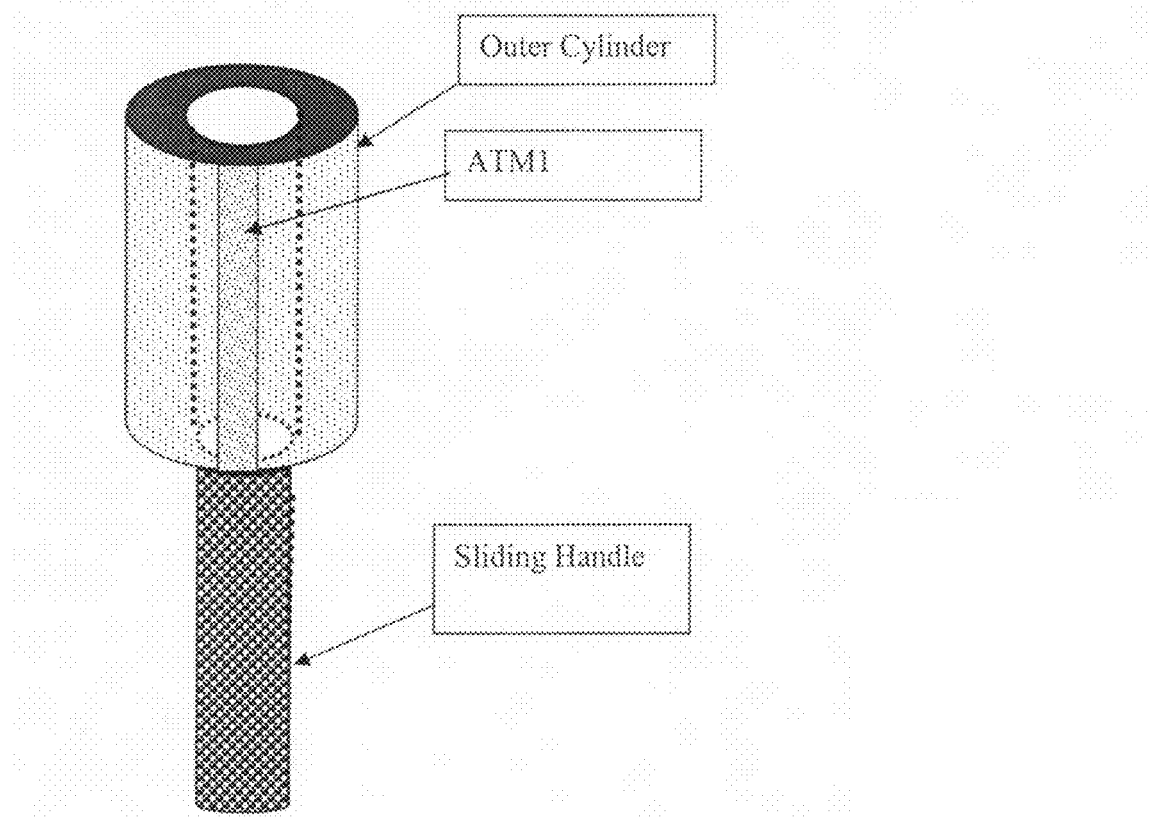
FIG. 19. Shows a cylindrical adaptor means for use with the strap means.

The applicant has designed a hand hold piece shown best at FIGS. 18, 18A and 19 so that it allows the strap to be applied to the limb and removed from the limb with ease. This hand hold piece may have different versions.
1. In one version the shown in FIGS. 18 and 18A the applicator consist of a rectangular shaped, rigid layer, Rigid Layer with a zone of loop fastener attachment means, ATM1 on it. Pieces of pads, Pad are placed in the sides of this unit to provide more body and grip to this unit. The zone of loop fastener attachment means, ATM1 may be on one or more of these pads or the body of pad may be made with an outer surface made of loop fastener attachment means, ATM1. This zone allows the end of the strap means STR-F from FIG. 7 which has a zone of ATM2 to be attached to it on detachable, re-attachable basis, and to be wrapped around it. At the time of storage the first free end of the strap, STR-F which has a zone of ATM2 will be attached to the body of this unit and the strap will be wrapped around the adaptor and will be hold in a compact secure condition. At the time of delivery the second or the free end of strap will be attached to the body of the support, SUP and the strap will be unwraped from this unit and wrapped around the limb till finally its end piece will be attached to the outer surface of the strap means.

In second model shown at FIG. 19 the hand held unit has a cylindrical, or cuboid shape body, Cylinder or rectangular cuboid piece with a handle, Handle. The outer surface of the body of this piece has a zone of loop fastener attachment means, ATM1 on it. Again this zone allows the end of the strap means STR-F which has a zone of ATM2 be attached to it on detachable, re-attachable basis. At the time of storage the first free end of the strap, STR-F which has ATM2 will be attached to the body of the adaptor and the strap will be wrapped around the adaptor and will be hold in a compact, controlled pattern. At the time of delivery the second or the free end of strap will be attached to the body of the support, SUP and the strap will be unwraped from the adaptor and wrapped around the limb, till finally its end piece will be attached to the outer surface of the strap means. The handle may be made to move and hide inside the body of this unit.

Importantly, the support means of this unit can be modified in order to extend from leg to the waist area in order to allow the strap means to move up and cover from the feet to the upper thigh area. One example of this method is shown at FIG. 4. In this model the body of the support means will be modified to be long with joints. The outer surface of the support means will be made from loop fastener attachment means, ATM1 to allow hook fastener attachment means, ATM2 to attach to it. Also it will have zones of hook fastener attachment means, ATM2 (not shown in that figure), in order to allow the strap to wrap around it and be held in place securely. The unit can be modified for use with multiple straps as well.

Figure 4A:
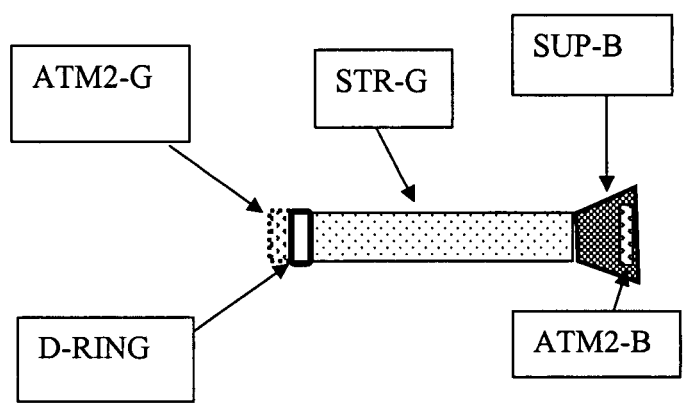
FIG. 4A. Shows an complimentary piece for the unit shown at previous FIG. 4.
Figure 4A:
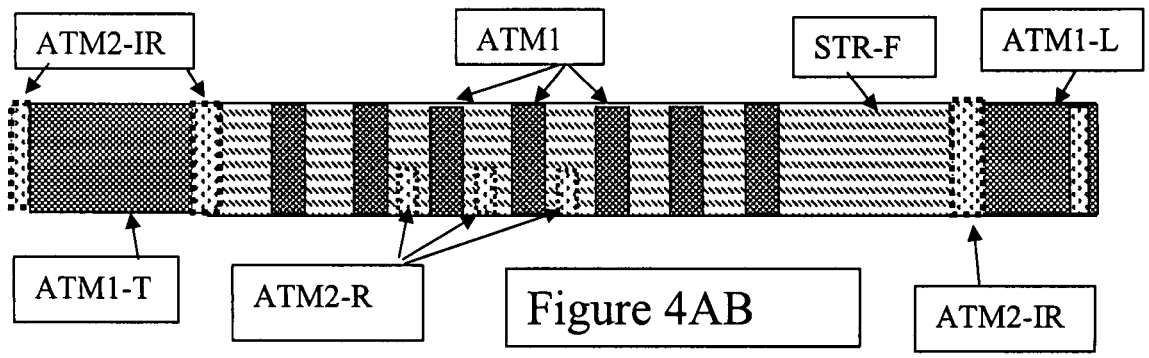

FIG. 4A. This figure shows a complimentary support, strap means, which is similar to the units shown in previous figure except.
1. The support means shown at SUP-B may have different shape such as trapezoid shape in order to transform the end piece of the strap, STR-F from the previous unit shown at FIG. 4 to a narrower strap means, STR-G shown in this figure. The end of the, STR-G has ATM2-G on its rear surface of the end. This strap means also may use an optional D-ring, D-RING to allow the length of the strap, STR-G to be adjusted and this end to be attached to the outer surface of the support, SUP-B after it wraps around the limb on a detachable, re-attachable basis.

2. Hook fastener attachment means, ATM2-B on the support allows the body of the strap to attach to it and be reasonably stable. This method allows the end of the strap means STR-F shown at FIG. 4 to be controlled easily.

FIG. 4AB. Shows schematically, a strap means similar to the STR-F which has a stretchable body made from Lycra™ that has two ends with zones of hook fastener attachment means, ATM2-IR at each side, that allows these ends to attach to the outer surface of a long zone of loop fastener attachment means, ATM1-L of another unit on a detachable re-attachable basis. This allows the point of attachment of the strap, STR-F to the ATM1-L to be decided in order to change the effective length of the ultimate unit. Thus by this method the final end of the strap means at the left side of the figure will be able to wrap around the limb and return and attach to the zone of ATM1-L on a detachable, re-attachable basis. This strap also has multiple zones of loop fastener attachment means, ATM1 on its outer surface so that the end piece of the strap, STR-F which has a zone of hook fastener attachment means, ATM2-IR on its rear surface to be able to attache to one of these zones on a detachable, re-attachable basis. Also of importance is the presence of hook fastener attachment means, ATM2-R located on the rear surface of this strap, that allows these zone to attach to the outer surface of the underlying surface of this strap on a detachable, re-attachable basis.

Figure 4B:
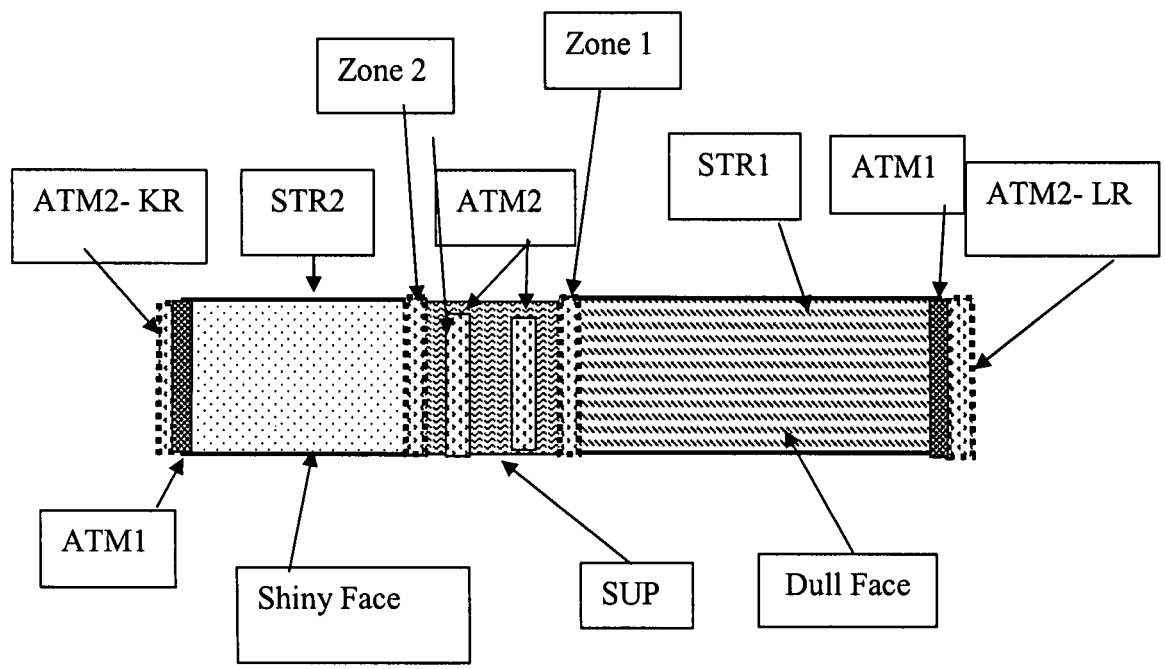
FIG. 4B. Shows a strap means with a piece of support between the straps means. One strap has dull face and the other shiny face in front.

FIG. 4B, shows a piece of support means, SUP which has an outer layer covered from loop fastener attachment means, ATM1 so that this body allows the following.
1. One strap, STR-1 to be attached to it on a detachable, re-attachable basis.
2. The support, SUP allows the body of the strap, STR-1 to attach to its attachment means, ATM2 after being wrapped on the limb.
3. To allow the length of the straps to be modified.
4. To allows the functional property of the outer sides of the strap means to be changed. IN a way that one strap such as STR1 can be attached to it with a Dull face in front and another strap, STR2 with a shiny face on it's front of the other end of the support.

Figure 4C:
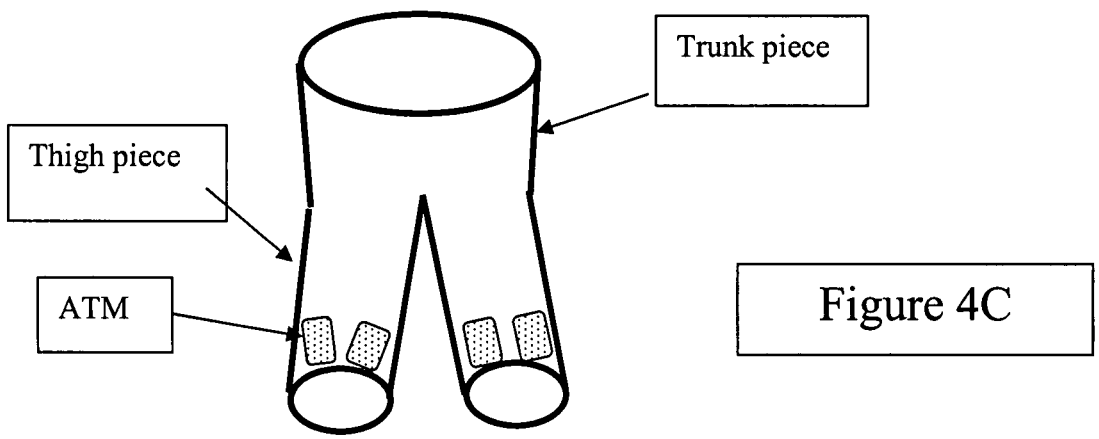
FIG. 4C. Shows a stretchable hose means with attachment means for the strap means to attach.

In this view the support, SUP is attached to the strap, STR1 that the front face of the lycra, Dull Face on a detachable, re-attachable basis, in zone 1. On the left side it is attached to the second strap, STR2 made from Lycra, shiny face in front, Shiny Face at zone 2, Zone 2 on detachable, re-attachable basis. The strap means have hook fastener attachment means, ATM2-KR and ATM2-LR on the rear surface of the their ends respectively. Importantly, the front surface of the end of these strap means may also have loop fastener attachment means, ATM1 on their outer/front surface to allow one end of a similar strap to be attached to it. Importantly, the size, shape and nature of the second strap means may var FIG. 4C. Shows symbolically a method of combining the strap-support means shown in FIG. 4 with other units for the purpose of making a complete system for covering from the foot to the thigh area. In this method the user will wear a stretchable hose system shown in this figure which is designed to have the capacity of compression of the thigh area, it can also extend to go over the knee area and to have the coverage of the knee as well. This system has attachment means, ATM on its outer surface designed for accepting the strap means or the support
means of the unit shown at FIG. 4. So that the combination will have the more adjustable compression of the legs which are more important due to the severity of the vascular problems and the higher hydrostatic pressure in this area. As well as the compression of the thigh and knee area. In this figure the trunk piece, Trunk piece is shown with the pieces for the thigh, Thigh piece with the attachment means, ATM shown on its outer surface.

Importantly, the unit may consist only from the leg support and the knee hose.

FIG. 5. Shows a support-strap means similar to the model shown at FIG. 4 except this unit has a means such as one shown at R-Ring that allows it to be placed in a finger so that with the use of the rest of the unit the body of the support can stand on the hand wrist area easily. This unit also has a pad means for use with it. This pad means is designed so that it allows it's thickness to be modified, by having another pad means attached to it on a detachable basis. The body of this support will stand on the lower part of the forearm and the wrist while these areas are exposed to a pressure when being placed on a desk or similar, during typing, being sited on the handle of the arm chairs or any condition that expose this area to the pressure. This support has a longitudinal body that functions as a padding means for preventing from the sensitive parts of the wrist from touching the adjacent objects. The outer surface of the support, SUP also marked as the pad means, PDA1, has a surface covered with loop fastener attachment means, ATM1 which allows the hook fastener attachment means, to be attached to it on a detachable, re-attachable basis. Also the support may have one or more zones of hook-fastener attachment means, ATM2, on it that allows the strap means, STR, to be attached to these zones after being wrapped around the wrist. In prototype model the body of the support, SUP is made from the laminate that was mentioned in the text with an outer layer from loop fastener attachment means, inner lining and a foam means sandwiched in between. Thus the surface of the pad, PAD1 is a layer of loop fastener attachment means. Importantly, in practical term the support, SUP and the pad means, PAD1 are the same in this prototype model and the support, SUP functions a pad means, PAD1.

One end of the strap, STR in this particular model also has a zone of double sided hook-fastener attachment means, ATM2, which allows
1. The strap, STR to be attached to the surface of the support, SUP or the pad means, PAD1 on a detachable/re-attachable basis.
2. The strap to wrap around the wrist and have the end of the strap, STR, to be attached to the outer zone of the strap on a detachable re-attachable basis. When the body of the strap means provides such chance.

The ring means, A-Ring for the support, SUP=pad means, is adjustable so that it can be placed around the middle finger or another one/s in order to keep the front end of the support, SUP or the pad, PAD1 in a stable position without allowing it to move. This ring means can be adjustable by having one end of it being fixed to the support and the other end of it being attached to the body of the support, SUP or the pad means, PAD1 on an adjustable basis. In this model a zone of double sided attachment means shown schematically at ATM2, allows such an attachment when the body of this ring is made from Lycra,™.

The body of this ring may be made from a stretchable material in this case a different attachment means will be used to allow the attachment to occur. Various ways may be used to make the length of this ring adjustable, such as.
a. The ring to be made from an elastic or stretchable material to allow its length to adjust during function. b. A non-elastic material that goes around a finger but its length does not change.
c. In both cases the length of the ring, A-Ring may be adjustable.

The body of the pad, PAD1 has an attachment means such as a strap, STR that is made from an stretchable material "Lycra.™". which functions as the loop-fastener attachment means, ATM1. The end of this piece has a zone of double sided hook-fastener attachment means, ATM2 as shown.

The protective pad means, PAD1 may be made to have an adjustable body by.
1. Making it from an inflatable balloon so that the degree of inflation to allow its thickness to be modified.
2. By making it from combinations of pads, having one pad such as PAD1 and having a second pad such as pad means, PAD2 to be attached it on a detachable/re-attachable basis. So that by attaching the extra pad means the thickness and the shape of the pad can be modified.

These pads may be attached to each other by use of hook and loop fastener attachment means, bands or any other kinds of attachment means. In this model the pad, PAD2 shown at FIG. 5A has a zone of attachment means shown at zone, ATM2 which allows it to be attached to the surface of the pad, PAD1 on a detachable re-attachable basis.

Importantly, the body of the first pad as shown in this figure at pad means PAD1 may be made from a laminated means which is shown at FIGS. I and II.

This pad means use support, SUP which again in this model is shown at PAD1 for protecting the lower elbow and the wrist from being hurt by the pressure from the landing object such as table or handle of a chair.

Figure 5A:
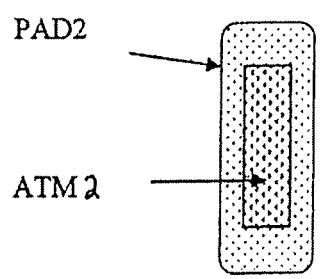
FIGS. 5A and 5B. Shows a pad means for use with the unit shown at FIG. 5.

FIG. 5A shows the front view of a second pad, PAD2 that has a zone of attachment means, ATM2 on its surface and this piece can be attached the surface of the support, SUP or the pad means, PAD1 on a detachable/re-attachable basis. The attachment of this piece to PAD1 allows the thickness and/or the shape of the PAD1 to be modified.

Figure 5B:
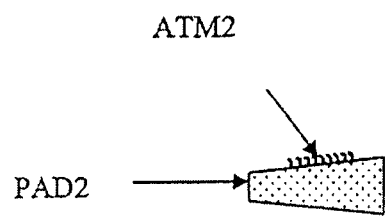

FIG. 5B shows the side view of a the pad, PAD2 shown at previous FIG. 5A. This figure shows that the shape of the pad can be different in order to allow different parts of the wrist to be protected more. Or the orientation of the wrist on the table to be adjusted. Also it shows the zone of the attachment means, ATM2 on its surface which allows this piece to be attached the surface of the pad, PAD1 on a detachable/re-attachable basis. The unexposed part of the hook fastener attachment means, ATM2, can be protected by a matching piece which will cover their surface.

Figure 6A:
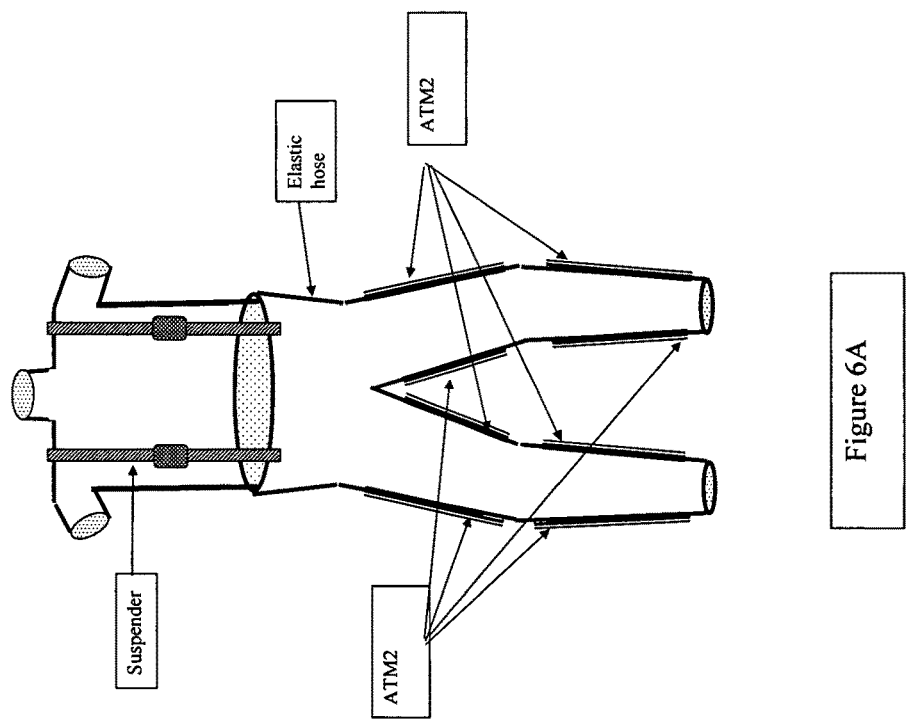
FIG. 6A. Shows a panty hose means with a suspender.
Figure 6:
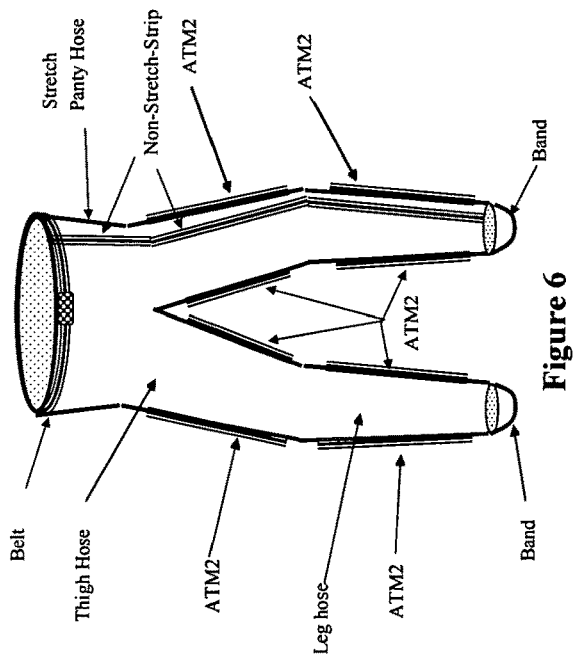
FIG. 6. Shows a stretchable panty hose means for use with long strap means.

FIG. 6. Shows symbolically a stretchable panty hose means, Stretch Panty Hose, designed to be worn from the waist to the feet area to cover the thigh, the knees, and ankle areas. It has a band, Band to prevent it from being pulled away from the foot. The body of this panty hose means has zones or strips of hook fastener attachment means, ATM2 in the sides which allows a strap means made from Lycra as explained in the text to be attached to it on a detachable, re-attachable basis. The hose or the panty hose may have one or more non stretchable strips, Non-Stretch-Strip on its for example, one in front, one in back and one in each side. So that the combination allows the hose to expand side wise but not to be pulled down from the belt or similar.

Importantly, this unit may be made with only some parts or the segments of the body such as a unit for the leg, a unit for the leg and knee, a unit for the thigh area only or a more complete unit to cover from the foot, leg, knee and thigh area and even the lower abdomen. A suspender system is designed as shown in FIG. 6A will prevent the body of hose from falling.

Importantly, the string or the band of a no-stretchable material, Non-Stretch-Strip, is embedded or attached to the body of the hose for preventing from shrinking or pulling the panty hose toward the feet. The belt system, Belt will prevent this line from moving down. Importantly, this non stretch string can be pulled to shorten and to match the height of the limb. The attachment spot of the non stretchable strip to the belt is adjustable to allows such change. Also it may be pulled from the foot side. The combination will prevent the strap means from moving down toward the feet and will be stable. The hose means has zones of hook fastener attachment means, ATM2 in the sides, laterally and medially as shown. This allows strap means, similar to the straps shown in the previous figures to be wrapped around along the hose means to cover the legs the knees and the thighs in order to provide a complete compression to the whole lower limbs.

Using this hose means with the strap means will allow the compression to be controlled and chosen as desired and the strap means will then apply most of the compression to the limbs.

FIG. 6A. Shows a unit, Stretch Panty Hose, similar to the unit shown at FIG. 6 except this figure shows the use of the suspender means, Suspender for preventing the panty house from falling.

Figure 7:
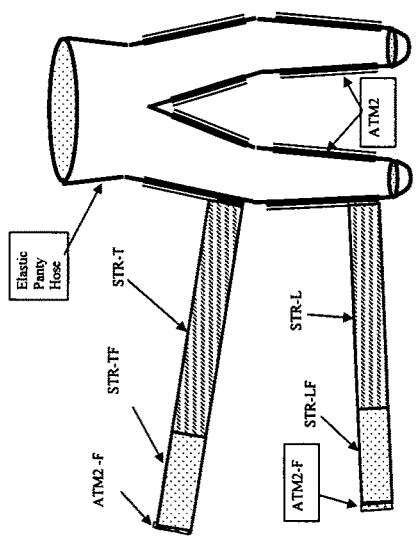
FIG. 7. Shows a panty hose means with two strap means attached to it.

FIG. 7 shows the method using an stretchable hose means shown in FIG. 6 with strap means. This combination is designed for keeping the strap means in place and preventing the strap means from dislocation and falling. The stretchable hose will be further intensified by use of a relatively rigid pieces as explained in the text which will hold the stretchable hose in stable position in the direction which is desired and prevent it from shrinking along a line, such as vertical lines/horizontal in sitting position or lying down.

The relatively rigid pieces can be attached or be embedded in the body of the hose means in the manner as the non-strechtable strip means. They will be a thin layers of material such as polymers that will be used with these units and may be attached to the outer surface of the hose means by attachment means. Examples of such units is shown at FIGS. 16, 16A and 16B. In this model a stretchable panty hose is unutilized which has means of attachment in its surface or body so that it allows the stretchable strap means to be wrapped around the limb and be hold by the panty hose in place in order to prevent the strap means from dislocation and falling. The panty hose has strings, bands or straps of non-stretchable material that will be embedded to be part of its body to prevent it from shrinking along the vertical line in standing thus it will prevent the strap means from moving down toward the feet. The strap means then will apply most of the compression to the limb.

In the model shown in this figure a long, stretchable, strap means, STR-L+STR-LF and STR-T+STR-TF attached to it. The strap means, STR-L attaches to the body of the panty hose in the ankle area and the user will wrap the strap around the leg obliquely and continues wrapping to move up close to knee or over the knee while pulling the strap means. In each wrap the inner surface of the strap will attach to the ATM2 of the panty hose till the end of the strap. The end of the strap shown at ATM2 is capable for attaching to the outer surface of the strap, STR-LF and STR-TF on detachable, re-attachable basis and keeps the end stable.

The end piece of the strap, STR-LF and STR-TF has an attachment means, ATM2 which can be also as follows.
1. The rear surface of this attachment means to be, hook fastener attachment means, ATM2. And the front also to have a the same.
2. The rear surface of this attachment means to be the hook fastener attachment means, ATM2. And the front also to have a loop fastener attachment means, ATM1. ?????????

3. Importantly, a unit similar to the unit shown at FIG. 4 ? which has the complimentary piece, SUP-B can be used so that it will attached to the end of the ATM2-F and its strap, STR-G will be wrapped to allow its end piece, ATM2-G to attach to the SUP-B. The D-ring will allow the length of the STR-G to be adjusted.

Importantly, the strap may use an adaptor that allows the strap to be delivered easily and also to be removed and re-applied easily.

Importantly, the zones of hook fastener attachment means, ATM2 located on the support, SUP may be made by following the following methods.

1. A rather rigid layer which has an outer layer with
   A. a zone of hook fastener attachment means, ATM2-Y in its rear/lower so that it can be attached to the outer surface of the support with loop fastener attachment means on its surface. B. a zone of hook fastener attachment means, ATM2-Z on its front/outer surface so that the incoming strap means, STR can be attached to it on a detachable, re-attachable basis.

Importantly, the grip of these two hook fastener attachment means may vary to allow more grip for attaching to the support, SUP so that when the strap, STR is being pulled away this piece would not be dislodged.

Figure 8:
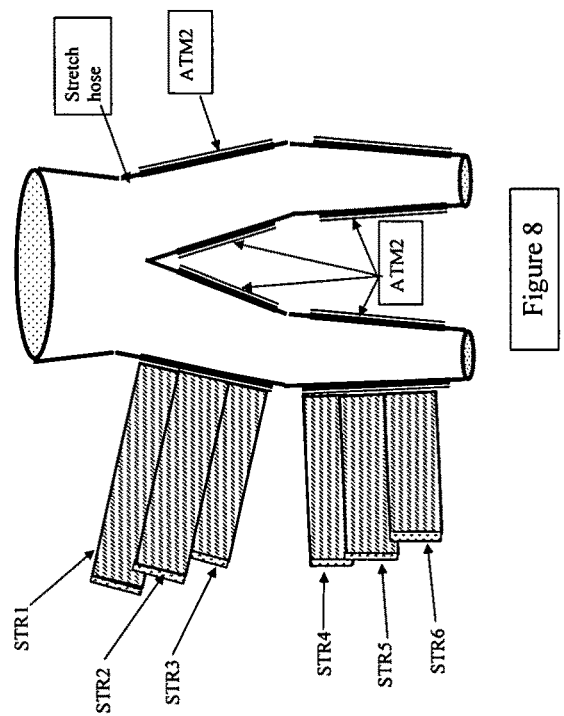
FIG. 8. Shows a panty hose means with multiple strap means attached to it.

FIG. 8. Shows symbolically the unit shown at FIG. 7 with a series of stretchable, strap means, STR1, STR2, STR3 . . . STR6. Which the three upper strap means, STR 1-3 are attached to the hose and its related attachment means for the thigh area and the three lower strap means, STR4-6 are attached to the leg area. This method allows these straps to wrap horizontally, to the limb and attach to the ATM2 zones of the panty hose on detachable, re-attachable basis. The design of these straps will allow the end piece to attach to the outer surface of each strap so that each strap will be secure. The end part of strap means may have a segment that is shiny as shown in previous figure.

Importantly, in some models the strap means may only go to half way of the hose and to attach to the hook fastener attachment means, ATM2 in the middle and then to return and attach to the rear surface of its own. Thus by pulling the attachment means to pull the front half of the hose means and to make the hose unit tight. The strap means will overlap each other in order to make a full coverage of the underlying limb.

Figure 9:
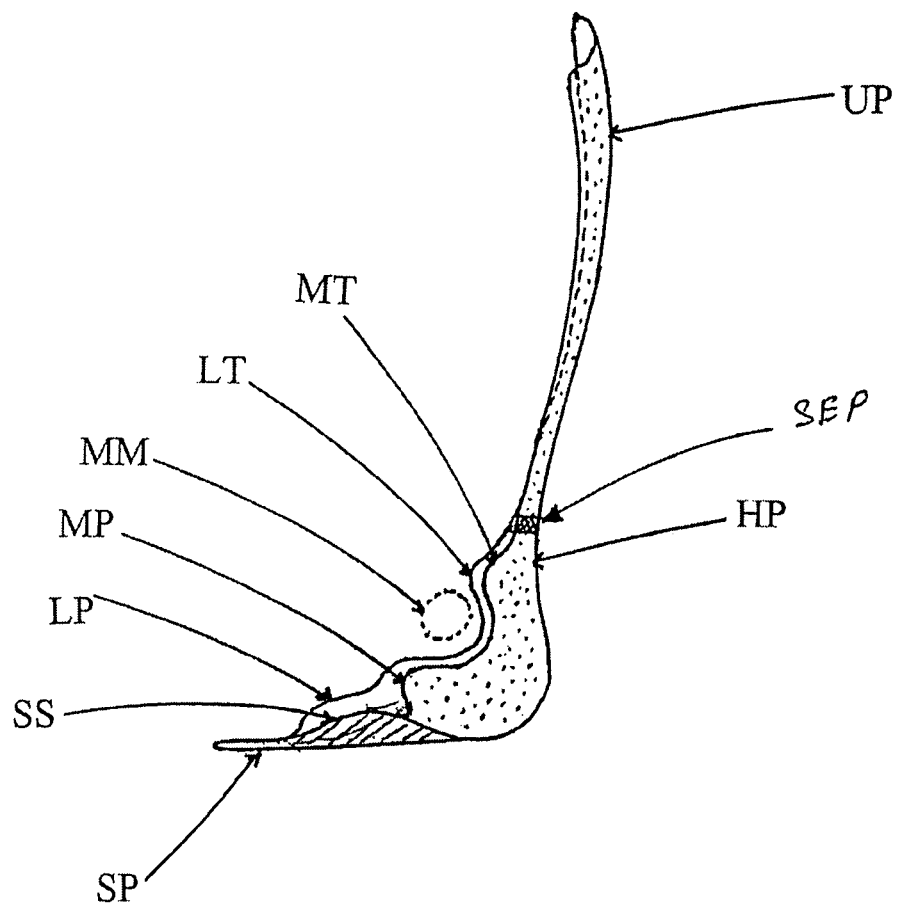
FIG. 9. Shows a special support for foot and leg.

FIG. 9. This figure shows schematically a support unit for the leg which consists of a relatively rigid but flexible support, which is shaped to stand on the leg, ankle and feet area. When in place this unit would not shorten, but would twist to the sides and also bend in ankle area to allow a joint function.

This unit can be a single piece or may consist from combination of two or more pieces. In this prototype model the unit consist of a leg piece and an ankle-foot piece that are attached to each other on a detachable/re-attachable basis at separation point, SEP. The purpose of this unit is to use this unit as a support means as mentioned in previous units for stabilizing the strap means and preventing them from moving and falling. Also to use the body of the support in an area such as ankle for compressing the soft tissues of the sole and ankle area and prevent the hydrostatic pressure to squeeze fluid out of the vessels into the tissue in this area. In this system the upper part of the support, UP has a curvature which matches the rear surface of the leg in the calf area. The support moves down attaches to the ankle-feet pieces and stands in the Achilles tendon area and then has flaps with special cuts and shapes that will fill the part of the ankle rear to the inner and outer malleolus area. Also in the sole area the inner/medial part of this unit has a curvature and padding that will fill the inner arch of the foot for supporting that part of the foot for two reasons.

1. For supporting the arch of the feet.
2. For supporting the soft tissue of the area in order to prevent from hydrostatic pressure to squeeze the fluid out of the vessels.
3. The ankle-foot piece also plays a crucial role in stabilizing this unit by preventing the leg support from sliding and moving down. This function come to be important particularly, when the shape of the leg of the person is so that the calf muscle are not prominent and do not bulge out in order to prevent from the upper strap for preventing the support from moving down.

Importantly, the support is designed to have a series of stretchable straps, attached to its body in one side and allow the stretchable straps to be pulled from one side of this support to attach to the other side on a detachable/re-attachable basis. In order to wrap around the leg for protection, compression an This unit will use a series of straps which will be attached to it or will go over this unit in order to provide the constriction and support of the tissue. The straps are not shown in this figure but in next figure.

In this figure the upper part has a curvature and shape shown at UP for matching and fitting the calf of the user. The part shown at HP is to stand on the Achilles tendon area. The medial and lateral flaps shown at MT and LT will stand on the area above the medial and lateral malleoluses. The flaps that stand in the area bellow the medial and lateral malleoluses are shown at MP and LP. The piece that stands under the arch of the sole is shown at SS and the sole piece shown at SP, which will stand under the sole area.

The prominent part of the malleolus is shown at MM.

Importantly, when in place and the straps are wrapped around the feet and lower leg, this unit will exert its power to compress and hold the soft tissues of the feet, ankle and lower leg by virtue of its own body and curvature, presence of lining and shaped pads.

Importantly, this support part of this unit may be made from combination of two or more pieces that can be detached and re-attached as desired. The connection between these can be with use of various methods, and the straps of each unit can be independent.

This system may support other units such as
1. Measurement means of various forms in order to allow the pressure in area to be known.
2. Electrical stimulators which can be placed in order to stimulate the nerves or muscles.
3. Wound dressing of various forms, gels, antibiotics, healing materials etc.
4. Wound support units of various forms.
5. Wound or tissue protectors of various forms, for prevention of problems.
6. Air pumps in order to allow the pressure to be modified in any form. The support of these units may be also further enhanced by the use of the layers for protection of the tissues.

Importantly, The use of these straps for the support of knee and other lower joint will have a suspender that will be attached to a belt and this belt will allow the knee support to be hold in place without using the constricting effect of the straps which can cause strangulation of the tissue and limb and complications.

Figure 10:
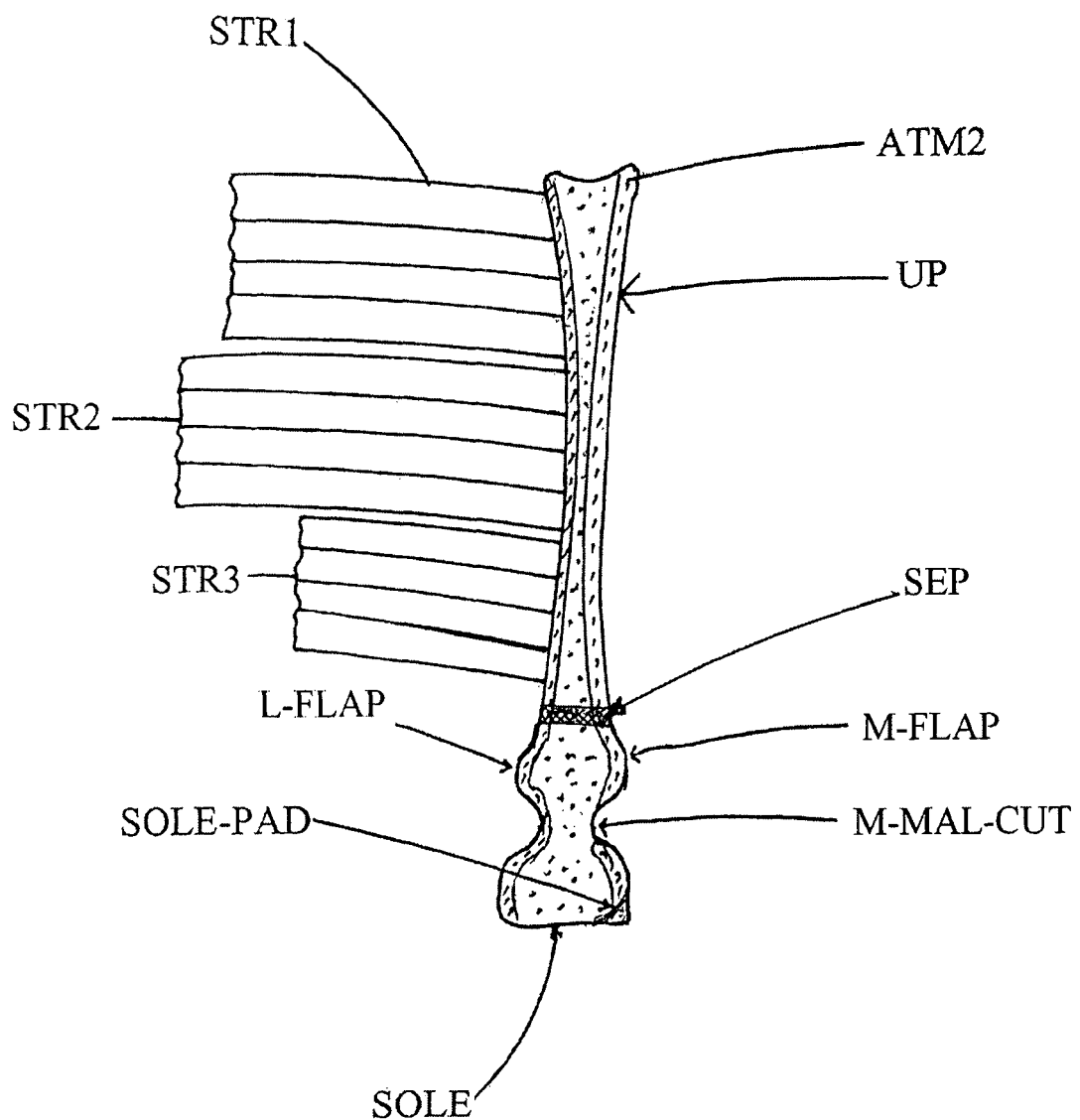
FIG. 10. Shows a support means, for the foot and leg with straps attached to it.

FIG. 10. Shows schematically the front view of the support unit shown at previous FIG. 9. In this figure the upper part is shown at UP. The lower piece in the bottom of the figure and the j separation point between these two pieces at SEP. The support moves down and reaches the ankle piece and shows it's two flaps, lateral flap, L-FLAP and the medial flap, M-FLAP. These flaps will be pulled by the stretchable straps (the stretchable straps for this part is not shown at this figure) to be attached to the other flap, above the internal and external Malleolus. The part that stands on the Achilles tendon area is seen. Then the lower flaps are shown, the sole part is shown at SOLE and it has the raised part that will fill the curvature of the arc of the sole as shown at SOLE-PAD.

This unit will use a series of straps which will be attached to it or will wrap around over this unit in order to provide the constriction and support of the tissue. In this FIG. 3 straps, STR1, STR2 and STR3 attaches to one side of support on a fixed base then are sized to wrap around the leg and attach to a zone of attachment means ATM2 on this support on a detachable/re-attachable basis. Importantly, the unit will also use similar stretchable straps that will attach to the malleolus and the feet part of this unit, being fixed on one side of the support going to attache on the other side of the support on a detachable, re-attachable basis. These straps are not shown in this figure.

Figure 15:
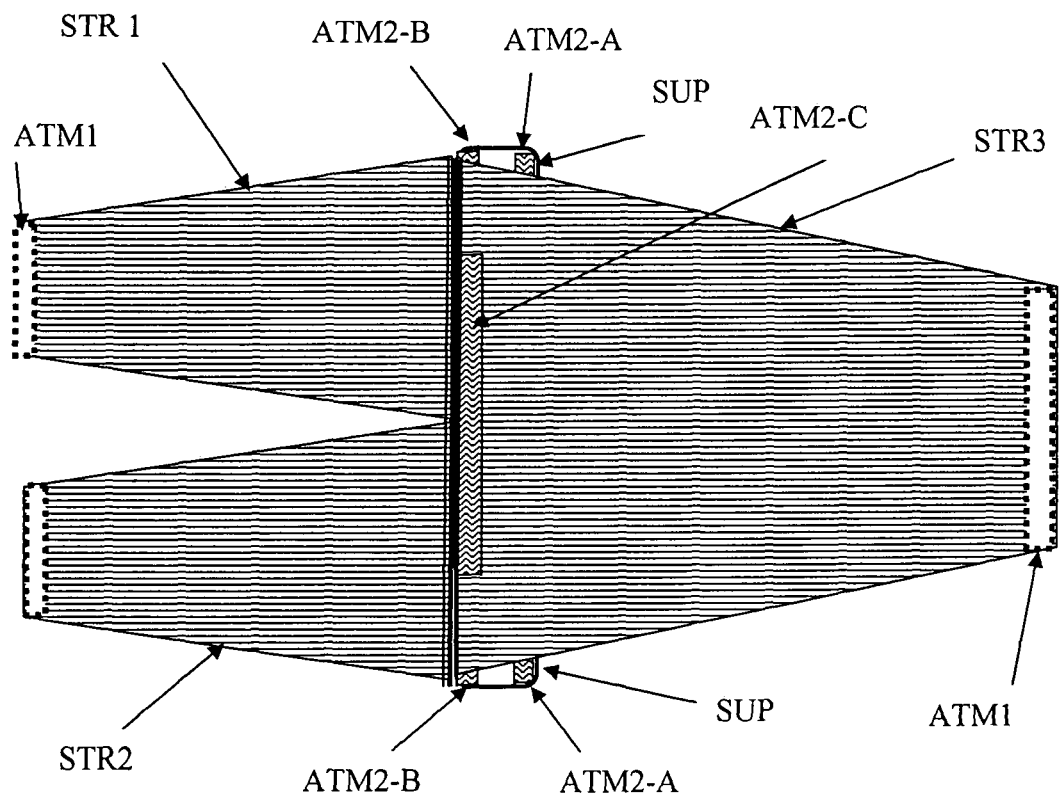
FIG. 15. Show a support means with wide strap means attached to it.

Importantly, the sizes and the shapes of the straps will vary in order to serve the purpose in a more meaningful fashion, for example the strap, STR2 may have a wider size in order to overlap the straps, STR1 and STR3. Also the straps, STR1, STR2 and STR3 may also have triangular shapes as shown at FIG. 15 in order to overlap each other and prevent from having a portion of the leg uncovered and bulged out.

This design is very important, since it makes a stretchable fabric means which will overlap each other and prevent from having a portion of the leg uncovered to bulge out. The problem is that an uncovered area of the leg, thigh or similar place can create a functional problem when one portion of a vessel such as vein is pressed and the portion before that is not covered. Thus the uncovered segment of the vein will engorge, the blood inside it to be stagnant and it will set a condition for the blood clot formation and phlebitis which will are very dangerous.

The straps not only will cover the ankle area but also the feet over the important vessels in order to allow a continuous compression from the feet, ankle and leg area which can be continued to also cover the knee and the thigh area for a complete coverage.

Figure 11:
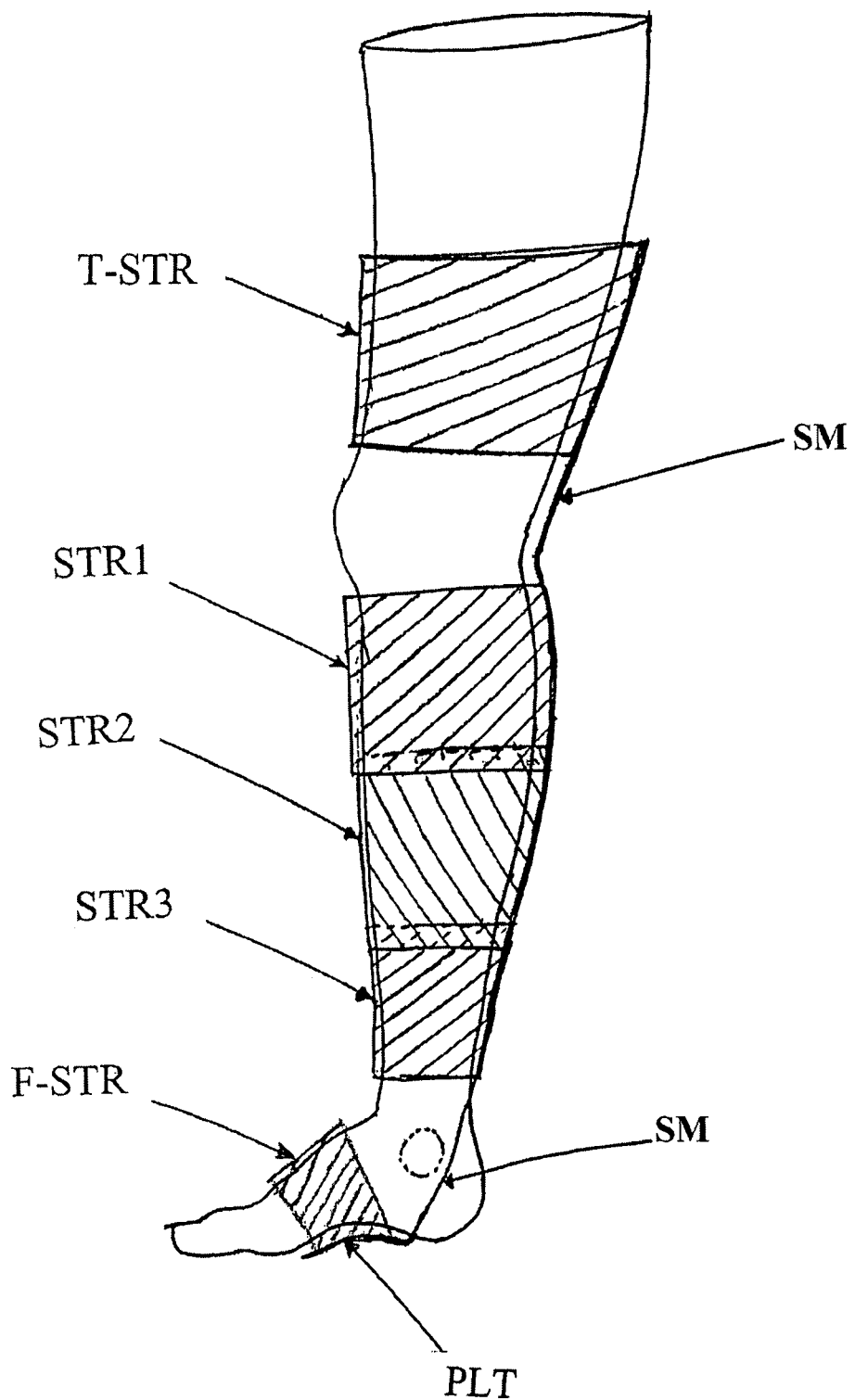
FIG. 11. Shows a more extensive support means for supporting the strap means from foot to the upper thigh with straps attached to it.

FIG. 11. Shows schematically a somewhat different method of supporting mechanism, designed to prevent from the sliding and falling of the strap means from the thigh and legs. In this method again a relatively rigid but flexible support means, SM which dose not shorten in its length but it can bend to some degree, would allow the unit to bent at popliteal area but would not allow the straps to move down toward the feet. This unit is shaped to stand in the rear surface or the sides of the thigh and would move down the leg, then will turn to move in the ankle area to connect to a plate, PLT that stands in the sole of the foot. By this method this support means will not be able to move down since the plate, PLT will prevent from doing such. A series of stretchable straps means are connected to the support means, SM in the following fashion.

1. A thigh strap, T-STR will wrap around the lower thigh, this strap can not move down due to the function of the support means, SM
   also due to the presence of the prominence of the knee cap. This strap means can be more than one strap and consist from three or more.
2. An upper leg strap means, STR1 which will wrap around the upper leg. This strap means will not be able to move down due to the connection to the support means, SM and the function of the support means, SM also due to the presence of the prominence of the calf muscle.
3. A mid leg strap means, STR2 which will wrap around the middle leg. This strap means can not move down due to the connection to the support means.
4. A lower leg strap means, STR3 which will wrap around the lower leg. This strap means can not move down due to the connection to the support means.
5. Importantly, the plate will be kept in place due to the use of strap means of its own, such as the foot strap, F-STR. This method will be quite useful in keeping the strap means in place from the thigh area to the leg.

Also importantly, this figure is to illustrate clearly that the strap means can overlap each other which is very important issue in preventing the a portion of the leg, thigh to be unprotected.

Importantly, the unit will be functional in most of the cases even if the support means did not extend to the feet, since the prominence of the ankle by itself will prevent from the leg unit and the support to move down.

Figure 12:
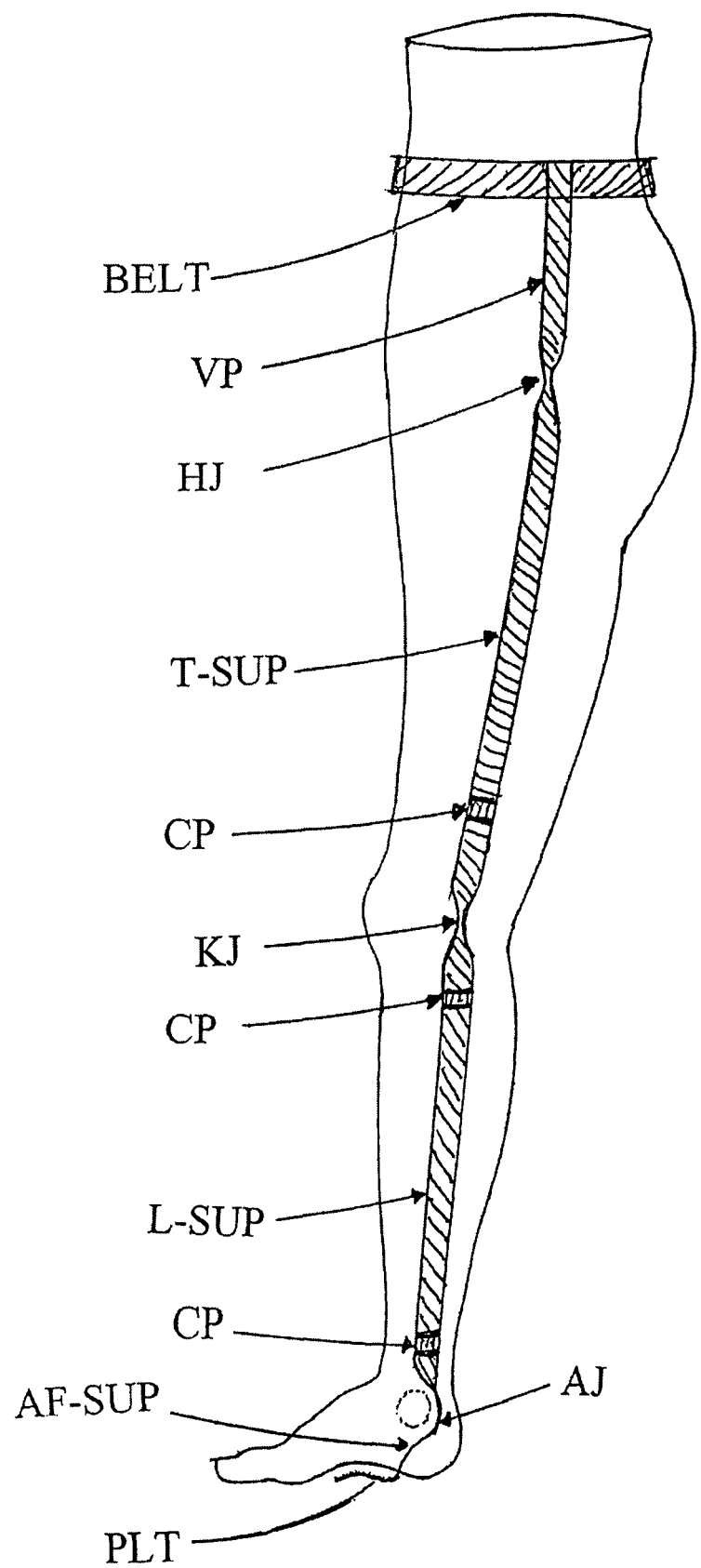
FIG. 12. Shows a support means from belt area to foot.

FIG. 12. This figure shows schematically a support mechanism which is designed to support the strap means in the thigh, leg and ankle-feet area. In this model the unit consist of 1. A belt means, BELT made from a non-stretchable material which stands in the belt area and allows a vertical piece, VP to be attached to it on a detachable/re-attachable and adjustable basis. The belt means, BELT will prevent the vertical piece, VP from moving down.
   due to the natural function of the belt in this area and presence of the bones.
2. A vertical piece, VP made from a non-stretchable material which moves down from the belt, BELT and attaches to the joint means at hip area, HJ and attaches to the support means for the thigh, T-SUP. This piece will prevent the thigh support, T-SUP from moving down. Since the belt means, BELT will not allow. Thus the hip joint means, HJ stands between the vertical piece, VP and the thigh support, T-SUP.
3. A thigh support, T-SUP which is made from a relatively, non-stretchable material which functions as the support means in the
   thigh area and will move down from the piece for the hip joint, HJ and attach to a joint means in the knee joint area, KJ. This support, T-SUP allows multiple strap means to be attached to it on a detachable/re-attachable basis. The T-SUP will prevent the leg support, L-SUP from moving down, due to its attachment to the belt mean, BELT, by use of VP.
4. A leg support, L-SUP which is made from a relatively, non-stretchable material which will function as the support piece in the leg area and moves down from the joint means for the knee joint, KJ and attaches to the ankle-feet piece in ankle joint area, AJ. This support, L-SUP allows multiple strap means to be attached to it on a detachable/re-attachable basis. This piece will keep the straps in stable condition and prevent them from moving down, due to its attachment to the belt mean, BELT, by use of VP and the thigh support, T-SUP.
5. An ankle-feet support, AF-SUP made from a relatively, non-stretchable, and shaped material as explained earlier in this application and this unit will prevent the leg support, L-SUP from moving down. The shape of ankle-feet support, AF-SUP matches the shape of the anatomy of the area and it stands in the ankle-foot area and move down to the sole area and will be kept in place by use of series of strap means not shown here. These strap means not only will hold this piece in place but also will compress the soft tissue of the ankle-feet area.

6. Importantly, a series of functional joint means such as the HJ, KJ and AJ are utilized in this unit in order to allow the upper and lower pieces to rotate in these joints. These joint means can be a spring means, a relatively, thin polymer or any other means that can be utilized in these areas that allows the unit to be held yet to function as a joint.

7. A series of connection means such as CP are designed to allow the two pieces of the supports to be attached to each other on a detachable/re-attachable basis.

This allows only one support or more to be utilized if needed.

Importantly, the unit will be functional even if the support means did not have the ankle foot support, AF-SUP, since the connection to the belt means, BELT will prevent from the supports to move down.]

Figure 13:
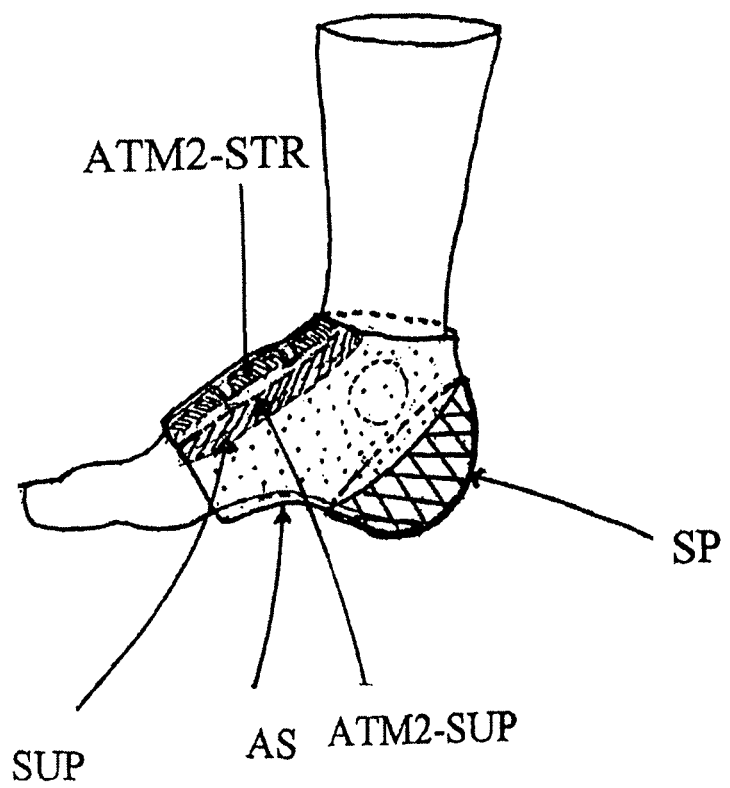
FIG. 13. Shows an ankle support.

FIG. 13. Shows schematically a support means designed for wound dressing of the ankle area. This unit is a modified version of a unit which is shown in this application for the wound dressing of the ankle and consists of.

1. A support means, SUP designed to stand in front of the very lower leg and/or the upper part of the ankle and upper part of the foot as shown. The support means, SUP is made from a non-stretchable layer similar to the supports which are explained in this application previously. In this prototype model the support, SUP is made from a laminate, with a surface made from ATM1 that allows the hook fastener attachment means, ATM2, to be attached to it on detachable/re-attachable basis. A soft lining for being placed on the skin or cover of a wound and a layer of a foam sandwiched in between as it is explained more in this application.

The support means, SUP, has a rectangular shape, has a long, narrow zone of hook fastener attachment means, ATM2-SUP on its border that allows a strap made from Lycra,™ or a zone of loop fastener attachment means to be attached to it on detachable, re-attachable basis.

Also Importantly, the end of the strap, has a zones of hook fastener attachment means, ATM2-STR that attaches to the outer surface of support, SUP, on a detachable/re-attachable basis. Please note that in this model the support, SUP is made from a laminate, with a surface made from ATM1 that allows the hook fastener attachment means, ATM2, to be attached to it on detachable/re-attachable basis. The end of the strap means, ATM2-STR is cut to function as tongues, here the unit has 3 such tongues, that allows each one to be pulled and attached to the out surface of the support, SUP, independently, which makes the adjustment easy.

Importantly, this method will make a double attachment means that allows a very unique and stable attachment of the strap, STR, to the support, SUP, on a detachable/re-attachable basis and makes the attachment of the strap to support far more easy.

2. A rather wide strap means, AS, made from an stretchable fabric, LYCRA™, which is shaped and sized to conform around the ankle and attach to the support, SUP, by use of a zone of hook fastener attachment means, ATM2-SUP on a detachable/re-attachable basis. The body of the strap, AS, functions as the loop fastener attachment means and attaches to the zone of the ATM2-SUP on a detachable/re-attachable basis.

3. A special piece, SP, made from a material such as a layer of latex which is attached to the body of the strap means, AS in order to conform the strap means, AS, to shape it as desired and make it to accept the heel and fit the heel easily. By doing so, it will secure the position of the strap means, AS in the heel and will allow an easy placement of this unit on the heel. So that the strap means, AS can be easily pulled to be attached to the hook fastener attachment means, ATM2-SUP of the support, SUP. Thus by doing so the whole placement of this unit will be easier and the unit will stay on the area more securely, since the shaped, special, piece, SP, will not allow the unit to move to sides while it is being kept in place by the stretchable strap means, AS.

Importantly, this method plays a crucial rule in keeping such units in prominent areas such as heels, knees, shoulder, scalp, elbows, and any similar places. This idea was previously explained to be utilized in other areas such as the knee and can be used in any other site that can be utilized.

Importantly, the shaped piece may be embedded to the body of the strap, or it may be attached to it by various means. It may have a body made from a screen of latex or similar material or it can be a shaped, stretchable layer. Importantly, it may be made in any form, shape or material that will serve this purpose.

Importantly, the specail piece, SP, can be attached to the body of the strap means, AS on a permanent or detachable/re-attachable basis.

Method of use.

1. At the time of use initially the applicant will place the special piece, SP, from this unit on the heel of the person.
2. Then will pull the support, SUP, gently to place on the upper surface of the ankle, foot area. Please note that the support, SUP is attached to the strap means, AS.
3. The applicant will then pull end pieces, ATM2-STR of the strap, AS and attach the body of the strap, AS to the attachment zone ATM-SUP of the support means, SUP on a detachable/re-attachable basis and will continue to pull the rest of the end pieces ATM2-STR to the support in a similar way.
4. Then the applicant will pull the end pieces, ATM2-STR of the strap, AS and attach them to the outer surface of the support means, SUP on a detachable/re-attachable basis and will continue to pull the rest of the end pieces ATM2-STR to the outer surface of the support in a similar fashion.

Figure 14:
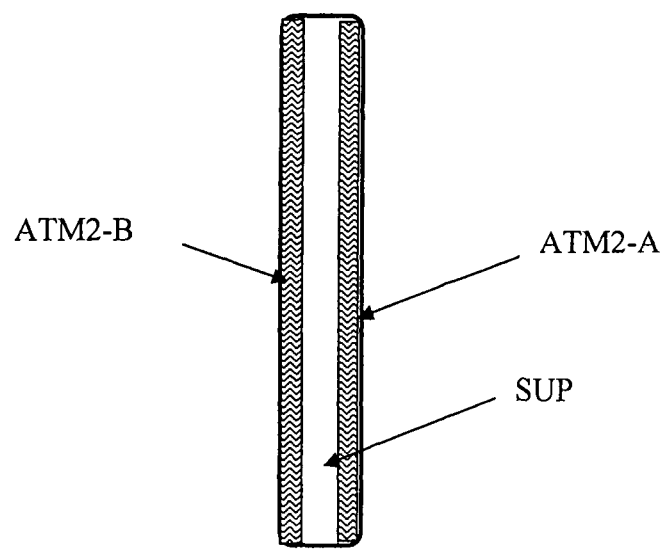
FIG. 14. Show a basic support means for use with straps.

FIG. 14. Shows schematically a non stretchable support means which is long for use in long limbs such as legs, arms and thigh etc. This unit has the same properties mentioned previously for the support means.

In this figure a long non stretchable layer shown at SUP has at least one long zone of attachment means shown at ATM2-A that allows a complimentary piece or a strap means as mentioned in the text to be attached to it on a detachable/re-attachable basis. In this particular unit the support, SUP, has also another of such long zone of attachment means shown at ATM2-B as well.

Very, importantly, please note that the straps means referred in this application are made from a stretchable fabric commonly called "Lycra"™ and is presently available in US market. This stretchable fabric is a woven fabric that has the Lycra in it with other material such as nylon etc. In the course of his research the applicant noted that this material is capable of stretching and detachably/re-attachably, directly attaching to the support through detachable/re-attachable contact of a shiny surface of the Lycra™ fabric with the hook fastener attachment means, Velcro™. Thus he made supports with zones of the Velcro™ attachment means on it's outer surface. Thus the attachment means on the support comprises a suitable hook-type material, such as Velcro. The Lycra™ fabric has a dull (non-shiny) surface opposite the shiny surface. Because of the inventor's discovery of the properties of the Lycra, a strap made from it is both stretchable and directly attachable and detachable to the support so that attachment can be made with different degree of stretching and different distances along the length of the strap, and without any special attachment device attached to the Lycra or the strap. Thus this strap not only is a stretchable fabric but also it functions as a loop fastener attachment means in one of its surface which has a shiny appearance. Therefore, any part of this strap means in the shiny side is capable in attaching directly to a matching hook fastener attachment means, ATM2, on a detachable/re-attachable basis.

This is a very important and useful property and makes this unit unique. It allows making the units explained in this application possible.

This strap has the property of conforming to the shape of the area, that is wrapped such as a limb and joint. It allows the air to go thorough which is important in allowing the sweat to descipate and area to be comfortable. It is a thin, non irritant fabric. Importantly, the applicant has made straps by sewing or attaching this fabric with having the shiny surface to be in the outside so that both surfaces of the newly made strap allows it to be attached to the hook fastener attachment means, ATM2 on a detachable, re-attachable basis. Importantly, in this model the applicant proposes that this fabric may be further modified in order to have zones of loop fastener attachment means, ATM1 on its second/outer surface or the non-shiny surface (the shiny surface that allows the hook fastener attachment means, ATM2 to
attach is mostly reffered as the rear surface). Thus it allows the end of the strap means, which has a zone of hook fastener attachment means, ATM2 to be attached to those zones on a detachable, re-attachable basis. This will be similar to the fabrics that has many patches of raised flowers or special patterns etc. Importantly, such zones of loop fastener attachment means may be woven to this fabric or they may be adhered or attached to the outer surface of the LYCRA™ by various means. Again, the advantage of this modified strap means is that it allows the end piece of the strap, ATM2 to be attached to any part of the outer surface of the strap, STR on a detachable, re-attachable basis.

FIG. 15. Shows schematically a support means for the leg or any long limb that consist of the following:
1. A non stretchable support piece, SUP shown at previous FIG. 14 that allows the straps to be attached to it, on a detachable/re-attachable basis.
2. A trapezoid stretchable strap means shown at, STR1 made from an stretchable fabric that is fixed to the left, long side of the support, SUP, and is designed to wrap around the upper leg and the body of this strap means, STR1 to attach to the ATM2-A of the support means, SUP on a detachable/re-attachable basis. The fixed part of this strap means may be attached to the support, SUP, on a permanent or detachable/re-attachable basis. The free end of this strap means, STR1 may attach to the zone of hook fastener attachment means shown at ATM2-B of the support, SUP, on a detachable/re-attachable basis, per specific design. Importantly, in this model the strap means, STR1, is made from LYCRA,™. Alternatively, it may be made from another type of stretchable fabric with a zone of attachment means, at its end in order to make the attachment to the support means, SUP or the zone ATM2-B possible.

Importantly, the rear/bottom surface of the strap, STR1 may have a zone of loop, fastener attachment means, ATM1 shown in a zone with dotted line around it. This is for use if the strap, STR1 does not have the property to attach to the zone of the hook fastener attachment means shown at ATM2-A and ATM2-B of the support means, SUP, by its own properties such as the Lycra.™ does.
3. A second trapezoid stretchable strap means, shown at STR2 made from a similar stretchable fabric is also fixed to the left, long side/border of the support means, SUP, and is designed to wrap around the lower leg and to attach to the ATM2-A on a detachable/re-attachable basis. Again the fixed part of this strap may be attached to the support means, SUP, on a permanent or detachable/re-attachable basis. The end of this piece may also attach to the zone of hook fastener attachment means shown at ATM2-B of the support, SUP, on a detachable/re-attachable basis, per specific design. Importantly, please note that in this model the strap means, STR2, is made from LYCRA,™. Alternatively, it may be made from another type of stretchable fabric with a zone of loop fastener attachment means, at its make the attachment to the support means, SUP or the zone ATM2-B possible.

Importantly, the rear surface of the strap, STR2 may also have a zone of loop, fastener attachment means, ATM1 in case the strap means does not have the property to attach to the zone of hook fastener attachment means shown at ATM2 of the support, SUP, by its own properties such as the Lycra.™ does. 4. A third trapezoid stretchable strap means, shown at STR3 made from a fabric which is also fixed to the left, long side/border of the support means, SUP, and is designed to wrap around the whole leg over the strap means, STR1 and STR2 and attaches to a zone of hook fastener attachment means, ATM2-C, located on the rear/outer surface of the strap means, STR3 along its base, on a detachable/re-attachable basis. The zone, ATM2-C is a long zone of attachment means that allows the body of the fabric, STR3 or its end piece to be attached to it on a detachable/re-attachable basis. Importantly, in this model the strap means, STR3 is made from LYCRA,™. Alternatively, it may be made from another type of stretchable fabric with a zone of attachment means, at its end. This design is very important, since it makes a stretchable fabric means which will overlap the other strap means STR1 and STR2 and prevent from having a portion of the leg uncovered to bulge. An uncovered area of the leg, thigh or similar place can create a functional problem when one portion of a vessel such as vein is pressed and the portion before that is not covered. This will cause the uncovered vein to engorge, the blood inside it to be stagnant and to have a set of for blood clot formation and phlebitis which is very dangerous.

Importantly, similar units may be also made for the use in the arm, elbow and thigh areas and any other place that can be utilized.

Method of Use.

At the time of use, the support will be located in the shin area of the leg, although, it can be placed in the side of the leg or even in the back particularly, when the unit is designed to be used with use of supports as shown in previous figures. Then one of the smaller trapezoid strap means such as strap, STR1 will be wrapped around the upper leg and will be pulled to be attached to the upper part of the attachment zone, ATM2-A of the support, SUP, on a detachable/re-attachable basis, then it may be pulled more to be also attached to the attachment zone, ATM2-B of the support, SUP, on a detachable/re-attachable basis.

In second step, the second smaller trapezoid strap, STR2 will be also pulled to wrap around the lower leg, and will be pulled to be attached to the lower part of the attachment zone, ATM2-A of the support means, SUP, on a detachable/re-attachable basis.

The end of this strap may be also pulled more to be also attached to the lower part of the attachment zone, ATM2-B of the support, SUP, on a detachable/re-attachable basis. The extra pieces may be trimmed.

At the third move the user will pull the large trapezoid strap, STR3 in the direction opposite to the direction which the first and second straps to wrap over those two straps, STR1 and STR2. Then will pull to attach to the attachment zone, ATM2-C of the unit, on a detachable/re-attachable basis. This strap will mostly cover the end pieces of the previous two straps, STR1 and STR2 and will father cover and support the areas of the leg which the straps means, STR1 and STR2 have not covered. This will leave a smooth finish on the leg.

Importantly, when this unit can be made with use of methods that allows the pressure in the system to be verified, such as straps with pressure sensing capabilities, the balloon system with gage etc. Then it will allow the choice of pressure which these supports can deliver to the limb.

Importantly, the large trapezoid strap, STR3 can be also pulled in the same direction as the first and the second strap means, STR1 and STR2 in order to be attached to the second zone of the attachment means, ATM2-B of the support on a detachable/re-attachable basis. If this is chosen then the end pieces of the straps means, STR1 and STR2 will not be attached to the zone of the attachment means, ATM2-B of the support. Importantly, similar units may be also made for the use in the arm, elbow, thigh, chest, abdomen and any other place that can be utilized.

FIG. 16. Shows schematically the front view of a double sided hook fastener attachment means, ATM2 which has a body made from a relatively rigid layer, Rigid Layer which the body will prevent this unit from significant bending and shrinking. The outer/upper surface of this piece has a zone of hook fastener attachment means, ATM2-A which has a lesser grip/or a lesser aggressiveness and the lower/rear surface has a hook fastener attachment means, ATM2-B shown better in FIG. 16B which is more aggressive and has more grip/and or more surface.

FIG. 16A. Shows schematically the rear view of a double sided hook fastener attachment means, ATM2 which is fully covered with a more aggressive hook fastener attachment means, ATM2-B which will attach to the outer surface of the support.

FIG. 16B. Shows schematically the cross cut view of a double sided hook fastener attachment means, ATM2 with the body of the relatively rigid layer is shown at, Rigid Layer, the outer/upper surface of this piece has a lesser zone of hook fastener attachment means, ATM2-A and the lower/rear surface is covered with a more aggressive hook fastener attachment means, ATM2-B. This method allows this piece to be attached to the outer surface of the support means and also to allow the strap to be attached to the zone ATM2-A from this unit on a detachable basis. however, when the strap is being detached it will not be able to remove this piece from the support since the lower surface of this piece is attached to the support with more aggressiveness and with larger zone of the ATM2 as well.

The use of pad means with these units.

Importantly, pad means may be used with these units in order to allow a particular area of the body or a limb to be compressed more than the surrounding area. In this method a pad means, made from different material may be used to be attached or adhered to the skin and then to have the hose to be worn on top of the pad means and then the strap means to be wrapped around the hose. Importantly, the hose means may have a raised area such as a commonly used ECG pad that initially will be placed on the site of operation and then the hose to be cut to remove the pad, to perform procedure, then to place the pad and wrap the strap means on the pad means.

FIG. 17. Shows some pad means designed for use with these supports for various reasons. The pad means may be made from different materials and means and they also may have different sizes, shapes, thickness and stiffness and other important characteristics. They may be made from inflated or inflatable balloons. They may be made for being attached to the support and the straps in order to be placed under the support and over the wound for various reasons. These pads may be made.

1. A padding with various body, gauze pad, absorbent etc.
2. A balloon with various shapes such as the flat, more round etc.
3. An inflatable balloon that allows the pressure inside the balloon to increase.
4. A shaped balloon, or pad. To apply certain compression in wound.
5. A medicated pad. To deliver medicine to the person.
6. An absorbent pad to allow the drainage of the wound to be absorbed.
7. A sticky pad to adhere to the wound.
8. A pad with nonporous membrane such as vinyl.
9. A pad which has an adhesive tape.
10. Heated pad or cold compresses.

The pad means have a attachment means such as the ATM-X that allows the pad means to be attached to the support or strap means. The attachment means can be of various forms such as; adhesive, snaps, fastener means, bands etc. So that it can allow the pad means to be re-positioned or exchanged. Also importantly, the pads may be attached to the wound area by adhesives or bands so that then the support can be placed on them and compressed.

The model in the right side of the figure shows a pad, Pad with adhesive tape, Adhesive Tape attached to it. This model allows the cover of adhesive to be removed along the dotted line so that the pad can be adhered to the skin by use of the adhesive tape. This allows the pad to stay on the wound so that the support can be placed on top of the pad and the straps to be wrapped on the site. This can be useful in cases such as the injection for the superficial veins in order to provide compression on the vein site.

Importantly, the pad may have different thickness or consistency for applying different level of pressure to the wound. Example of this is shown in right side, this unit has a smaller, thicker central piece shown with a dotted circle and a thinner, or softer larger piece shown in large circle. Such a unit allows the center of the wound to be compressed more. Different sized or shaped units may be made for other uses. The characteristics of these pad may vary in many ways to satisfy different needs.

Also Importantly, the pads may be made to be medicated pads, in order to deliver medication to the wound. Also they may provide heat or cold to the wound by use of heated pads, heated units or cold compresses.

FIGS. 18-19 shows the use of hand held applicators with the long strap means for an easy delivery. The use of these units allow the strap to be applied to the limb and also removed from the limb with ease. Two models of these units are shown in this application.

The unit shown in FIGS. 18 and 18A consist of a rectangular shaped, more rigid layer, Rigid Layer which has pads, Pad placed in the sides of this unit to provide more body and grip to this unit. A zone of loop fastener attachment means, ATM1 is on the surface of one or more of these pads or alternatively the body of pad may be made with an outer surface made of loop fastener attachment means, ATM1.

This zone allows the end of the strap means STR-F from FIG. 8 which has a zone of ATM2 to be attached to it on detachable, re-attachable attachment basis, and to be wrapped around it. At the time of storage the first free end of the strap, STR-F which has a zone of ATM2 will be attached to the body of this unit and the strap will be wrapped around the adaptor and will be hold in a compact secure condition. At the time of delivery the second or the free end of strap will be attached to the body of the support, SUP and the strap will be unwraped from this unit and wrapped around the limb till finally its end piece will be attached to the outer surface of the strap means. The cross cut view of this model is shown at FIG. 18A. A handle may fit the middle zone of this unit between the pad means in order to allow the applicator to be used easily.

FIG. 19 shows the second model which has a cylindrical body, shown at Outer Cylinder which has a central opening that allows a handle, Sliding Handle to move and be fixed in either side to function as a handle. The outer surface of the outer cylinder has a zone of loop fastener attachment means, ATM1 on it, which allows the end of the strap means STR-F which has a zone of ATM2 be attached to it on detachable, re-attachable attachment means. At the time of storage the first free end of the strap, STR-F which has ATM2 will be attached to the body of the adaptor and the strap will be wrapped around the adaptor and will be hold in a compact, controlled pattern. At the time of delivery the second or the free end of strap will be attached to the body of the support, SUP and the strap will be unwraped from the adaptor and wrapped around the limb, till finally its end piece will be attached to the outer surface of the strap means. The handle may be made to move and hide inside the body of this unit.

DETAILED EXPLANATION OF THIS INVENTION

This invention is related to an improved version of the wound wrapping and support means for use in a living body. Wrapping a limb and applying compression to the limb is important in conditions such as control of varicose veins, limb swelling and post surgical status for the vessels or cosmetic surgery and similar. This applicant has introduced different models to the USPTO that are designed for solving such problems. In this application he introduces another version of these units which are better for use in certain conditions such as post OP cases for the limbs. In this model the units continue to utilizes special stretchable fabric such as the Lycra™ which functions as a loop fastener attachment means, thus it is capable of attaching directly and in any part of it to the hook fastener attachment means, such as Velcro™ hook on a detachable, re-attachable basis. Very, importantly, please note that the straps means referred in this application are made from a stretchable fabric which is a woven fabric that has the Lycra™ in it with other material such as nylon etc. In the course of his research the applicant noted that this material is capable of stretching and detachably/re-attachably, directly attaching to the support through detachable/re-attachable contact of a shiny surface of the Lycra™ fabric with the hook fastener attachment means, Velcro™. Thus he made supports with zones of the Velcro™ attachment means on it's outer surface. Thus the attachment means on the support comprises a suitable hook-type material, such as Velcro™ The Lycra™ fabric has a dull (non-shiny) surface opposite the shiny surface. Because of the inventor's discovery of the properties of the Lycra, a strap made from it is both stretchable and directly attachable and detachable to the support so that attachment can be made with different degree of stretching and different distances along the length of the strap, and without any special attachment device attached to the Lycra or the strap. Thus this strap not only is a stretchable fabric but also it functions as a loop fastener attachment means in one of its surface which has a shiny appearance. Therefore, any part of this strap means in the shiny side is capable in attaching directly, to a matching hook fastener attachment means, ATM2, on a detachable/re-attachable basis.

This is a very important and useful property and makes this unit unique. It allows making the units explained in this application possible.

This strap has the property of conforming to the shape of the area, that is wrapped such as a limb and joint. It allows the air to go thorough which is important in allowing the sweat to desciapte and area to be comfortable. It is a thin, non irritant fabric. Importantly, the applicant has made straps by sewing or attaching this fabric with having the shiny surface to be in the outside so that both surfaces of the newly made strap allows it to be attached to the hook fastener attachment means, ATM2 on a detachable, re-attachable basis. Importantly, this applicant also has proposed that this fabric may be further modified in order to have zones of loop fastener attachment means, ATM1 on its second/outer surface or the non-shiny surface (the shiny surface that allows the hook fastener attachment means, ATM2 to attach is mostly reffered as the rear surface). Thus it allows the end of the strap means, STR-S which has a zone of hook fastener attachment means, ATM2-B shown in FIG. 1A to be attached to those zones on a detachable, re-attachable basis. This will be similar to the fabrics that has many patches of raised flowers or special patterns etc. Importantly, such zones of loop fastener attachment means may be woven to this fabric or they may be adhered or attached to the outer surface of the LYCRA™ by various means. Again, the advantage of this modified strap means is that it allows the end piece of the strap, ATM2-B shown in FIG. 1A to be attached to any part of the outer surface of the strap, STR-S on a detachable, re-attachable basis. Thus it prevents the end of the strap means shown in the left side of the FIGS. 1 and 1A to be loose. This provides a grate advantage in handling the unit made from this strap for the purpose intended in this application. The advantage is that the very end of the strap after wrapping a limb will attach to the outer surface of its own and will be stable and fixed. Also in some other models it allows wrapping of the strap over itself multiple times without allowing it to slip. The support will hold the strap in position securely and prevent it from moving.

This strap means will be attached to a support means of various forms such as a zone of hook means, hose means, or a panty hose that has zones of hook fastener attachment means on it or between these two units so that the strap means will wrap around the limb in oblique fashion while being pulled while it is being wrapped upward in an oblique fashion. So that finally the limb will be covered by the stretchable strap which it is in pulled condition. This will provide tension in the strap, compression on the limb and will protect the underlying vessels and the tissue properly. Different straps or multiple straps may be used with this unit. Pad means may be also used with these units.

The special strap means generically referred as, STR is made from a stretchable fabric that functions as a stretchable, loop fastener attachment means as well. Thus not only it is a stretchable fabric and allows it to be wrapped for constriction of the limbs and body but also it functions as a loop fastener attachment means in at least one of its sides which is shiny and any part of this strap means in the shiny side attaches to a matching hook fastener attachment means, generically referred as, ATM2, on a detachable/re-attachable basis. This is a very important and special property and makes this unit unique and allows making the such units possible. The dull side, in the other hand attaches to a hook fastener attachment means, ATM2, on a detachable/re-attachable basis with a far less grip, there is possibility that this property or the hook fastener attachment means, ATM2 to be modified to make such engagement more aggressive.

This strap means is a thin fabric and is capable of conforming to the shape of the area, it allows the air to go thorough, is thin, non irritant fabric. Also the stretchability of this unit allows the strap means to be pulled and wrapped to a limb for creation of tension and compression in the limb for positive effect in conditions such as control of pressure in the limb.

An example of this fabric as the applicant has found is LYCRA,™ or similar. The applicant believes it is easy for the experts in the field to modify the available knowledge of manufacturing the hook fastener attachment means, for making a special hook fastener attachment means to attach to this unit more aggressively.

In the available material to the applicant commonly, only the shiny face of this fabric is able to function as loop fastener attachment means, but Importantly, this can be altered to make both sides to attach to the hook fastener attachment means, ATM2. For example I. This fabric may be sewed to be double sided, for attaching to the hook fastener attachment means, ATM2 in its both sides.

II. To be modified in order to allow the hook fastener attachment means to be attached to this strap on both of its surfaces on a detachable, re-attachable attachment means.

III. The fabric may be changed to have zones of loop fastener attachment means, ATM1 on its dull surface and modify it so that it will allow the hook fastener attachment means, ATM2 to attach to it on a detachable, re-attachable basis. This will be similar to the fabrics that has many patches of raised flowers or special patterns etc. Importantly, these zones may be woven to the fabric or they may be adhered or attached to the outer surface of the LYCRA™ by various means. The advantage of this modified strap means is that it allows the end piece of the strap, ATM2-S to be attached to any part of the outer surface of the strap, STR-S on a detachable, re-attachable attachment means, and this prevents the end of the strap means to be loose. This provides a grate advantage in handling the unit made from this strap for the purpose intended in this application and similar units. The advantage is that the coming strap after wrapping a limb will attach to the outer surface of its own and will be more stable and will not slip. Also it allows wrapping of the strap over itself multiple times without allowing it to slip. The support will hold the strap in position securely and prevent it from moving.

FIG. 1X. Shows an elastic strap means which consists of two segments, STR-A and STR-B attached to each other, permanently or removably. The body of this strap means is made from a special fabric which the applicant found for use in this sort of strap means and has introduced it to the USPTO in his previous applications. This fabric is a stretchable, woven fabric made from Lycra™ with other materials such as Nylon or similar. The available Lycra™ fabric has a dull (non-shiny) surface opposite the shiny surface. In the course of his research the applicant noted that the shiny side of this material is capable of detachably/re-attachably, directly attaching to the support through detachable/re-attachable with the hook fastener attachment means, Velcro™, while being stretched. Thus he made supports with zones of the Velcro™ attachment means on the outer surface of the supports. Thus the attachment means on the support comprises a suitable hook-type material, such as Velcro™. Thus the straps made from this material is both stretchable and directly attachable and detachable to the hook, fastener zones of the support so that attachment can be made with different degree of stretching and different distances along the length of the strap, and without any special attachment device attached to the Lycra or the strap. Thus this strap not only is a stretchable fabric but also it functions as a loop fastener attachment means in one of its surface which has a shiny appearance. Therefore, any part of this strap means in the shiny side is capable in attaching directly to a matching hook fastener attachment means, ATM2, on a detachable/re-attachable basis.

This is a very important and useful property and makes this unit unique. It allows making the units explained in this application possible.

This strap has the property of conforming to the shape of the area, that is wrapped such as a limb and joint. It allows the air to go thorough which is important in allowing the sweat to descipate and area to be comfortable. It is a thin, non irritant fabric. Importantly, the applicant has made straps by sewing or attaching this fabric with having the shiny surface on both surfaces of the straps, shown at FIGS. 1Y and 1Y-A thus the newly made straps allow it to be attached to the hook fastener attachment means, ATM2 on a detachable, re-attachable basis, in both sides.

In the model shown in this figure the initial segment of the strap means, STR-A is chosen so that its outer surface has the dull face, Dull Face and its inner=rear surface has the shiny face. In contrast the second segment, STR-B has an outer surface which has a shiny surface, Shiny Face, thus its inner=rear surface will be dull. The outer surface of the initial end of the strap A, STR-A has a zone of hook fastener attachment means, ATM2 that allows the inner surface of the body of this segment, STR-A of this strap means to be attached to it after wrapping around the limb. The end of the strap A also has ATM2 in its lower=rear surface of the end as well which allows this unit to be attached to a support means as shown at FIGS. 4, 5 and similar.

The other end of this strap means at the end of the STR-B has a zone of hook fastener attachment means, ATM2-R on its rear surface. Thus it allows this end to attach to the outer surface of the second segment of this strap means, STR-B which has a shiny surface, on a detachable, re-attachable basis, after being wrapped on the limb. So that the end piece of this unit will be attached and on control. Importantly, a strap means may be made by attaching different segments to each other by use of the attachment means at the ends so that the final piece will have the desired length and properties.

FIG. 1X-A. Shows schematically the cross cut, side view of the strap means, shown in FIG. 1X. In this figure the shiny face, Shiny Face of the strap A, STR-A is in the lower side and the dull face, Dull Face, on its upper surface. In contrast the second segment, STR-B has an upper surface which has a shiny surface, Shiny Face, and its lower face has the dull face, Dull Face. The zones of the hook fastener attachment means, ATM2, in the upper and lower as well as the zone of ATM2-R, in the lower are shown.

FIGS. 1Y and 1Y-A. Shows the front and the cross cut view of a strap means, STR-C which is a modified model with a shiny surface on its both front and rear surfaces. Thus it allows the attachment of a zone of hook fastener attachment means, ATM2 to its front and rear surfaces and on a detachable, re-attachable basis. Thus the end, ATM2-R of the strap means, STR-C will be capable to be attached to the outer surface of this strap in any area and on a detachable, re-attachable basis. The initial end of this strap means has a zone of hook fastener attachment means, ATM2 that allows the body of the initial segment of this strap means to be attached to it after wrapping around the limb. The inner or the lower surface of this strap has the zone of hook fastener attachment means in its rear surface shown at ATM2-R. Which allows the control of the end of this strap after being wrapped on the limb. So that the end piece of this unit will be attached and on control.

FIG. 1Y-A. Shows schematically the cross cut, side view of the strap means, STR-C, shown in FIG. 1Y. In this figure the body of the strap means has the shiny face, Shiny Face on both side, in the upper and lower sides. The zones of hook fastener attachment means, ATM2 and ATM2-R are shown with their locations.

Importantly, note that the strap means, can be used on a limb alone. While the unit can be utilized with more ease and functionality when it is used with a support means shown in the text.

The strap means may have various means on/in its body in order to allow the strap means to attach to itself while wrapping so that the strap means will not slip. Some of these methods are shown at FIGS. 1-1A FIG. 1. Shows a strap means similar to the model explained in text and exampled as Lycra™, except in this model the strap means, STR-S, has zones of hook and loop fastener attachment means, ATM2 and ATM1 on it's outer surface, dull surface shown at Dull Face. So that this modification allows the following.

IA. The outer/rear surface shown at FIG. 1A of the body of the strap, STR-S which is made from a stretchable, loop fastener attachment means such as LYCRA,™ or similar, to be attached to the zones of ATM2 on a detachable, re-attachable attachment basis. This provides significant advantage which is more stability of the strap that prevents the outer strap to slide from the inner strap when the strap is wrapped on a patient's limb. This prevents the strap from displacement and falling.

IB. Also outer/rear surface of this strap means, which is the dull face, Dull Face has zones of the loop fastener, attachment means, ATM1 on it so that allows the end of the strap means itself or the beginning of another similar strap which has zones of hook fastener attachment means, ATM2 to be attached to these zones on a detachable, re-attachable attachment basis, in order to control the end of the strap.

Also both ends of this strap means may have a zone of loop fastener, attachment means, ATM1-A and ATM1-B on its upper/outer surfaces respectively and a zone of the hook fastener attachment means, ATM2-A and ATM2-B in its lower surface respectively. These zones allows the end of one strap to attach to these on a detachable, re-attachable basis Importantly, the strap may also have zones of adhesive means, ADH, shown at FIG. 1A, that allows the strap to be adhered to the skin or to the underlying strap or other objects in order to add more stability and security.

FIG. 1A. Shows schematically the cross cut side view of the strap means, STR-S shown in previous FIG. 1. In this figure the body of the strap means is shown at STR-S, the shiny face, Shiny Face of this strap means is in the lower/rear side and the dull face, Dull Face, the upper surface of this strap means has zones of both the loop fastener, attachment means, ATM1 and also hook fastener attachment means, ATM2 on it only few are marked. Importantly, this allows the end of the strap means, STR-S to attach to the loop fastener attachment means, ATM1 of the outer, surface of this strap when is wrapped on a living body, also the inner/shiny surface of the strap means, STR-S to attach to the zones of the hook fastener attachment means, ATM2 of this strap on a detachable, re-attachable attachment basis, for making a very sturdy, stable attachment.

Both ends of this strap means have a zone of loop fastener, attachment means, ATM1-A and ATM1-B on its upper/outer surfaces respectively and a zone of the hook fastener attachment means, ATM2-A and ATM2-B respectively.

FIGS. 2 and 2A. Show the use of these strap-support means in some other conditions. FIG. 2. Shows a strap means made from Lycra™, STR-BR that has a support, SUP made from a laminate as explained in the text with zones of double side hook fastener attachment means, ATM2-DS on it. The end of this strap means, STR-BR, has the following.

1. It has a zone of loop fastener attachment means, ATM1 at its outer surface that allows the ends of this pieces to attach to them if needed.

2. The end of this strap means has a cut that allows the two ends so that one of them can be attached to the support when needed.

3. The ends has pieces of double side hook fastener attachment means, ATM2-DS on them that allows them to be attached to the outer surface of the support when needed. This unit will be wide to be used in certain areas such as the females or males with large breasts that would stand on the way of procedures such as the isotope scanning of the heart and cause breast attenuation.

FIG. 2A. Shows a strap similar to the straps means for holding certain patients in procedures such as taking X-Rays or similar which the body of the patient needs to stay in certain position for some time. In this model the strap means, STR-A and STR-B are made from two pieces of Lycra™, that has a means of attachment, ATM2-W which are designed to attach to the walls or X-Ray table or similar on a detachable, re-attachable basis. The body of the strap, STR-B has shiny face, Shiny Face outside and also has a support means, SUP made from a laminate as explained in the text with zones of hook fastener attachment means, ATM2 on it. The strap means, STR-A has a dull face out, Dull Face with a zone of hook fastener attachment means, ATM2 at the end of this strap means. This design allows the straps to be attached to the sides of the wall or the X-Ray table or the site which the X-Ray will be taken and to hold the patient as follows.

FIGS. 2B and 2C. Shows method of using a strap means, metal plate and foam for keeping patient in position. In this figure the place for taking X-Ray is shown at X-Ray Stand and a metal plate, Metal Plate is fixed to proximity of this place either on its own border or on the wall by a fixed or detachable, re-attachable basis. So that the plate will function as a wall and prevent patient from moving further. A strap means, STR-A such as one shown in previous FIG. 2A is attached to the wall or the side of the X-Ray Stand, by a fixed or detachable re-attachable means, shown at Attachment Means. This method allows the strap to be pulled over the body of the patient in order to attach to the Metal Plate or its vicinity on a detachable, re-attachable basis. A foam means, Foam or two will be used to keep patient further in position. This method allows the patient to be placed in the selected position and will prevent from moving and falling. FIG. 3. Shows a strap means made from Lycra™ except the body of this strap means, STR-T, has dots or zones, Latex dots of materials such as latex or rubbery, or other synthetic material that are raised or have raised parts that will function for preventing the overlaping strap to skid. These raised zones can be located on the one surface of strap and it will provide a sort of grip on the in-coming surface of the strap or fabric so that the combination will prevent them from sliding, or displacing easily. Importantly, these dots or zones can be only in one side or in both sides of this fabric.

This method is designed to provide the following advantages.
1. More stability to these units. So that one unit would not slide or skid over the other and will keep its position as it was placed initially.
2. It will not stick these straps to each other.
3. It may promote the attachment of these two straps.

In this figure this material is shown in the form of dots, Latex dots which is scattered all over, although they may be made in the form of lines of different shapes or patches. The thickness and the shape of these spots or means may wary and they may have a shape that will engage with each other when are in approximation or the contact of each other.

Importantly, instead of the latex dots the unit may have any other kind of means or materials that allows these two straps to be attached or adhered to each other on a detachable basis. These materials can be
1. A sticky material, such as gel, gluey material or any other synthetic material which will provide a gluey function without being adhesive and loosing its function in a long run or after being washed.
2. A series of microscopic pins that designed to engage with the body of the fabric but flat enough to avoid hurting the skin.
3. Adhesive materials of various forms that will fit this use, either available ones or means that can be made for such use in future.
4. Any other materials that can be made for use in these units for these purposes.

This figure also shows that the strap has a series of openings, Open, that allow the air to go thorough for various reasons, ventilation, heat control etc.

The end of the strap also has an end piece that allows it to engage with the strap and keep the end stable.

The end of the strap after being wrapped to the limb will engage the means that falls under the support group which is stable of its own and does not move down and thus when the strap is attached to support it will prevent the strap from falling. Thus the strap means uses various methods that are designed in order to allow the strap means to be held wrapped around the limb and to prevent it from sliding, displacement or falling. These methods can be of the following.
A. A support means which has a rather rigid body or other rigid materials attached to it so that it the relatively rigid material will prevent the support from shrinking, thus it would not allow the strap means to move down in conditions that it would such as in the arms, legs or thighs. The support means has zone/s of attachment means, ATM2 so that the strap means will be attached to the support by any method so that the body of support will prevent the strap from moving.
B. The support means can be in the form of a netting or similar with having a series of attachment means, ATM2 so that the strap means will be attached to the attachment means, ATM2 and thus the combination prevent the strap means from moving and falling. The netting will have a relatively rigid pieces which will hold the netting stable and prevent it from shrinking along a line, such as vertical lines/horizontal in sitting position or lying down.
C. The attachment means, ATM2 may be hold in place by way of bands, non shrinking body or any other means that can keep these stable so that the strap means may be wrapped and kept in place by use of the attachment means.
D. In other method an stretchable hose means are utilized so that the strap means will be combined with the hose means in order to prevent the strap means from dislocation and falling. The stretchable hose will be further intensified by use of a relatively rigid pieces as explained in the text which will hold the stretchable hose in stable position in the direction which is desired and prevent it from shrinking along a line, such as vertical lines/horizontal in sitting position or lying down.
E. In a model a stretchable panty hose is utilized which has means of attachment in its surface or body so that it allows the stretchable strap means to be wrapped around the limb and be hold by the panty hose in place in order to prevent the strap means from dislocation and falling. The panty hose has strings, bands or straps of no-stretchable material that will be embedded to be part of its body to prevent it from shrinking along the vertical line in standing thus it will prevent the strap means from moving down toward the feet. The strap means then will apply most of the compression to the limb. In this method one end of the panty hose is fixed on the foot and the other end in the belt area so that its length can not shorten.
F. In a model a stretchable panty hose is unutilized which functions as a loop fastener attachment means, ATM1 so that a relatively rigid strap of ¾×10 inches with an inner surface that has hook fastener attachment means, ATM2 such as one shown at FIG. 6 can be attached to it on a detachable, re-attachable basis. This panty hose will stay on body and the belt will not allow it to fall when standing. The rigid strap will prevent it from shrinking lengthwise. The rigid strap has hook fastener attachment means on its outer surface that allows the stretchable strap means to be wrapped around the limb, to attach to its outer surface each time that comes in contact with it so that the combination of the panty hose and rigid strap means will prevent the strap means from displacement and falling. The strap means will be the unit that will apply most of the compression.

Alternatively, the stretchable hose means is made from Lycra™, the same material as the strap, or similar. This fabric is sewn so that it will fit parts of the body which is to be wrapped for example, the feet, ankle, leg, knee, thigh, lower abdomen etc. Importantly, the shiny side will be out so that the hook fastener attachment means, attachment means, ATM2 can be attached to it on detachable, re-attachable basis. In general the hook fastener attachment means, ATM2, may be attached to the outer surface of the hose means by. 1. Being sewed. 2. Being adhered. 3. Being manufactured to be part of the structure of the fabric. 4. By welding to fabric by laser, ultrasonic means or any other means. 5. By attaching to the surface of the hose by attachment means of various kinds such as hook and loop fastener attachment means.

Importantly, in either case the hose or panty hose may have strings, bands or straps of non-stretchable material as shown at Non-Stretch-Line at FIG. 6, that will be embedded to be part of its body to prevent it from shrinking along the vertical line in standing thus it will prevent the strap means from moving down toward the feet. The strap means then will apply most of the compression to the limb. Thus using this method one end of the panty hose is fixed on the foot and the other end in the belt area so that its length can not shorten. Importantly, since the hose material is stretchable, thus a few sizes of this unit will be able to fit the user and be useful to a large group of people. The no-stretchable parts will be adjusted to allow their length to match the size of the person. FIGS. 3A and 3B shows few models of end pieces means that allow the end of the strap to be attached to the body of the strap means which is on the limb already. FIG. 4. This figure shows a very distinct wrapping system of a limb and a method of doing it which consist of a support, strap means similar to the main models discussed in the text. Except in this model the unit has.

1. A support means, SUP which is made from a long layer of either laminate or similar unit which has an outer cover made from loop fastener attachment means, ATM1 which also has zones of hook fastener attachment means, ATM2 on it that allows the strap means, STR made from a material such as lycra to be attached to it on a detachable, re-attachable attachment means. Also the end of the strap means, with ATM2 to be attached to it on detachable, re-attachable attachment means. These hook fastener attachment means can be 1. From soft flexible material.
2. From a rather rigid material in order to prevent the support from shrinking and bending.
3. From combinations of multiple small pieces that can be removed and attached.
4. Can be double sided hook fastener attachment means.

Importantly, the body of the strap means, STR consist of two segments.

a. The initial first segment of the strap means, STR-E which is attached to the support, SUP, is a long elastic strap means, STR-E which the shiny surface of the strap is in the rear/lower side of it. So that this part will wrap around the limb and attach to the ATM2 of the support, SUP on a detachable, re-attachable attachment means. Importantly, the STR-E may have zones of hook fastener attachment means, in its front surface, ATM2-IF which allow the shiny surface of the strap to attach to these zone after the first wrap around the limb. Importantly, this figure such zones may be located only in the upper border of the strap, STR-E in order to prevent them from being uncovered and to attach to the dress of the users. Since the strap will be moving up from the ankle toward the knee.

b. The segment STR-F is also made from a material such as lycra but its shiny surface is outside/in front so that the incoming end piece with ATM2, will attach to it on a detachable, re-attachable attachment means. Importantly, the rear surface, dull surface of the segment STR-F may have zones of hook fastener attachment means, ATM2-IR in order to allow the upcoming part of this strap to be attached to these on a detachable, re-attachable attachment means. Importantly, this figure such zones may be located only in the lower border of the strap, STR-E in order to prevent them from being uncovered and to attach to the dress of the users. Since the strap will be moving horizontally or somewhat down from the knee toward the knee.

Importantly, this strap means is long for being long enough to be wrapped around the leg, arm or another part of the body and to have its end piece to be attached to it by attachment means, ATM2 or any other means on a detachable, re-attachable attachment means, by one of following means.

1. Having the zones of attachment means such as loop fastener attachment means, ATM1 on the outer surface of the strap means so that the end piece of the strap which has attachment means to be attached to it on a detachable, re-attachable attachment means. An example of this is shown at zones of ATM1 at the outer surface of the end of the STR-E and also at the outer surface of the strap, STR-F. These zones allows the hook fastener attachment means, ATM2-F from the end of the strap STR-F to attach to one of these, which ever that matches its position on a detachable, re-attachable attachment means, and in a more durable basis.
2. Having a strap means made from double sided lycra, so that the hook attachment means at the end piece of the strap, ATM2 to be attached to it on a detachable, re-attachable attachment means.
3. Having one segment of the strap, STR-E such as the initial part of the strap to have an outer surface of the lycra that has a shiny surface and allows the end piece of the strap, ATM2 to be attached to it on a detachable, re-attachable attachment means.
4. The rest of the strap may have a segment such as STR-F which has an outer surface made from shinny surface of lycra or double sided lycra that allows the ATM2 to attach to it on a detachable, re-attachable attachment means.
5. Use of a complementary piece such as one shown at FIG. 4A.
6. Use of various snaps or end pieces, some shown at this application at FIGS. 3, 3A and 3B.

The optional segment of loop fastener attachment means, ATM1 can play a very crucial role in allowing the end, ATM2-F of the strap means, STR-F to be attached to it on a detachable, re-attachable attachment means. Since the straps can be attached to different spots of this piece thus this allows the functional length of this segment to be decided so that the end ATM2-F will fit and attach to this segment and allow multiple detachment and re-attachment. Also it allows custom made units to be made for this purpose so that the end of the strap, ATM2-F will end to attach to this segment.

Also the zone of hook fastener attachment means, ATM2 on the ATM1 allows the body of the STR-F to be partially attached to it for some stability. The method of use.

In this method the user places the support means, SUP on the leg or arm in a suitable place and the strap can be in one end of the SUP or the other end. For example the support-strap means, will be placed in lower leg close to the ankle and the user will wrap the strap around the leg obliquely to move up close to knee while pulling. In each wrap the inner surface of the strap will attach to the ATM2 of the SUP till the STR-F comes and the end of this segment will attach to it on a detachable, re-attachable attachment means.

The end of the strap shown at ATM2 made of hook fastener attachment means or similar unit has capability to attach to the outer surface of the strap on detachable, re-attachable attachment means.

The end piece of the strap, STR-F has an attachment means, ATM2 which can be also as follows.

1. The rear surface of this attachment means to be, hook fastener attachment means, ATM2. And the front also to have a the same.
2. The rear surface of this attachment means to be the hook fastener attachment means, ATM2. And the front also to have a loop fastener attachment means, ATM1.
3. If the need comes the end of the complimentary piece, SUP-B will be attached to the end of the ATM2-F and its strap, STR-G will be wrapped to allow its end piece, ATM2-G to attach to the SUP-B. The D-ring will allow the length of the STR-G to be adjusted.

Importantly, the strap may use an adaptor that allows the strap to be delivered easily and also to be removed and re-applied easily.

Importantly, the zones of hook fastener attachment means, ATM2 located on the support, SUP may be made by following the following methods.
1. A rather rigid layer which has an outer layer with
   A. a zone of hook fastener attachment means, ATM2-Y in its rear/lower so that it can be attached to the outer surface of the support with loop fastener attachment means on its surface. B. a zone of hook fastener attachment means, ATM2-Z on its front/outer surface so that the incoming strap means, STR can be attached to it on a detachable, re-attachable attachment means.

Importantly, the grip of these two hook fastener attachment means may vary to allow more grip for attaching to the support, SUP so that when the strap, STR is being pulled away this piece would not be dislodged.

Importantly, the body of the rigid layer will prevent the support from shrinking.

FIG. 4AB. Shows schematically, a strap means similar to the STR-F which has a stretchable body made from Lycra™ that has two ends with zones of hook fastener attachment means, ATM2-IR at each side, only the location of one of them is shown in the left site at, ATM2-IR that allows these ends to attach to the outer surface of a long zone of loop fastener attachment means, ATM1L of another unit on a detachable re-attachable basis. This allows the point of attachment of this strap to these zone to be decided in order to change the effective length of the ultimate piece. Thus by this method the final end of the strap means at the left side of the figure will be able to wrap around the limb and to come back and attache to the zone of ATM1 on a detachable, re-attachable basis. This strap also has multiple zones of loop fastener attachment means, ATM1 on its outer surface so that the end piece of the strap, which has a zone of hook fastener attachment means, ATM2-IR in its rear surface to be able to attache to it on a detachable, re-attachable attachment means. Also of interest is the presence of hook fastener attachment means, ATM2-R in the rear surface of this strap, that allows these zone to attach to the outer surface of the underlying surface of this strap on a detachable, re-attachable attachment means.

FIG. 4B, shows a piece of support means, SUP which has an outer layer covered from loop fastener attachment means, ATM1 has a body to function as a zone of attachment means that allows the following.
1. One strap, STR-E to be attached to the other on a detachable, re-attachable attachment basis.
2. The support, SUP to allow the strap to attach to its attachment means, ATM2 after being wrapped on the limb.
3. To allow the length of the straps to be modified.
4. To allows the functional property of the outer sides of the strap means to be changed. Dull face in front on one and shiny face in front of the other one.

In this view the support, SUP is attached to the strap, STR1 that the front face of the lycra, Dull Face on a detachable, re-attachable attachment basis, in zone 1. In the left side it is attached to the second strap, STR2 made from Lycra shiny face in front, Shiny Face at zone 2, Zone 2 on detachable, re-attachable attachment means. The strap means have hook fastener attachment means, ATM2-KR and ATM2-LR on their rear ends respectively. Importantly, the front end of these strap means may also have loop fastener attachment means, ATM1 on their outer/front surface to allow one end of another strap to be attached to it. Importantly, the size, shape and nature of the second strap m FIG. 4C. Shows symbolically a method of combining the strap-support means shown in FIG. 4 with other units for the purpose of making a complete system to cover from the foot to the thigh area. In this method the user can have an stretchable hose system shown in this figure which is designed to have the capacity of compression of the thigh area, it can also extend to go over the knee area and to have the coverage of the knee as well. This system has attachment means, ATM designed to accept the support of the unit shown at FIG. 4. So that the combination will have the more adjustable compression of the legs which are more important due to the severity of the vascular problems and the higher hydrostatic pressure in the area. AS well as the compression of the thigh and knee area. In this figure the trunk piece, Trunk piece is shown as well as the pieces for the thigh, Thigh piece with the attachment means, ATM shown.

Importantly, the unit may consist only from the leg support and the knee hose.

FIGS. 5, 5A and 5B. Shows a support-strap-pad means similar to the model shown at FIG. 4 except this unit has a ring means, A-Ring that allows it to be placed in a finger so that the body of a support means, hear shown at PAD1, can stand on the hand-wrist area easily. This unit also has a supplementary pad means, PAD2 shown at FIGS. 5A and 5B, for use with this unit. These pad means allow the thickness of the pad means to be modified, by having another pad means attached to it on a detachable basis. The body of this support will stand on the lower part of the forearm and wrist while exposed to a pressure when being placed on a desk or similar, during typing, being sited on the handle of the arm chairs or any condition that expose this area to pressure. This support has a longitudinal body that functions as a padding means for preventing from the sensitive parts of the wrist from touching the adjacent objects. The outer surface of the support or pad means, PDA1, has a surface covered with loop fastener attachment means, ATM1 which allows the hook fastener attachment means, to be attached to it on a detachable, re-attachable basis. Also the support may have one or more zones of hook-fastener attachment means, ATM2, on it that allows the strap means, STR, to be attached to these zones after being wrapped around the wrist. In prototype model the body of the support, SUP is made from the laminate that was mentioned in the text with an outer layer from loop fastener attachment means, inner lining and a foam means sandwiched in between. Thus the surface of the pad, PAD1 is a layer of loop fastener attachment means. Importantly, in practical term the support, SUP and the pad means, PAD1 are the same in this prototype model and the support, SUP functions a pad means, PAD1. One end of the strap, STR in this particular model also has a zone of double sided hook-fastener attachment means, ATM2, which allows
1. The strap, STR to be attached to the surface of the support, SUP or the pad means, PAD1 on a detachable/re-attachable basis.

2. The strap to wrap around the wrist and have the end of the strap, STR, to be attached to the outer zone of the strap on a detachable re-attachable basis. When the body of the strap means provides such chance.

The support, SUP or the pad means, PAD1 has an adjustable ring, A-Ring that is designed to be placed around a finger such as the middle finger in order to keep the support, SUP or the pad, PAD1 in a stable position without allowing it to move. This ring, A-Ring may have an adjustable means to allow its length to be adjusted; such as one end being fixed and the other end being attached to the body of the support, SUP or the pad means, PAD1 on an adjustable basis. In this model a zone of double sided attachment means shown schematically at ATM2, allows such an attachment when the body of this ring is made from Lycra,™.

The body of this ring may be made from a stretchable material in this case a different attachment means will be used to allow the attachment to occur. Various ways may be used to make the length of this ring adjustable, such as.

a. The ring to be made from an elastic or stretchable material to allow its length to adjust during function. b. A non-elastic material that goes around a finger but its length does not change.

c. In both cases the length of the ring, A-Ring may be adjustable.

The body of the pad, PAD1 has an attachment means such as a strap, STR that is made from an stretchable material "Lycra.™". which functions as the loop-fastener attachment means, ATM1. The end of this piece has a zone of double sided hook-fastener attachment means, ATM2 as shown.

The protective pad means, PAD1 may be made to have an adjustable body by. 1. Making it from an inflatable balloon so that the degree of inflation to allow its thickness to be modified. 2. By making it from combinations of pads, having one pad such as PAD1 and having a second pad such as pad means, PAD2 to be attached it on a detachable/re-attachable basis. So that by attaching the extra pad means the thickness and the shape of the pad can be modified. The attachment of these two pads to each outer may be achieved by use of hook and loop fastener attachment means, bands or any other kinds of attachment means that can be used. In this model the pad, PAD2 shown at FIG. 5A has a zone of attachment means shown at zone, ATM2 which allows it to be attached to the surface of the pad, PAD1 on a detachable re-attachable basis. Importantly, the body of the first pad as shown in this figure at pad means PAD1 may be made from a laminated means which is shown at FIGS. I and II. This pad means use support, SUP which again in this model is shown at PAD1 for protecting the lower elbow and the wrist from being hurt by the pressure from the landing object such as table or handle of a chair.

FIG. 6. Shows symbolically a stretchable panty hose means, Stretch Panty Hose, which is designed, to be worn in order to stay on the lower body, and to cover, the thigh, the knee, and ankle area and to have a band, Band to prevent from being pulled away from the foot. The body of this panty hose means has zones or strips of hook fastener attachment means, ATM2 in the sides which allow a strap means made from Lycra to be attached to it on a detachable, re-attachable basis. The hose or the panty hose in that matter may have more than one of these strings in its body for example one in front, one in back and one in each side. So that the combination allows the hose to expand side wise but not to be pulled down from the belt or the extension of the belt or similar.

Importantly, this unit may be made with only some parts such as a unit for the leg, a unit for the leg and knee, a unit for the thigh area only or a more complete unit to cover from the foot, leg, knee and thigh area and even the abdominal site. Now there is a need for preventing the hose from falling and for this purpose a suspender system, shown at FIG. 6A is designed that will use the belt or event will have vertical straps that will stand on the shoulder area so that by attaching those to the hose means it will prevent the body of hose from falling.

Importantly, the figure shows that the panty hose has a string or band of a non-stretchable material, Non-Stretch-Strip, that is embedded or attached to the body of the hose so that it will prevent from shrinking pulling the panty hose toward the feet along the vertical line in standing. Since the end of this band is attached to the belt, Belt and thus the belt will prevent this line to move down. Importantly, this non stretch string can be pulled to shorten and to match the height of the limb. The attachment spot on the belt is adjustable and allows such change from top. Also it may be pulled in the foot side. The combination will prevent the strap means from moving down toward the feet. The strap means then will apply most of the compression to the limb. This line or a line adjacent to it will be the site that the long zone of hook fastener attachment means, ATM2 will be sewn, adhered or attached. The unit may have independent zones of attachment means for the knee areas to stand in the sides of the knee. These zones may be adhered or attached later on when the person has worn the hose and the site for these hook fastener attachment means are decided. The zones of hook fastener attachment means, ATM2 in the thigh area will be attached to the lateral and medial sides of this hose as shown. Although the unit may also have other zones of hook fastener attachment means as well. The thigh hose may be attached to a belt or be part of a panty hose. Importantly, in the prototype model a stretchable panty hose is used that is capable of accepting the hook fastener attachment means, ATM2 on a detachable, re-attachable basis. In this model the outer surface of the panty hose is capable of accepting zones of double sided hook fastener attachment means, ATM2-DS that is made from a relatively, rigid material which has layers of hook fastener attachment means, ATM2, in each side, so that first zone, will attach to the outer surface of this panty hose and the second zone will be available to accept the strap means, STR on a detachable, re-attachable basis. The zones of double sided hook fastener attachment means, can be made in different shapes and sizes, however in the prototype model they are about ¾ of inches by 8-10 inches with the inner surface having more surface covered with ATM2 than the outer surface so that at the time of removal of the strap means, the double sided hook fastener attachment means will not separate from the panty hose. An example of the double sided hook fastener attachment means, DS-ATM2 is shown in FIGS. 16, 16A and 16B. This unit has a body made from a relatively rigid layer, Rigid Layer which the body will prevent this unit from bending and shrinking. The outer/upper surface of this piece has a zone of hook fastener attachment means, ATM2-A which has a lesser grip/or a lesser aggressiveness and the lower/rear surface has a hook fastener attachment means, ATM2-B which is more aggressive and has more grip/and or more surface. This piece will be attached to the outer surfaces of the panty hose or a support on a detachable, re-attachable basis, but it would need more force to be separated from the support. Also please note that the size of the zones of the attachment means also varies or may vary. The outer/upper surface of this piece has a lesser percent of hook fastener attachment means, ATM2-A while the lower/rear surface is totally covered with the more powerful, hook fastener attachment means, ATM2-B. This design will provide more aggressive attachment to the support or panty hose and less aggressive attachment to the strap means. Thus this allows the strap means, STR to be attached to the outer surface of the DS-ATM2 on a detachable, re-attachable attachment, basis but to be released easily without the DS-ATM2 being disengaged from the outer surfaces of the support or the panty hose. Importantly, the use of zones of the hook fastener attachment means, DS-ATM2 with the support means that has an outer layer with loop fastener attachment means, ATM1 allows the DS-ATM2 pieces to be removed, cut, re-positioned etc. Importantly, the hose means does not need to have an outer layer to be from loop fastener attachment means, but it will have zones of the hook fastener attachment means, ATM2 in order to allow the strap means to be attached to them.

Importantly, if the size and shape of the hose means depends on the size and shape of the area. For example
1. For the leg it will have a size that will fit up to the knee.
2. For the feet and leg it will have a size that fits the feet and up to the knee.
3. For the feet, leg and knee it will have a size that fits the, feet, leg, knee and above knee, with connection to the belt area to prevent it from falling. Or can be a panty house.
4. For the feet, leg, knee and thigh it will have a size that fits the feet and up to the upper thigh area with connection to the belt area to prevent it from falling. Or can be a panty Thus the size and shape will follow a reasonable design in order to hold the strap means securely.

Importantly, the liner of the panty house may be made to be adjustable so that its edges can be attached to each other on a detachable, re-attachable basis. This method will allow the size of the unit to be decided.

FIGS. 7 & 8. Shows symbolically a method of combining the elastic hose means with strap means for the purpose of making a system for covering from the foot to the upper thigh area. In this method the system consist of 1. A stretchable hose means, Stretch Panty Hose shown at FIGS. 6 and 6A designed for being worn for covering from the foot to the lower trunk area. This hose means has a body made from a stretchable material that is
  a. Capable of attaching to the hook fastener attachment means, ATM2 or similar on a detachable, re-attachable basis. For example when the hose system is made from Lycra with its shiny face outside.
  b. Even if the body of the panty hose does not attach to the hook fastener attachment means, ATM2 directly it Will have zones of hook fastener attachment means, ATM2 or similar attached or adhered to it. As shown on its body in order to allow the strap means such as the STR-L & STR-T shown at FIG. 7 to be attached to it on detachable, re-attachable basis.
  c. Any other attachment means that complements the strap means.

This unit with the attachment means, ATM2 or similar allows a special strap means to be attached to it on a detachable, re-attachable basis. In one model the strap means consist of two pieces as shown at FIG. 7.

A1. A strap means which is a long piece of Lycra which the initial segment of it as shown at STR-L and STR-T with the shiny face toward the body of the person when wrapped. Thus these are made from a stretchable fabric that functions as a stretchable, loop fastener attachment means to attach to it on detachable, re-attachable basis. This strap means not only is a stretchable fabric but also it functions as a loop fastener attachment means in one of its side which is shiny. So that any part of this strap means in the shiny side is capable of attaching to a matching hook fastener attachment means, ATM2, on a detachable/re-attachable basis. This is a very crucial and important property that makes this unit unique and allows the intended use possible. The dull side on the other hand attaches to a hook fastener attachment means, ATM2, on a detachable/re-attachable basis with a much lesser grip, there is possibility that this property or the ATM2 to be modified to make the engagement more aggressive. The properties of this strap means is explained in the text. Importantly, this can be altered. For example
I. The fabric may be sewed to be double sided to accept attachment means in both sides. II. To be modified in order to allow the hook fastener attachment means to be attached to this strap on both of its surfaces on a detachable, re-attachable attachment means. III. The fabric may be changed to have zones of loop fastener attachment means, ATM1 on its dull surface and modify it so that it will allow the hook fastener attachment means, ATM2 to attach to it on a detachable, re-attachable basis. This will be similar to the fabrics that has many patches of raised flowers or special patterns etc. Importantly, these zones may be woven to the fabric or they may be adhered or attached to the outer surface of the LYCRA™ by various means. The advantage of this modified strap means is that it allows the end piece of the strap, ATM2 to be attached to any part of the outer surface of the strap means, STR1-2 on a detachable, re-attachable attachment means, and this prevents the end of the strap means to be loose. This provides a great advantage in handling the unit made from this strap for the purpose intended in this application and similar units. The advantage is that the coming strap after wrapping a limb will attache to the outer surface of its own and will be more stable and will not slip. Also it allows wrapping of the strap over itself multiple times without allowing it to slip. The support will hold the strap in position securely and prevent it from moving.

A2. The later part STR-LF and STR-LT are also made from the same material as STR-L except in this part the shiny surface is out. When the length of this segment of the strap are chosen properly, the end of these straps which has hook fastener attachment means, ATM2-F, will wrap and come in contact with the shiny outer surface of the segment of straps at the later part STR-LF and STR-LT. Importantly, this method allows the end piece. ATM2-F of each strap to attach to the outer surface of the matching, STR-LF or STR-TF on a detachable/re-attachable basis and to have the end piece under control.

Method of Use.
1. Initially the user wears the panty hose and keeps it in comfortable position. 2. The user attaches one end of the strap means to a zone of loop fastener attachment means, ATM1 on the panty hose or to the body of the panty hose, in lower leg close to the ankle. 3. The user will then wrap the strap STR-L around the leg obliquely moving up while pulling the strap, so that finally it reaches to the knee area. In the knee area the strap will finish with the hook fastener attachment means, ATM2 of the leg and will wrap around the knee to attach to the lower end of the hook fastener attachment means of the thigh, so that it will cover the knee and the popliteal area will not be unwraped. In each wrap the inner surface of the strap, STR-L will attach to the ATM2 of the panty hose till the STR-F comes and the end of this segment will attach to it on a detachable, re-attachable attachment means. The strap may be long enough to cover the knee area and attach to the panty hose above the knee. In cases which there is one very long strap means, (this still has the both segments of the strap means) the strap means will be wrapped to cover the leg, knee and the thigh area and may reach the lower trunk if needed.

The end of the strap shown at ATM2 made of hook fastener attachment means or similar unit has capability to attach to the outer surface of the strap on detachable, re-attachable attachment basis.

The user will also attach the thigh strap, STR-T in similar fashion by attaching one end of the strap means to a zone of loop fastener attachment means, ATM1 on the panty hose or to the body of the panty hose, in the lower thigh area close to the ankle. Or may attach it to the outer surface of the leg strap which may have a zone of ATM1.

Then the user will then wrap the strap STR-T around the thigh obliquely moving up while pulling the strap, so that finally it reaches to the upper thigh area. So that it will cover the thigh totally and gets close to the groin area, in each wrap the inner surface of the strap, STR-T will attach to the ATM2 of the panty hose till the STR-TF comes and the end of this segment will attach to it on a detachable, re-attachable basis. Importantly, the unit may only use one very long strap similar but longer than the strap, STR-L—STR-LF so that it will wrap around the leg, to cover the knee and thigh area completely. FIG. 8. Shows symbolically the unit shown at FIG. 7 with a series of stretchable, strap means, attached to the hose and its related attachment means for thigh area and the three lower strap means, STR4-6 are attached to the leg area. This method allows these straps to wrap horizontally, to the limb and attach to the ATM2 zones of the panty hose on detachable, re-attachable basis. The design of these straps will allow the end piece to attach to the outer surface of each strap so that each strap will be secure. The end part of strap means may have a segment that is shiny as shown in previous figure. Importantly, in some models the strap means may only go to half way of the hose and to attach to the hook fastener attachment means, ATM2 in the middle and then to return and attach to the rear surface of its own. Thus by pulling the attachment means to pull the front half of the hose means and to make the hose unit tight.

FIGS. 9 and 10, shows schematically a shaped support unit for the leg which consists of a relatively rigid but flexible support, which is shaped to stand on the leg, ankle and feet area. When in place this unit would not shorten, but would be able to twist to the sides and also is able to bend in the ankle joint area to allow a joint function.

This unit can be a single piece or may consist from combination of two or more pieces. In this prototype model the unit consist of a leg piece and an ankle-foot piece that are attached to each other on a detachable/re-attachable basis at separation point, SEP. The purpose of this unit is to use this unit as a support means as mentioned in previous units for stabilizing the strap means and preventing them from moving and falling. Also to use the body of the support in an area such as ankle for compressing the soft tissues of the sole and ankle area and prevent the hydrostatic pressure to squeeze fluid out of the vessels into the tissue in this area. In this system the upper part of the support, UP has a curvature which matches the rear surface of the leg in the calf area. The support moves down attaches to the ankle-feet pieces and stands in the Achilles tendon area and then has flaps with special cuts and shapes that will fill the part of the ankle rear to the inner and outer malleolus area. Also in the sole area the inner/medial part of this unit has a curvature and padding that will fill the inner arch of the foot for supporting that part of the foot for two reasons.

1. For supporting the arch of the feet.
2. For supporting the soft tissue of the area in order to prevent from hydrostatic pressure to squeeze the fluid out of the vessels.
3. The ankle-foot piece also plays a crucial role in stabilizing this unit by preventing the leg support from sliding and moving down. This function come to be important particularly, when the shape of the leg of the person is so that the calf muscle are not prominent and do not bulge out in order to prevent from the upper strap for preventing the support from moving down.

Importantly, the support is designed to have a series of stretchable straps, attached to its body in one side and allow the stretchable straps to be pulled from one side of this support to attach to the other side on a detachable/re-attachable basis. In order to wrap around the leg for protection, compression and support. This unit will use a series of straps which will be attached to it or will go over this unit in order to provide the constriction and support of the tissue. The straps are not shown in this figure but in next figure. In this figure the upper part has a curvature and shape shown at UP for matching and fitting the calf of the user. The part shown at HP is to stand on the Achilles tendon area. The medial and lateral flaps shown at MT and LT will stand on the area above the medial and lateral malleoluses. The flaps that stand in the area bellow the medial and lateral malleoluses are shown at MP and LP. The piece that stands under the arch of the sole is shown at SS and the sole piece shown at SP, which will stand under the sole area. The prominent part of the malleolus is shown at MM.

Importantly, when in place and the straps are wrapped around the feet and lower leg, this unit will exert its power to compress and hold the soft tissues of the feet, ankle and lower leg by virtue of its own body and curvature, presence of lining and shaped pads.

Importantly, this support part of this unit may be made from combination of two or more pieces that can be detached and re-attached as desired. The connection between these can be with use of various methods, and the straps of each unit can be independent. This system may support other units such as 1. Measurement means of various forms in order to allow the pressure in area to be known. 2. Electrical stimulators which can be placed in order to stimulate the nerves or muscles. 3. Wound dressing of various forms, gels, antibiotics, healing materials etc. 4. Wound support units of various forms. 5. Wound or tissue protectors of various forms, for prevention of problems. 6. Air pumps in order to allow the pressure to be modified in any form. The support of these units may be also further enhanced by the use of the layers for protection of the tissues. Importantly, The use of these straps for the support of knee and other lower joint will have a suspender that will be attached to a belt and this belt will allow the knee support to be hold in place without using the constricting effect of the straps which can cause strangulation of the tissue and limb and complications.

FIG. 10. Shows schematically the front view of the support unit shown at previous FIG. 9. In this figure the upper part is shown at UP. The lower piece in the bottom and the separation point at SEP.

The support moves down and reaches the ankle piece and shows its two flaps, lateral flap, L-FLAP and the medial flap, M-FLAP. These flaps will be pulled by the stretchable straps (the stretchable straps for this part is not shown at this figure) to be attached to the other flap, above the internal and external Malleolus. The part that stands on the Achilles tendon area is seen. Then the lower flaps are shown, the sole part is shown at SOLE and it has the raised part that will fill the curvature of the arc of the s shown at SOLE-PAD.

This unit will use a series of straps which will be attached to it or will go wrap around over this unit in order to provide the constriction and support of the tissue. In this FIG. 3 straps, STR1, STR2 and STR3 attaches to one side of support on a fixed base then are sized to wrap around the leg and attach to a zone of attachment means ATM2 on this support on a detachable/re-attachable basis. Importantly, the unit will also use similar stretchable straps that will attach to the malleolus and the feet part of this unit, being fixed on one side of the support going to attache on the other side of the support on a detachable, re-attachable basis. These straps are not shown in this figure.

Importantly, the sizes and the shapes of the straps will vary in order to serve the purpose in a more meaningful fashion, for example the strap, STR2 may have a wider size in order to overlap the straps, STR1 and STR3. Also the straps, STR1, STR2 and STR3 may also have triangular shapes as shown at FIG. 15 in order to overlap each other and prevent from having a portion of the leg uncovered and bulged out.

This design is very important, since it makes an stretchable fabric means which will overlap each other and prevent from having a portion of the leg uncovered to bulge out. An uncovered area of the leg, or thigh or similar place can create a functional problem when one portion of a vessel such as vein is pressed and the portion before that is not covered. This will cause a segment of the vein to be engorged, the blood inside it to be stagnant and to have a set of for blood clot formation and phlebitis which will be very dangerous.

The straps not only will cover the ankle area but also the feet over the important vessels in order to allow a continuous compression from the feet, ankle and leg area which can be continued to also cover the knee and the thigh area for a complete coverage. Importantly, these strap means may be also added to various braces that can be used in the leg and/or feet areas in order to make toleration of these units much easier and comfortable. FIG. 11. Shows schematically a somewhat different method of supporting mechanism, designed to prevent from the sliding and falling of the strap means from the thigh and legs. In this method again a relatively rigid but flexible support means, SM which doe not shorten but can bend to some degree, would allow the unit to bent at popliteal area but would not allow the straps to move down. This unit is shaped to stand in the rear surface or the sides of the thigh and would move down the leg, then will turn to move in the ankle area to connect to a plate, PLT that stands in the sole of the foot. By this method this support means will not be able to move down since the plate, PLT will prevent from doing such. A series of stretchable straps means are connected to the support means, SM in the following fashion.

1. A thigh strap, T-STR will wrap around the lower thigh, this strap can not move down due to the function of the support means, SM
   also due to the presence of the prominence of the knee cap. This strap means can be more than one strap and consist from three or more.
2. An upper leg strap means, STR1 which will wrap around the upper leg. This strap means will not be able to move down due to the connection to the support means, SM and the function of the support means, SM also due to the presence of the prominence of the calf muscle.
3. A mid leg strap means, STR2 which will wrap around the middle leg. This strap means can not move down due to the connection to the support means. 4. A lower leg strap means, STR3 which will wrap around the lower leg. This strap means can not move down due to the connection to the support means.
5. Importantly, the plate will be kept in place due to the use of strap means of its own, such as the foot strap, F-STR. This method will be quite useful in keeping the strap means in place from the thigh area to the leg. Also importantly, this figure is to illustrate clearly that the strap means can overlap each other which is very important issue in preventing the a portion of the leg, thigh to be unprotected. Importantly, the unit will be functional in most of the cases even if the support means did not extend to the feet, since the prominence of the ankle by itself will prevent from the leg unit and the support to move down.

FIG. 12. This figure shows schematically a support mechanism which is designed to support the strap means in the thigh, leg and ankle-feet area. In this model the unit consist of 1. A belt means, BELT made from a non-stretchable material will stand in the belt area and allows a vertical piece, VP to be attached to it on a detachable/re-attachable and adjustable basis. The belt means, BELT will prevent the vertical piece, VP from moving down.
   due to the natural function of the belt in this area and presence of the bones.
2. A vertical piece, VP made from a non-stretchable material which moves down from the belt, BELT and attaches to the joint means at hip area, HJ and attaches to the support means for the thigh, T-SUP. This piece will prevent the thigh support, T-SUP from moving down. Since the belt means, BELT will not allow. Thus the hip joint means, HJ stands between the vertical piece, VP and the thigh support, T-SUP.
3. A thigh support, T-SUP which is made from a relatively, non-stretchable material which functions as the support piece in the thigh area and will move down from the piece for the hip joint, HJ and attach to a joint means in the knee joint area, KJ. This support, T-SUP allows multiple strap means to be attached to it on a detachable/re-attachable basis. The T-SUP piece will prevent the leg support, L-SUP from moving down, due to its attachment to the belt mean, BELT, by use of VP.
4. A leg support, L-SUP which is made from a relatively, non-stretchable material which will function as the support piece in the leg area and moves down from the joint means for the knee joint, KJ and attaches to the ankle-feet piece in ankle joint area, AJ. This support, L-SUP allows multiple strap means to be attached to it on a detachable/re-attachable basis. This piece will keep the straps in stable condition and prevent them from moving down, due to its attachment to the belt mean, BELT, by use of VP and the thigh support, T-SUP.
5. An ankle-feet support, AF-SUP made from a relatively, non-stretchable shaped material as explained earlier in this application and this unit will prevent the leg support, L-SUP from moving down. The shape of ankle-feet support, AF-SUP matches the shape of the anatomy of the area and it stands in the ankle-foot area and move down to the sole area and will be kept in place by use of series of strap means not shown here. These strap means not only will hold this piece in place but also will compress the soft tissue of the ankle-feet area.
6. Importantly, a series of functional joint means such as the HJ, KJ and AJ are utilized in this unit in order to allow the upper and lower pieces to rotate in these joints. These joint means can be a spring means, a relatively, thin polymer or any other means that can be utilized in these areas that allows the unit to be held yet to function as a joint.

7. A series of connection means such as CP are designed to allow the two pieces of the supports to be attached to each other on a detachable/re-attachable basis.

This allows only one support or more to be utilized if needed.

Importantly, the unit will be functional even if the support means did not have the ankle foot support, AF-SUP, since the connection to the belt means, BELT will prevent from the supports to move down.

FIG. 13. Shows schematically a support means designed for wound dressing of the ankle area. This unit is a modified version of a unit which is shown in this application for the wound dressing of the ankle and consists of.

1. A support means, SUP designed to stand in front of the very lower leg and/or the upper part of the ankle and upper part of the foot as shown. The support means, SUP is made from a non-stretchable layer similar to the supports which are explained in this application previously.

In this prototype model the support, SUP is made from a laminate, with a surface made from ATM1 that allows the hook fastener attachment means, ATM2, to be attached to it on detachable/re-attachable basis. A soft lining for being placed on the skin or cover of a wound and a layer of a foam sandwiched in between as it is explained more in this application.

The support means, SUP, has a rectangular shape, has a long, narrow zone of hook fastener attachment means, ATM2-SUP on its border that allows a strap made from Lycra,™ or a zone of loop fastener attachment means to be attached to it on detachable, re-attachable basis. Also Importantly, the end of the strap, has a zones of hook fastener attachment means, ATM2-STR that attaches to the outer surface of support, SUP, on a detachable/re-attachable basis. Please note that in this model the support, SUP is made from a laminate, with a surface made from ATM1 that allows the hook fastener attachment means, ATM2, to be attached to it on detachable/re-attachable basis. The end of the strap means, ATM2-STR is cut to function as tongues, here the unit has 3 such tongues, that allows each one to be pulled and attached to the out surface of the support, SUP, independently, which makes the adjustment easy.

Importantly, this method will make a double attachment means that allows a very unique and stable attachment of the strap, STR, to the support, SUP, on a detachable/re-attachable basis and makes the attachment of the strap to support far more easy.

2. A rather wide strap means, AS, made from an stretchable fabric, LYCRA™, which is shaped and sized to conform around the ankle and attach to the support, SUP, by use of a zone of hook fastener attachment means, ATM2-SUP on a detachable/re-attachable basis. The body of the strap, AS, functions as the loop fastener attachment means and attaches to the zone of the ATM2-SUP on a detachable/re-attachable basis.

3. A special piece, SP, made from a material such as a layer of latex which is attached to the body of the strap means, AS in order to conform the strap means, AS, to shape it as desired and make it to accept the heel and fit the heel easily. By doing so, it will secure the position of the strap means, AS in the heel and will allow an easy placement of this unit on the heel. So that the strap means, AS can be easily pulled to be attached to the hook fastener attachment means, ATM2-SUP of the support, SUP. Thus by doing so the whole placement of this unit will be easier and the unit will stay on the area more securely, since the shaped, special, piece, SP, will not allow the unit to move to sides while it is being kept in place by the stretchable strap means, AS.

Importantly, this method plays a crucial rule in keeping such units in prominent areas such as heels, knees, shoulder, scalp, elbows, and any similar places. This idea was previously explained to be utilized in other areas such as the knee and can be used in any other site that can be utilized.

Importantly, the shaped piece may be embedded to the body of the strap, or it may be attached to it by various means. It may have a body made from a screen of latex or similar material or it can be a shaped, stretchable layer. Importantly, it may be made in any form, shape or material that will serve this purpose. Importantly, the specail piece, SP, can be attached to the body of the strap means, AS on a permanent or detachable/re-attachable basis.

Method of Use.

1. At the time of use initially the applicant will place the special piece, SP, from this unit on the heel of the person.
2. Then will pull the support, SUP, gently to place on the upper surface of the ankle, foot area. Please note that the support, SUP is attached to the strap means, AS.
3. The applicant will then pull end pieces, ATM2-STR of the strap, AS and attach the body of the strap, AS to the attachment zone ATM-SUP of the support means, SUP on a detachable/re-attachable basis and will continue to pull the rest of the end pieces ATM2-STR to the support in a similar way.
4. Then the applicant will pull the end pieces, ATM2-STR of the strap, AS and attach them to the outer surface of the support means, SUP on a detachable/re-attachable basis and will continue to pull the rest of the end pieces ATM2-STR to the outer surface of the support in a similar fashion.

FIG. 14. Shows schematically a non stretchable support means which is long for use in long limbs such as legs, arms and thigh etc. This unit has the same properties mentioned previously for the support means.

In this figure a long non stretchable layer shown at SUP has at least one long zone of attachment means shown at ATM2-A that allows a matching piece or a strap to be attached to it on a detachable/re-attachable basis. In this particular unit the support, SUP, has also another of such long zone of attachment means shown at ATM2-B as well.

FIG. 15. Shows schematically a support means for the leg or any long limb that consist of the following:

1. A non stretchable support piece, SUP shown at previous FIG. 14 that allows the straps to be attached to it, on a detachable/re-attachable basis.
2. A trapezoid stretchable strap means shown at, STR1 made from an stretchable fabric that is fixed to the left, long side of the support, SUP, and is designed to wrap around the upper leg and the body of this strap means, STR1 to attach to the ATM2-A of the support means, SUP on a detachable/re-attachable basis. The fixed part of this strap means may be attached to the support, SUP, on a permanent or detachable/re-attachable basis. The free end of this strap means, STR1 may attach to the zone of hook fastener attachment means shown at ATM2-B of the support, SUP, on a detachable/re-attachable basis, per specific design. Importantly, in this model the strap means, STR1, is made from LYCRA,™. Alternatively, it may be made from another type of stretchable fabric with a zone of attachment means, at its end in order to make the attachment to the support means, SUP or the zone ATM2-B possible.

Importantly, the rear/bottom surface of the strap, STR1 may have a zone of loop, fastener attachment means, ATM1 shown in a zone with dotted line around it. This is for use if the strap, STR1 does not have the property to attach to the zone of the hook fastener attachment means shown at ATM2-A and ATM2-B of the support means, SUP, by its own properties such as the Lycra.™ does.

3. A second trapezoid stretchable strap means, shown at STR2 made from a similar stretchable fabric is also fixed to the left, long side/border of the support means, SUP, and is designed to wrap around the lower leg and to attach to the ATM2-A on a detachable/re-attachable basis. Again the fixed part of this strap may be attached to the support means, SUP, on a permanent or detachable/re-attachable basis. The end of this piece may also attach to the zone of hook fastener attachment means shown at ATM2-B of the support, SUP, on a detachable/re-attachable basis, per specific design. Importantly, please note that in this model the strap means, STR2, is made from LYCRA,™. Alternatively, it may be made from another type of stretchable fabric with a zone of loop fastener attachment means, at its make the attachment to the support means, SUP or the zone ATM2-B possible.

Importantly, the rear surface of the strap, STR2 may also have a zone of loop, fastener attachment means, ATM1 in case the strap means does not have the property to attach to the zone of hook fastener attachment means shown at ATM2 of the support, SUP, by its own properties such as the Lycra.™ does. 4. A third trapezoid stretchable strap means, shown at STR3 made from a fabric which is also fixed to the left, long side/border of the support means, SUP, and is designed to wrap around the whole leg over the strap means, STR1 and STR2 and attaches to a zone of hook fastener attachment means, ATM2-C, located on the rear/outer surface of the strap means, STR3 along its base, on a detachable/re-attachable basis. The zone, ATM2-C is a long zone of attachment means that allows the body of the fabric, STR3 or its end piece to be attached to it on a detachable/re-attachable basis. Importantly, in this model the strap means, STR3 is made from LYCRA,™. Alternatively, it may be made from another type of stretchable fabric with a zone of attachment means, at its end. This design is very important, since it makes a stretchable fabric means which will overlap the other strap means STR1 and STR2 and prevent from having a portion of the leg uncovered to bulge. An uncovered area of the leg, thigh or similar place can create a functional problem when one portion of a vessel such as vein is pressed and the portion before that is not covered. This will cause the uncovered vein to engorge, the blood inside it to be stagnant and to have a set of for blood clot formation and phlebitis which is very dangerous. Importantly, similar units may be also made for the use in the arm, elbow and thigh areas and any other place that can be utilized.

Method of Use.

At the time of use, the support will be located in the shin area of the leg, although, it can be placed in the side of the leg or even in the back particularly, when the unit is designed to be used with use of supports as shown in previous figures. Then one of the smaller trapezoid strap means such as strap, STR1 will be wrapped around the upper leg and will be pulled to be attached to the upper part of the attachment zone, ATM2-A of the support, SUP, on a detachable/re-attachable basis, then it may be pulled more to be also attached to the attachment zone, ATM2-B of the support, SUP, on a detachable/re-attachable basis. In second step, the second smaller trapezoid strap, STR2 will be also pulled to wrap around the lower leg, and will be pulled to be attached to the lower part of the attachment zone, ATM2-A of the support means, SUP, on a detachable/re-attachable basis.

The end of this strap may be also pulled more to be also attached to the lower part of the attachment zone, ATM2-B of the support, SUP, on a detachable/re-attachable basis. The extra pieces may be trimmed.

At the third move the user will pull the large trapezoid strap, STR3 in the direction opposite to the direction which the first and second straps to wrap over those two straps, STR1 and STR2. Then will pull to attach to the attachment zone, ATM2-C of the unit, on a detachable/re-attachable basis. This strap will mostly cover the end pieces of the previous two straps, STR1 and STR2 and will father cover and support the areas of the leg which the straps means, STR1 and STR2 have not covered. This will leave a smooth finish on the leg.

Importantly, when this unit can be made with use of methods that allows the pressure in the system to be verified, such as straps with pressure sensing capabilities, the balloon system with gage etc. Then it will allow the choice of pressure which these supports can deliver to the limb. Importantly, the large trapezoid strap, STR3 can be also pulled in the same direction as the first and the second strap means, STR1 and STR2 in order to be attached to the second zone of the attachment means, ATM2-B of the support on a detachable/re-attachable basis. If this is chosen then the end pieces of the straps means, STR1 and STR2 will not be attached to the zone of the attachment means, ATM2-B of the support. Importantly, similar units may be also made for the use in the arm, elbow, thigh, chest, abdomen and any other place that can be utilized.

FIGS. 16, 16A and 16B. Shows schematically the front view of a double sided hook fastener attachment means, ATM2 which has a body made from a relatively rigid layer, Rigid Layer which the body will prevent this unit from bending and shrinking. The outer/upper surface of this piece has a zone of hook fastener attachment means, ATM2-A which has a lesser grip/or a lesser aggressiveness and the lower/rear surface has a hook fastener attachment means, ATM2-B which is more aggressive and has more grip/and or more surface.

The use of pad means with these units.

Importantly, pad means may be used with these units in order to allow a particular area to be compressed more than the others. In this method a pad means, made from different material may be used to be attached or adhered to the skin and then to have the hose to be worn on top of that and then the strap to be wrapped around the hose. Importantly, the hose means may have a raised area such as a commonly used ECG pad that initially will be placed on the site of operation and then the hose to be cut to remove the pad, to perform procedure, then to place the pad and wrap the strap means on the pad means.

FIG. 17. Shows few pad means designed for use with these supports for various reasons. The pad means may be made from different materials and means and they also may have different sizes, shapes, thickness and stiffness and other important characteristics. They may be made from inflated or inflatable balloons. They may be made for being attached to the support and the straps in order to be placed under the support and over the wound for various reasons. These pads may be made.

1. A padding with various body, gauze pad, absorbent etc.
2. A balloon with various shapes such as the flat, more round etc.
3. An inflatable balloon that allows the pressure inside the balloon to increase.
4. A shaped balloon, or pad. To apply certain compression in wound.
5. A medicated pad. To deliver medicine to the person.
6. An absorbent pad to allow the drainage of the wound to be absorbed.
7. A sticky pad to adhere to the wound.
8. A pad with nonporous membrane such as vinyl.
9. A pad which has an adhesive tape.
10. Heated pad or cold compresses.

The pad means have a attachment means such as the ATM-X that allows the pad means to be attached to the support or strap means. The attachment means can be of various forms such as; adhesive, snaps, fastener means, bands etc. So that it can allow the pad means to be re-positioned or exchanged. Also importantly, the pads may be attached to the wound area by adhesives or bands so that then the support can be placed on them and compressed. Importantly, the pad may have different thickness or consistency for applying different level of pressure to the wound. Example of this is shown in right side, this unit has a smaller, thicker central piece shown with a dotted circle and a thinner, or softer larger piece shown in large circle. Such a unit allows the center of the wound to be compressed more. Different sized or shaped units may be made for other uses. The characteristics of these pad may vary in many ways to satisfy different needs. Also Importantly, the pads may be made to be medicated pads, in order to deliver medication to the wound. Also they may provide heat or cold to the wound by use of heated pads, heated units or cold compresses.

FIGS. 18-19 shows the use of hand held applicators with the long strap means for an easy delivery. The use of these units allow the strap to be applied to the limb and also removed from the limb with ease. Two models of these units are shown in this application.

What is claimed is:

1. A wrap for encircling and compressively wrapping a portion of a living body, the wrap comprising:
    a relatively non-stretchable support;
    a strap having a length extending from one lengthwise end, which is attached to the support, to an opposite lengthwise end;
    the one lengthwise end being attached to the support by hook-type attachment material detachably/re-attachably attaching to loop-type attachment material;
    a length of relatively stretchable material forming at least a portion of the length of the strap and having an outer face for facing away from the portion of a living body when the wrap is encircling and compressively wrapping the portion of the living body and an inner face for facing toward the portion of the living body when the wrap is encircling and compressively wrapping the portion of the living body;
    the inner face of the relatively stretchable material possessing a loop-type fastening characteristic capable of detachably/re-attachably attaching to hook-type fastener material;
    and at least one piece of hook-type fastener material disposed on the outer face of the relatively stretchable material of the strap at a location that provides for the inner face of the relatively stretchable material to directly detachably/re-attachably attach to the at least one piece of hook-type fastener material by surface-to-surface contact after the strap has encircled the portion of the living body.

2. A wrap as set forth in claim 1 comprising multiple pieces of hook-type fastener material attached to the outer face of the strap at various spaced apart locations along the length of the strap.

3. A wrap as set forth in claim 2 further comprising multiple pieces of loop-type fastener material attached to the outer face of the strap at various spaced apart locations along the length of the strap.

4. A wrap as set forth in claim 3 wherein one of the pieces of loop-type fastener material attached to the outer face of the strap is located at the one lengthwise end of the strap, and another of the pieces of loop-type fastener material attached to the outer face of the strap is located at the opposite lengthwise end of the strap.

5. A wrap as set forth in claim 4 including one piece of hook-type fastener material which is located at the one lengthwise end of the strap on the inner face of the strap and which attaches the one lengthwise end of the strap to the support, and another piece of hook-type fastener material located at the opposite lengthwise end of the strap on the inner face of the strap.

6. A wrap as set forth in claim 1 wherein the relatively non-stretchable support contains hook-type fastener material on an outer face thereof, and at the one lengthwise end of the strap, the inner face of the relatively stretchable material attaches to the hook-type fastener material on the outer face of the support on an attachable/de-tachable basis.

7. A wrap as set forth in claim 6 wherein the outer face of the support also contains loop-type fastener material, and the strap comprises hook-type fastener material at one or more locations along the length of the strap in the direction away from the one lengthwise end for enabling the strap to attach to the loop-type fastener material on the outer face of the support.

8. A wrap as set forth in claim 7 wherein the relatively non-stretchable support has a long dimension in the direction of the length of the portion of the living body when the strap is encircling the portion of the living body.

9. A wrap as set forth in claim 8 wherein the inner face of the relatively stretchable material attaches to the hook-type material on the outer surface of the support proximate one lengthwise end of the support, and a ring is attached to the opposite lengthwise end of the support.

10. A wrap as set forth in claim 1 in which the outer face of the relatively stretchable material of the strap possesses a loop-type fastening characteristic capable of detachably/re-attachably attaching to hook-type fastener material.

11. A wrap as set forth in claim 10 further comprising at least one piece of hook-type fastener material disposed on the inner face of the strap.

12. A wrap as set forth in claim 1 in which the one lengthwise end attached to the support by hook-type attachment material detachably/re-attachably attaching to loop-type attachment material comprises hook-type attachment material on the support and loop-type material on the strap.

13. A wrap as set forth in claim 1 in which the one lengthwise end attached to the support by hook-type attachment material detachably/re-attachably attaching to loop-type attachment material comprises loop-type attachment material on the support and hook-type material on the strap.

14. A wrap for encircling and compressively wrapping a portion of a living body, the wrap comprising:

a relatively non-stretchable support; and a strap having a length for encircling the portion of the living body and
A) that has lengthwise opposite ends, one of which is attached to the support,
B) that is relatively stretchable along its length for compressively wrapping a portion of a living body,
C) that has an outer face for facing away from the portion of the living body when the strap is encircling and compressively wrapping the portion of the living body and an inner face for facing toward the portion of living body when the strap is encircling and compressively wrapping the portion of the living body;
D) that along a first lengthwise segment comprises stretchable material that presents, as the outer face, a loop-type fastening characteristic capable of detachably/re-attachably directly attaching to hook-type fastener material; and
E) that along a second lengthwise segment comprises stretchable material that presents, as the inner face, a loop-type fastening characteristic capable of detachably/re-attachably directly attaching to hook-type fastener material;

further including
F) at least one piece of hook-type fastener material attached to the inner face of the first lengthwise segment;
G) at least one piece of hook-type fastener material attached to the outer face of the second lengthwise segment;
H) one piece of hook-type fastener material which is disposed on the inner face of the first lengthwise segment at the one lengthwise end of the strap and which attaches the strap to the support; and
I) one piece of hook-type fastener material attached to the outer face of the second lengthwise segment located at the lengthwise end of the strap which is opposite the one lengthwise end of the strap.

15. A wrap as set forth in claim 14 wherein
the stretchable material of the first lengthwise segment presents, as the inner face, a loop-type fastening characteristic capable of detachably/re-attachably directly attaching to hook-type fastener material; and
the stretchable material of the second lengthwise segment presents, as the outer face, a loop-type fastening characteristic capable of detachably/re-attachably directly attaching to hook-type fastener material.

16. A wrap as set forth in claim 15 further including:
a piece of hook-type fastener material attached to the outer face of the first lengthwise segment substantially at the one lengthwise end of the strap which is attached to the support; and
a piece of hook-type fastener material attached to the inner face of the second lengthwise segment substantially at the lengthwise end of the strap which is opposite the one lengthwise end of the strap.

17. A wrap system for encircling and compressively wrapping a limb of a living person, the wrap system comprising:
an elastic garment sleeve having an open end into which an end of the limb can be inserted to allow the sleeve to be pulled over the limb to a position that elastically girdles the limb;
at least one strap for compressively wrapping the limb, the at least one strap having lengthwise opposite ends;
hook-type attachment material for attaching one lengthwise end of the strap to the sleeve;
the strap comprising a length of relatively stretchable material that has an outer face for facing away from a compressively wrapped limb and an inner face for facing toward a compressively wrapped limb; and
hook-type attachment material disposed on the inner face of the strap for attaching the lengthwise end of the strap opposite the one lengthwise end of the strap to one of a prior convolution of the strap and the elastic garment sleeve when the strap is compressively wrapping the limb, wherein the length of relatively stretchable material comprises a first lengthwise segment that presents, as the outer face, a loop-type fastening characteristic capable of detachably/re-attachably directly attaching to hook-type fastener material, and a second lengthwise segment that presents, as the inner face, a loop-type fastening characteristic capable of detachably/re-attachably directly attaching to hook-type fastener material.

18. A wrap system as set forth in claim 17 wherein the second lengthwise segment is located lengthwise between the first lengthwise segment and the hook-type attachment material for attaching one lengthwise end of the strap to the sleeve.

19. A wrap system for encircling and compressively wrapping a limb of a living person, the wrap system comprising:
an elastic garment sleeve having an open end into which an end of the limb can be inserted to allow the sleeve to be pulled over the limb to a position that elastically girdles the limb;
at least one strap for compressively wrapping the limb, the at least one strap having lengthwise opposite ends;
hook-type attachment material for attaching one lengthwise end of the strap to the sleeve;
the strap comprising a length of relatively stretchable material that has an outer face for facing away from the limb when the strap is encircling and compressively wrapping the limb and an inner face for facing toward the limb when the strap is encircling and compressively wrapping the limb, the inner face of the relatively stretchable material possessing a loop-type fastening characteristic capable of detachably/re-attachably attaching to hook-type fastener material; and
hook-type attachment material disposed on the inner face of the strap for attaching the lengthwise end of the strap opposite the one lengthwise end of the strap to one of a prior convolution of the strap and the elastic garment sleeve when the strap is compressively wrapping the limb.

20. A wrap system for encircling and compressively wrapping a limb of a living person, the wrap system comprising:
an elastic garment sleeve having an open end into which an end of the limb can be inserted to allow the sleeve to be pulled over the limb to a position that elastically girdles the limb;
at least one strap for compressively wrapping the limb, the at least one strap having lengthwise opposite ends;
hook-type attachment material for attaching one lengthwise end of the strap to the sleeve;
the strap comprising a length of relatively stretchable material that has an outer face for facing away from the limb when the wrap system is encircling and compressively wrapping the limb and an inner face for facing toward the limb when the wrap system is encircling and compressively wrapping the limb, the strap length being long enough to encircle the limb; and hook-type attachment material disposed on the inner face of the strap for attaching the lengthwise end of the strap opposite the one lengthwise end of the strap to one of a prior convolution of the strap and the elastic garment sleeve when the strap is compressively wrapping the limb, further including at least one strip of relatively non-stretchable material disposed lengthwise on the sleeve to prevent lengthwise stretching of the sleeve at the location of the strip.

21. A wrap system for encircling and compressively wrapping a limb of a living person, the wrap system comprising:
   an elastic garment sleeve having an open end into which an end of the limb can be inserted to allow the sleeve to be pulled over the limb to a position that elastically girdles the limb;
   at least one strap for compressively wrapping the limb, the at least one strap having lengthwise opposite ends;
   hook-type attachment material for attaching one lengthwise end of the strap to the sleeve;
   the strap comprising a length of relatively stretchable material that has an outer face for facing away from the limb when the wrap system is encircling and compressively wrapping the limb and an inner face for facing toward the limb when the wrap system is encircling and compressively wrapping the limb, the inner face of the relatively stretchable material possessing a loop-type fastening characteristic capable of detachably/re-attachably attaching to hook-type fastener material; and
   hook-type attachment material disposed on the inner face of the strap for attaching the end of the strap which is opposite the one lengthwise end of the strap to one of a prior convolution of the strap and the elastic garment sleeve when the strap is compressively wrapping the limb, wherein the elastic garment sleeve comprises a leg of a garment that includes an elastic brief that is shaped to be worn around a person's lower abdomen and buttock.

22. A wrap system for encircling and compressively wrapping a limb of a living person, the wrap system comprising:
   an elastic garment sleeve having an open end into which an end of the limb can be inserted to allow the sleeve to be pulled over the limb to a position that elastically girdles the limb;
   multiple straps for compressively wrapping the limb, each strap having lengthwise opposite ends;
   hook-type attachment material for attaching one lengthwise end of each strap to the sleeve;
   each strap comprising a length of relatively stretchable material that has an outer face for facing away from the limb when the strap is encircling and compressively wrapping the limb and an inner face for facing toward the limb when the strap is encircling and compressively wrapping the limb, the inner face of the relatively stretchable material possessing a loop-type fastening characteristic capable of detachably/re-attachably attaching to hook-type fastener material; and
   hook-type attachment material disposed on the inner face of each strap for attaching the end of each strap which is opposite each strap's one end to one of a prior convolution of the strap and the elastic garment sleeve when each strap is compressively wrapping the limb with a margin overlapping another strap.

23. A wrap system for encircling and compressively wrapping a limb of a living person, the wrap system comprising:
   an elastic garment sleeve having an open end into which an end of the limb can be inserted to allow the sleeve to be pulled over the limb to a position that elastically girdles the limb;
   at least one strap for compressively wrapping the limb, the at least one strap having lengthwise opposite ends;
   hook-type attachment material for attaching one lengthwise end of the strap to the sleeve;
   the strap comprising a length of relatively stretchable material that has an outer face for facing away from the limb when the strap is encircling and compressively wrapping the limb and an inner face for facing toward the limb when the strap is encircling and compressively wrapping the limb, the strap having a length for wrapping multiple convolutions around the limb, the inner face of the relatively stretchable material possessing a loop-type fastening characteristic capable of detachably/re-attachably attaching to hook-type fastener material; and
   hook-type attachment material disposed on the inner face of the strap at the end of the strap opposite the one lengthwise end of the strap for attaching the strap to one of a prior convolution of the strap and the elastic garment sleeve when multiple convolutions of the strap are compressively wrapping the limb.

* * * * *